(12) United States Patent
Fallon et al.

(10) Patent No.: US 11,364,287 B2
(45) Date of Patent: *Jun. 21, 2022

(54) METHODS OF TREATING CELIAC DISEASE

(71) Applicant: Curemark, LLC, Rye Brook, NY (US)

(72) Inventors: Joan M. Fallon, White Plains, NY (US); Matthew F. Heil, Sherman, CT (US); James Szigethy, Montgomery, NY (US); James J. Fallon, Armonk, NY (US)

(73) Assignee: CUREMARK, LLC, Rye Brook, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/422,462

(22) Filed: May 24, 2019

(65) Prior Publication Data

US 2019/0275123 A1  Sep. 12, 2019

Related U.S. Application Data

(63) Continuation of application No. 13/866,135, filed on Mar. 15, 2013, now Pat. No. 10,350,278.

(60) Provisional application No. 61/653,253, filed on May 30, 2012.

(51) Int. Cl.

| | | |
|---|---|---|
| *A61K 38/54* | (2006.01) | |
| *A61K 38/46* | (2006.01) | |
| *A61K 38/47* | (2006.01) | |
| *A61K 38/48* | (2006.01) | |

(52) U.S. Cl.
CPC ............ *A61K 38/54* (2013.01); *A61K 38/465* (2013.01); *A61K 38/47* (2013.01); *A61K 38/48* (2013.01)

(58) Field of Classification Search
None
See application file for complete search history.

(56) References Cited

U.S. PATENT DOCUMENTS

| | | |
|---|---|---|
| 3,002,883 A | 10/1961 | Bum et al. |
| 3,223,594 A | 12/1965 | Hoek |
| 3,322,626 A | 5/1967 | D'Argento |
| 3,357,894 A | 12/1967 | Uriel et al. |
| 3,515,642 A | 6/1970 | Hiroyuki et al. |
| 3,536,809 A | 10/1970 | Applezweig et al. |
| 3,574,819 A | 4/1971 | Franz et al. |
| 3,598,123 A | 8/1971 | Zaffaroni |
| 3,710,795 A | 1/1973 | Higuchi et al. |
| 3,786,615 A | 1/1974 | Bauer |
| 3,845,770 A | 11/1974 | Theeuwes et al. |
| 3,860,708 A | 1/1975 | Prout |
| 3,916,899 A | 11/1975 | Theeuwes et al. |
| 3,940,478 A | 2/1976 | Kurtz |
| RE28,819 E | 5/1976 | Thompson |
| 4,008,719 A | 2/1977 | Theeuwes et al. |
| 4,044,126 A | 8/1977 | Cook et al. |
| 4,079,125 A | 3/1978 | Sipos |
| 4,145,410 A | 3/1979 | Sears |
| 4,199,322 A | 4/1980 | Danna et al. |
| 4,241,046 A | 12/1980 | Papahadjopoulos et al. |
| 4,280,971 A | 7/1981 | Wischniewski et al. |
| 4,328,245 A | 5/1982 | Yu et al. |
| 4,358,603 A | 11/1982 | Yu |
| 4,364,923 A | 12/1982 | Cook et al. |
| 4,395,454 A | 7/1983 | Baldwin |
| 4,409,239 A | 10/1983 | Yu |
| 4,410,545 A | 10/1983 | Yu et al. |
| 4,414,209 A | 11/1983 | Cook et al. |
| 4,447,412 A | 5/1984 | Bilton |
| 4,456,544 A | 6/1984 | Lupova et al. |
| 4,500,515 A | 2/1985 | Libby |
| 4,623,624 A | 11/1986 | Schultze |
| 4,710,384 A | 12/1987 | Rotman |
| 4,826,679 A | 5/1989 | Roy |
| 4,965,012 A | 10/1990 | Olson |
| 5,023,108 A | 6/1991 | Bagaria et al. |
| 5,059,595 A | 10/1991 | Le Grazie |
| 5,073,543 A | 12/1991 | Marshall et al. |
| 5,120,548 A | 6/1992 | McClelland et al. |
| 5,190,775 A | 3/1993 | Klose |
| 5,227,166 A | 7/1993 | Ueda et al. |

(Continued)

FOREIGN PATENT DOCUMENTS

| | | |
|---|---|---|
| CA | 2198317 A1 | 8/1998 |
| CA | 2263703 A1 | 8/1999 |

(Continued)

OTHER PUBLICATIONS

Amsterdam, D. Susceptibility testing of antimicrobials in liquid media. Antibiotics in Laboratory Medicine. 52-111 (1996).
Barboza et al., Measurement of intestinal permeability using mannitol and lactulose in children with diarrheal diseases. Brazilian Journal of Medical and Biological Research 32: 1499-1504(1999).
Barry, J. Mode of action of penetration enhancers in human skin. Controlled Release 6: 85-97 (1987).
Capua et al., Influenza A viruses grow in human pancreatic cells and cause pancreatitis and diabetes in an animal model. Journal of Virology 87(1): 597-610 (2013).
DeFelice, Viruses Part 2-results of two informal studies, Chapter 14. In: Enzymes: Go with your Gut—more practical guidelines for digestive enzymes. Published by ThunderSnow. pp. 195-218 (2006).

(Continued)

*Primary Examiner* — Michelle F. Paguio Frising
(74) *Attorney, Agent, or Firm* — Wilson Sonsini Goodrich & Rosati

(57) ABSTRACT

Described herein are compositions which include digestive enzymes and which are formulated to reduce one or more symptoms of Celiac Disease. Also described herein is a method for treating a subject with Celiac Disease using digestive enzymes and their derivatives to alleviate the symptoms of Celiac Disease. The method comprises administering to the individual an effective amount of digestive enzymes that are either naturally or recombinantly derived, or their derivatives, in an amount effective to reduce one or more symptoms of Celiac Disease.

11 Claims, 1 Drawing Sheet

(56) References Cited

U.S. PATENT DOCUMENTS

| | | |
|---|---|---|
| 5,250,418 A | 10/1993 | Moeller et al. |
| 5,324,514 A | 6/1994 | Sipos |
| 5,354,556 A | 10/1994 | Sparks et al. |
| 5,378,462 A | 1/1995 | Boedecker et al. |
| 5,436,319 A | 7/1995 | Kung et al. |
| 5,437,319 A | 8/1995 | Garuglieri |
| 5,439,935 A | 8/1995 | Rawlings et al. |
| 5,460,812 A | 10/1995 | Sipos |
| 5,476,661 A | 12/1995 | Pillai et al. |
| 5,527,678 A | 6/1996 | Blaser et al. |
| 5,585,115 A | 12/1996 | Sherwood et al. |
| 5,591,767 A | 1/1997 | Mohr et al. |
| 5,607,863 A | 3/1997 | Chandler |
| 5,639,476 A | 6/1997 | Oshlack et al. |
| 5,648,335 A | 7/1997 | Lewis et al. |
| 5,674,532 A | 10/1997 | Atzl et al. |
| 5,674,533 A | 10/1997 | Santus et al. |
| 5,686,255 A | 11/1997 | Deth |
| 5,686,311 A | 11/1997 | Shaw |
| 5,750,104 A | 5/1998 | Sipos |
| 5,753,223 A | 5/1998 | Shibahara et al. |
| 5,776,917 A | 7/1998 | Blank et al. |
| 5,858,758 A | 1/1999 | Hillman et al. |
| 5,860,957 A | 1/1999 | Jacobsen et al. |
| 5,948,433 A | 9/1999 | Burton et al. |
| 5,952,178 A | 9/1999 | Lapidus et al. |
| 5,958,875 A | 9/1999 | Longo et al. |
| 5,977,175 A | 11/1999 | Lin |
| 5,983,134 A | 11/1999 | Ostrow |
| 5,985,317 A | 11/1999 | Venkateshwaran et al. |
| 5,985,891 A | 11/1999 | Rowe |
| 6,010,715 A | 1/2000 | Wick et al. |
| 6,011,001 A | 1/2000 | Navia et al. |
| 6,013,286 A | 1/2000 | Klose |
| 6,020,310 A | 2/2000 | Beck et al. |
| 6,020,314 A | 2/2000 | McMichael |
| 6,024,975 A | 2/2000 | D'Angelo et al. |
| 6,096,338 A | 8/2000 | Lacy et al. |
| 6,100,080 A | 8/2000 | Johansen |
| 6,149,585 A | 11/2000 | Gray |
| 6,153,236 A | 11/2000 | Wu et al. |
| 6,167,301 A | 12/2000 | Flower et al. |
| 6,168,569 B1 | 1/2001 | McEwen et al. |
| 6,187,309 B1 | 2/2001 | McMichael et al. |
| 6,197,746 B1 | 3/2001 | Beck et al. |
| 6,210,950 B1 | 4/2001 | Johnson et al. |
| 6,238,727 B1 | 5/2001 | Takemoto et al. |
| 6,251,478 B1 | 6/2001 | Pacifico et al. |
| 6,256,533 B1 | 7/2001 | Yuzhakov et al. |
| 6,261,595 B1 | 7/2001 | Stanley et al. |
| 6,261,602 B1 | 7/2001 | Calanchi et al. |
| 6,261,613 B1 | 7/2001 | Narayanaswamy et al. |
| 6,267,983 B1 | 7/2001 | Fujii et al. |
| 6,280,726 B1 | 8/2001 | Weinrauch et al. |
| 6,287,585 B1 | 9/2001 | Johansen |
| 6,309,669 B1 | 10/2001 | Setterstrom et al. |
| 6,312,741 B1 | 11/2001 | Navarro |
| 6,399,101 B1 | 6/2002 | Frontanes et al. |
| 6,482,839 B1 | 11/2002 | Thornfeldt |
| 6,498,143 B1 | 12/2002 | Beck et al. |
| 6,534,063 B1 | 3/2003 | Fallon |
| 6,534,259 B1 | 3/2003 | Wakefield |
| 6,558,708 B1 | 5/2003 | Lin |
| 6,562,629 B1 | 5/2003 | Lin et al. |
| 6,569,463 B2 | 5/2003 | Patel et al. |
| 6,616,954 B1 | 9/2003 | Dally et al. |
| 6,632,429 B1 | 10/2003 | Fallon |
| 6,660,831 B2 | 12/2003 | Fallon |
| 6,699,885 B2 | 3/2004 | Phillips |
| 6,727,073 B1 | 4/2004 | Moore et al. |
| 6,743,447 B2 | 6/2004 | Labergerie et al. |
| 6,764,447 B2 | 7/2004 | Iliff |
| 6,783,757 B2 | 8/2004 | Brudnak |
| 6,790,825 B2 | 9/2004 | Beck et al. |
| 6,797,291 B2 | 9/2004 | Richardson |
| 6,808,708 B2 | 10/2004 | Houston |
| 6,821,514 B2 | 11/2004 | Houston |
| 6,827,688 B2 | 12/2004 | Goto et al. |
| 6,835,397 B2 | 12/2004 | Lee et al. |
| 6,852,487 B1 | 2/2005 | Barany et al. |
| 6,861,053 B1 | 3/2005 | Lin et al. |
| 6,890,561 B1 | 5/2005 | Blatt et al. |
| 6,899,876 B2 | 5/2005 | Houston |
| 6,923,988 B2 | 8/2005 | Patel et al. |
| 6,980,958 B1 | 12/2005 | Surwit et al. |
| 7,048,906 B2 | 5/2006 | Lin et al. |
| 7,081,239 B2 | 7/2006 | Lin |
| 7,091,182 B2 | 8/2006 | Beck et al. |
| 7,101,573 B2 | 9/2006 | Szymczak et al. |
| 7,122,357 B2 | 10/2006 | Sander-Struckmeier et al. |
| 7,129,053 B1 | 10/2006 | Reiter et al. |
| 7,138,123 B2 | 11/2006 | Fallon |
| 7,232,670 B2 | 6/2007 | D'Azzo et al. |
| 7,244,412 B2 | 7/2007 | Lin |
| 7,285,633 B2 | 10/2007 | Wu et al. |
| RE40,059 E | 2/2008 | Pacifico et al. |
| 7,381,698 B2 | 6/2008 | Fein et al. |
| 7,395,216 B2 | 7/2008 | Rosenfeld et al. |
| 7,479,378 B2 | 1/2009 | Potthoff et al. |
| 7,483,747 B2 | 1/2009 | Gliner et al. |
| 7,588,757 B2 | 9/2009 | Ozawa et al. |
| 7,608,245 B2 | 10/2009 | Lin |
| 7,630,913 B2 | 12/2009 | Kay |
| 7,658,918 B1 | 2/2010 | Ortenzi et al. |
| 7,718,169 B2 | 5/2010 | Margolin et al. |
| 7,736,622 B2 | 6/2010 | Lin et al. |
| 7,935,799 B2 | 5/2011 | Lin et al. |
| 7,945,451 B2 | 5/2011 | Cosentino et al. |
| 8,008,036 B2 | 8/2011 | Fallon |
| 8,012,710 B2 | 9/2011 | Fallon |
| 8,012,930 B2 | 9/2011 | Fallon |
| 8,030,002 B2 | 10/2011 | Fallon |
| 8,055,516 B2 | 11/2011 | Iliff |
| 8,066,636 B2 | 11/2011 | Iliff |
| 8,084,025 B2 | 12/2011 | Fallon |
| 8,105,584 B2 | 1/2012 | Fallon |
| 8,163,278 B2 | 4/2012 | Fallon |
| 8,211,661 B2 | 7/2012 | Fallon |
| 8,221,747 B2 | 7/2012 | Ortenzi et al. |
| 8,318,158 B2 | 11/2012 | Fallon |
| 8,437,689 B2 | 5/2013 | Mazar |
| 8,486,390 B2 | 7/2013 | Fallon |
| 8,580,522 B2 | 11/2013 | Fallon |
| 8,613,918 B2 | 12/2013 | Fallon |
| 8,658,163 B2 | 2/2014 | Fallon |
| 8,673,877 B2 | 3/2014 | Fallon et al. |
| 8,778,335 B2 | 7/2014 | Fallon |
| 8,815,233 B2 | 8/2014 | Fallon |
| 8,921,054 B2 | 12/2014 | Fallon |
| 8,980,252 B2 | 3/2015 | Fallon et al. |
| 9,017,665 B2 | 4/2015 | Fallon |
| 9,023,344 B2 | 5/2015 | Fallon |
| 9,056,050 B2 | 6/2015 | Fallon et al. |
| 9,061,033 B2 | 6/2015 | Fallon |
| 9,084,784 B2 | 7/2015 | Fallon et al. |
| 9,107,419 B2 | 8/2015 | Fallon et al. |
| 9,233,146 B2 | 1/2016 | Fallon |
| 9,320,780 B2 | 4/2016 | Fallon |
| 9,345,721 B2 | 5/2016 | Fallon et al. |
| 9,377,459 B2 | 6/2016 | Fallon |
| 9,408,895 B2 | 8/2016 | Fallon |
| 9,492,515 B2 | 11/2016 | Fallon et al. |
| 9,511,125 B2 | 12/2016 | Fallon et al. |
| 9,624,525 B2 | 4/2017 | Fallon |
| 9,624,526 B2 | 4/2017 | Fallon |
| 9,687,534 B2 | 6/2017 | Fallon |
| 9,895,427 B2 | 2/2018 | Fallon et al. |
| 9,925,250 B2 | 3/2018 | Joan |
| 9,931,302 B2 | 4/2018 | Fallon et al. |
| 10,098,844 B2 | 10/2018 | Fallon et al. |
| 10,209,253 B2 | 2/2019 | Joan |
| 10,272,141 B2 | 4/2019 | Fallon |
| 10,279,016 B2 | 5/2019 | Fallon |
| 10,350,229 B2 | 7/2019 | Fallon et al. |

(56) References Cited

U.S. PATENT DOCUMENTS

| | | |
|---|---|---|
| 10,350,278 B2 | 7/2019 | Fallon et al. |
| 10,413,601 B2 | 9/2019 | Joan |
| 2001/0006644 A1 | 7/2001 | Bova et al. |
| 2001/0023360 A1 | 9/2001 | Nelson et al. |
| 2001/0024660 A1 | 9/2001 | Ullah et al. |
| 2002/0001575 A1 | 1/2002 | Foreman |
| 2002/0037284 A1 | 3/2002 | Fallon |
| 2002/0061302 A1 | 5/2002 | Sander-Struckmeier et al. |
| 2002/0081628 A1 | 6/2002 | Fallon |
| 2002/0090653 A1 | 7/2002 | Fallon |
| 2002/0094367 A1 | 7/2002 | Fuglsang et al. |
| 2002/0103675 A1 | 8/2002 | Vanelli |
| 2002/0119914 A1 | 8/2002 | Zhu et al. |
| 2002/0141987 A1 | 10/2002 | Bjarnason |
| 2002/0183229 A1 | 12/2002 | Simpson |
| 2003/0097122 A1 | 5/2003 | Ganz et al. |
| 2004/0005304 A1 | 1/2004 | Brudnak |
| 2004/0028689 A1 | 2/2004 | Borody |
| 2004/0029752 A1 | 2/2004 | Sava et al. |
| 2004/0057944 A1 | 3/2004 | Galle et al. |
| 2004/0057962 A1 | 3/2004 | Timmerman |
| 2004/0071683 A1 | 4/2004 | Fallon |
| 2004/0076590 A1 | 4/2004 | Wilkins |
| 2004/0101562 A1 | 5/2004 | Maio |
| 2004/0121002 A1 | 6/2004 | Lee et al. |
| 2004/0209790 A1 | 10/2004 | Sava et al. |
| 2005/0026892 A1 | 2/2005 | Bodor |
| 2005/0036950 A1 | 2/2005 | Jones et al. |
| 2005/0079594 A1 | 4/2005 | Marion |
| 2005/0137134 A1 | 6/2005 | Gill et al. |
| 2005/0170479 A1 | 8/2005 | Weaver et al. |
| 2005/0187130 A1 | 8/2005 | Brooker et al. |
| 2005/0232894 A1 | 10/2005 | Weiner et al. |
| 2006/0105379 A1 | 5/2006 | Wu et al. |
| 2006/0115467 A1 | 6/2006 | Pangborn et al. |
| 2006/0121017 A1 | 6/2006 | Margolin et al. |
| 2006/0182728 A1 | 8/2006 | Fallon |
| 2006/0183180 A1 | 8/2006 | Fallon |
| 2006/0198838 A1 | 9/2006 | Fallon |
| 2006/0253045 A1 | 11/2006 | Coifman |
| 2006/0258599 A1 | 11/2006 | Childers |
| 2006/0258708 A1 | 11/2006 | Andrulis, Jr. |
| 2006/0259995 A1 | 11/2006 | Cayouette et al. |
| 2006/0294108 A1 | 12/2006 | Adelson et al. |
| 2007/0031399 A1 | 2/2007 | Edens et al. |
| 2007/0053895 A1 | 3/2007 | Fallon |
| 2007/0092501 A1 | 4/2007 | Houston |
| 2007/0116695 A1 | 5/2007 | Fallon |
| 2007/0148151 A1 | 6/2007 | Frink et al. |
| 2007/0148152 A1 | 6/2007 | Shlieout et al. |
| 2007/0148153 A1 | 6/2007 | Shlieout et al. |
| 2007/0203426 A1 | 8/2007 | Kover et al. |
| 2008/0019959 A1 | 1/2008 | Becher et al. |
| 2008/0020036 A1 | 1/2008 | Jolly |
| 2008/0057086 A1 | 3/2008 | Etter |
| 2008/0058282 A1 | 3/2008 | Fallon et al. |
| 2008/0112900 A1 | 5/2008 | Du-Thumm et al. |
| 2008/0112944 A1 | 5/2008 | Pangborn et al. |
| 2008/0152637 A1 | 6/2008 | Fallon |
| 2008/0161265 A1 | 7/2008 | Fallon et al. |
| 2008/0166334 A1 | 7/2008 | Fallon |
| 2008/0177578 A1 | 7/2008 | Zakim |
| 2008/0187525 A1 | 8/2008 | Porubcan |
| 2008/0193436 A1* | 8/2008 | Shan .............. A61K 38/482 424/94.63 |
| 2008/0199448 A1 | 8/2008 | Ross et al. |
| 2008/0219966 A1 | 9/2008 | Fallon |
| 2008/0248558 A1 | 10/2008 | Deinhammer et al. |
| 2008/0254009 A1 | 10/2008 | Finegold |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0311554 A1 | 12/2008 | Slotman |
| 2008/0317731 A1 | 12/2008 | Gramatikova et al. |
| 2009/0004285 A1 | 1/2009 | Yu et al. |
| 2009/0063402 A1 | 3/2009 | Hayter |
| 2009/0110674 A1 | 4/2009 | Loizou |
| 2009/0117180 A1 | 5/2009 | Ortenzi et al. |
| 2009/0130081 A1 | 5/2009 | Fallon |
| 2009/0171696 A1 | 7/2009 | Allard et al. |
| 2009/0197289 A1 | 8/2009 | Fallon |
| 2009/0226414 A1 | 9/2009 | Tijssen et al. |
| 2009/0232789 A1 | 9/2009 | Fallon |
| 2009/0233344 A1 | 9/2009 | Kurfurst et al. |
| 2009/0263372 A1 | 10/2009 | Fallon |
| 2009/0285790 A1 | 11/2009 | Fallon |
| 2009/0286270 A1 | 11/2009 | Fallon |
| 2009/0304670 A1 | 12/2009 | Edens et al. |
| 2009/0324572 A1 | 12/2009 | Fallon |
| 2009/0324730 A1 | 12/2009 | Fallon |
| 2010/0092447 A1 | 4/2010 | Fallon |
| 2010/0169409 A1 | 7/2010 | Fallon et al. |
| 2010/0196344 A1 | 8/2010 | Margolin et al. |
| 2010/0209507 A1 | 8/2010 | Lin et al. |
| 2010/0233218 A1 | 9/2010 | Fallon |
| 2010/0239559 A1 | 9/2010 | Freedman et al. |
| 2010/0260857 A1 | 10/2010 | Fallon et al. |
| 2010/0270183 A1 | 10/2010 | Ortenzi et al. |
| 2010/0285116 A1 | 11/2010 | Joshi |
| 2011/0029922 A1 | 2/2011 | Hoffberg et al. |
| 2011/0052706 A1 | 3/2011 | Moest et al. |
| 2011/0065628 A1 | 3/2011 | Johnson et al. |
| 2011/0081320 A1 | 4/2011 | Westall et al. |
| 2011/0112005 A1 | 5/2011 | Brooker et al. |
| 2011/0182818 A1 | 7/2011 | Fallon |
| 2011/0200574 A1 | 8/2011 | Jolly et al. |
| 2011/0280853 A1* | 11/2011 | Fallon .............. A61K 38/47 424/94.2 |
| 2011/0280854 A1 | 11/2011 | Fallon et al. |
| 2012/0003628 A1 | 1/2012 | Fallon |
| 2012/0004192 A1 | 1/2012 | Fallon et al. |
| 2012/0027848 A1 | 2/2012 | Fallon et al. |
| 2012/0070504 A1 | 3/2012 | Fallon |
| 2012/0128764 A1 | 5/2012 | Venkatesh et al. |
| 2012/0189703 A1 | 7/2012 | Fallon et al. |
| 2012/0201875 A1 | 8/2012 | Ortenzi et al. |
| 2012/0207740 A1 | 8/2012 | Fallon |
| 2012/0230970 A1 | 9/2012 | Fallon |
| 2013/0059001 A1 | 3/2013 | Fallon |
| 2013/0095152 A1 | 4/2013 | Fallon |
| 2013/0113129 A1 | 5/2013 | Fallon et al. |
| 2013/0171121 A1* | 7/2013 | Pierzynowski ...... A61K 38/465 424/94.2 |
| 2013/0195833 A1 | 8/2013 | Fallon |
| 2013/0202581 A1 | 8/2013 | Fallon et al. |
| 2013/0224172 A1 | 8/2013 | Fallon et al. |
| 2014/0030333 A1 | 1/2014 | Fallon |
| 2014/0127184 A1 | 5/2014 | Fallon et al. |
| 2014/0147500 A1 | 5/2014 | Fallon et al. |
| 2014/0161787 A1 | 6/2014 | Fallon |
| 2014/0170637 A1 | 6/2014 | Fallon |
| 2014/0348881 A1 | 11/2014 | Fallon |
| 2015/0023944 A1 | 1/2015 | Fallon |
| 2015/0147308 A1 | 5/2015 | Fallon et al. |
| 2015/0151198 A1 | 6/2015 | Dugan et al. |
| 2015/0182607 A1 | 7/2015 | Jolly et al. |
| 2015/0246105 A1 | 9/2015 | Fallon et al. |
| 2015/0273030 A1 | 10/2015 | Fallon |
| 2015/0335589 A1 | 11/2015 | Fallon et al. |
| 2016/0045576 A1 | 2/2016 | Fallon et al. |
| 2016/0206708 A1 | 7/2016 | Fallon et al. |
| 2017/0157221 A1 | 6/2017 | Fallon |
| 2017/0202934 A1 | 7/2017 | Fallon |
| 2017/0246265 A1 | 8/2017 | Fallon |
| 2018/0071375 A1 | 3/2018 | Fallon |
| 2018/0104315 A1 | 4/2018 | Joan |
| 2018/0161409 A1 | 6/2018 | Fallon |
| 2018/0243282 A1 | 8/2018 | Fallon |
| 2018/0296650 A1 | 10/2018 | Fallon |
| 2018/0360759 A1 | 12/2018 | Fallon |
| 2019/0175704 A1 | 6/2019 | Fallon |
| 2019/0183990 A1 | 6/2019 | Fallon et al. |
| 2019/0201507 A1 | 7/2019 | Fallon |
| 2019/0209667 A1 | 7/2019 | Fallon |

(56) References Cited

U.S. PATENT DOCUMENTS

| | | |
|---|---|---|
| 2019/0275066 A1 | 9/2019 | Fallon et al. |
| 2019/0275128 A1 | 9/2019 | Gleiberman et al. |
| 2020/0101145 A1 | 4/2020 | Fallon et al. |
| 2020/0282030 A1 | 9/2020 | Fallon et al. |
| 2020/0286620 A1 | 9/2020 | Fallon et al. |
| 2021/0162024 A1 | 6/2021 | Fallon et al. |
| 2021/0270846 A1 | 9/2021 | Fallon |

FOREIGN PATENT DOCUMENTS

| | | |
|---|---|---|
| CA | 2667976 A1 | 5/2008 |
| CA | 2719102 A1 | 9/2009 |
| CN | 1031562 A | 3/1989 |
| CN | 1275897 A | 12/2000 |
| CN | 1329923 A | 1/2002 |
| CN | 1552836 A | 12/2004 |
| CN | 1791430 A | 6/2006 |
| CN | 101039667 A | 9/2007 |
| CN | 101208092 A | 6/2008 |
| CN | 102300989 A | 12/2011 |
| CN | 102984941 A | 3/2013 |
| DE | 3738599 A1 | 5/1989 |
| DE | 4332985 A1 | 3/1995 |
| DE | 202010004926 U1 | 7/2010 |
| EP | 0425214 A2 | 5/1991 |
| EP | 0436110 A1 | 7/1991 |
| EP | 0451484 A1 | 10/1991 |
| EP | 0564739 A2 | 10/1993 |
| EP | 0564739 A3 | 4/1995 |
| EP | 1162995 B1 | 6/2003 |
| EP | 1413202 A1 | 4/2004 |
| EP | 1335706 B1 | 4/2005 |
| EP | 1019072 B1 | 5/2005 |
| EP | 1604677 A1 | 12/2005 |
| EP | 1931317 B1 | 12/2008 |
| EP | 2258837 A1 | 12/2010 |
| EP | 2318035 A1 | 5/2011 |
| EP | 2373791 A1 | 10/2011 |
| GB | 669782 A | 4/1952 |
| GB | 2347742 A | 9/2000 |
| GB | 2480772 A | 11/2011 |
| GB | 2506537 A | 4/2014 |
| JP | S523819 A | 1/1977 |
| JP | S62230714 A | 10/1987 |
| JP | H04364119 A | 12/1992 |
| JP | 2003517831 A | 6/2003 |
| JP | 2004500591 A | 1/2004 |
| JP | 2005515223 A | 5/2005 |
| JP | 2006512091 A | 4/2006 |
| JP | 2007523664 A | 8/2007 |
| JP | 2007530503 A | 11/2007 |
| JP | 2008512468 A | 4/2008 |
| JP | 2008521906 A | 6/2008 |
| JP | 2008283895 A | 11/2008 |
| JP | 2013517251 A | 5/2013 |
| KR | 20050084485 A | 8/2005 |
| RU | 2356244 C1 | 5/2009 |
| TW | 310277 B | 7/1997 |
| WO | WO-8402846 A1 | 8/1984 |
| WO | WO-8908694 A1 | 9/1989 |
| WO | WO-9002562 A1 | 3/1990 |
| WO | WO-9219708 A1 | 11/1992 |
| WO | WO-9219709 A1 | 11/1992 |
| WO | WO-9419005 A1 | 9/1994 |
| WO | WO-9522344 A1 | 8/1995 |
| WO | WO-9732480 A1 | 9/1997 |
| WO | WO-9822499 A2 | 5/1998 |
| WO | WO-9826807 A1 | 6/1998 |
| WO | WO-9822499 A3 | 7/1998 |
| WO | WO-9832336 A2 | 7/1998 |
| WO | WO-9852593 A1 | 11/1998 |
| WO | WO-9964059 A2 | 12/1999 |
| WO | WO-0009142 A1 | 2/2000 |
| WO | WO-9964059 A3 | 3/2000 |
| WO | WO-0021504 A1 | 4/2000 |
| WO | WO-0127612 A2 | 4/2001 |
| WO | WO-0143764 A2 | 6/2001 |
| WO | WO-0145835 A1 | 6/2001 |
| WO | WO-0127612 A3 | 10/2001 |
| WO | WO-0143764 A3 | 11/2001 |
| WO | WO-0214537 A2 | 2/2002 |
| WO | WO-0219828 A1 | 3/2002 |
| WO | WO-0214537 A3 | 5/2002 |
| WO | WO-02051352 A2 | 7/2002 |
| WO | WO-02051436 A2 | 7/2002 |
| WO | WO-03051345 A2 | 6/2003 |
| WO | WO-03059088 A1 | 7/2003 |
| WO | WO-2004060074 A1 | 7/2004 |
| WO | WO-2004093883 A2 | 11/2004 |
| WO | WO-2005092370 A1 | 10/2005 |
| WO | WO-2005115445 A1 | 12/2005 |
| WO | WO-2006031554 A2 | 3/2006 |
| WO | WO-2006044529 A1 | 4/2006 |
| WO | WO-2006060414 A2 | 6/2006 |
| WO | WO-2006031554 A3 | 9/2006 |
| WO | WO-2007002572 A2 | 1/2007 |
| WO | WO-2007074454 A2 | 7/2007 |
| WO | WO-2007147714 A1 | 12/2007 |
| WO | WO-2008021987 A2 | 2/2008 |
| WO | WO-2008102264 A2 | 8/2008 |
| WO | WO-2009114757 A2 | 9/2009 |
| WO | WO-2009155689 A1 | 12/2009 |
| WO | WO-2010002972 A1 | 1/2010 |
| WO | WO-2010025126 A1 | 3/2010 |
| WO | WO-2010080830 A1 | 7/2010 |
| WO | WO-2010080835 A1 | 7/2010 |
| WO | WO-2010120781 A1 | 10/2010 |
| WO | WO-2011000924 A1 | 1/2011 |
| WO | WO-2011050135 A1 | 4/2011 |
| WO | WO-2011086126 A1 | 7/2011 |
| WO | WO-2011114225 A1 | 9/2011 |
| WO | WO-2012067621 A1 | 5/2012 |
| WO | WO-2012145651 A2 | 10/2012 |
| WO | WO-2013103746 A1 | 7/2013 |
| WO | WO-2013116732 A1 | 8/2013 |
| WO | WO-2013181447 A1 | 12/2013 |

OTHER PUBLICATIONS

D'Eufemia et al., Abnormal intestinal permeability in children with autism. Acta Paediatr 85: 1076-1079 (1996).

Horsmans et al., Lactulose improves psychometric testing in cirrhotic patients with subclinical encephalopathy. Aliment Pharmocol Ther 11:165-170 (1997).

International Preliminary Report on Patentability dated Oct. 15, 2019 for PCT/US2018/026841.

National Institutes of Health. Thin Bones Seen in Boys with Autism and Autism Spectrum Disorder. 3 pages (2008).

Schlessingerman, Mass of an Adult. The Physics Factbook (2003).

Singh et al. Past, Present, and Future Technologies for Oral Delivery of Therapeutic Proteins. J Pham Sci 97(7):2497-2523 (2008).

U.S. Appl. No. 13/733,873 Final Office Action dated Feb. 6, 2020.

U.S. Appl. No. 15/889,917 Final Office Action dated Feb. 13, 2020.

U.S. Appl. No. 16/103,192 Office Action dated Nov. 4, 2019.

U.S. Appl. No. 12/535,676 Notice of Allowance dated Apr. 1, 2020.

U.S. Appl. No. 13/002,136 Non-Final Office Action dated May 26, 2020.

U.S. Appl. No. 13/757,412 Non-Final Office Action dated Mar. 18, 2020.

U.S. Appl. No. 14/713,242 Notice of Allowance dated Apr. 2, 2020.

U.S. Appl. No. 15/074,115 Notice of Allowance dated Dec. 11, 2019.

U.S. Appl. No. 15/074,115 Notice of Allowance dated Feb. 11, 2020.

U.S. Appl. No. 15/265,620 Non-Final Office Action dated Jan. 30, 2020.

U.S. Appl. No. 15/265,620 Notice of Allowance dated Apr. 29, 2020.

U.S. Appl. No. 15/354,940 Final Office Action dated Jul. 2, 2020.

U.S. Appl. No. 15/840,883 Final Office Action dated Jun. 9, 2020.

(56) References Cited

OTHER PUBLICATIONS

U.S. Appl. No. 15/889,917 Office Action dated May 24, 2019.
U.S. Appl. No. 16/281,908 Non-Final Office Action dated May 1, 2020.
U.S. Appl. No. 16/296,546 Non-Final Office Action dated Feb. 14, 2020.
U.S. Appl. No. 16/422,079 Non-Final Office Action dated Apr. 20, 2020.
Wang et al., Extraction of Pancreatin from Pig Pancreas and Isolation and Purification of Kallikrein. Academic Journal of Kunming Medical College 1: 107-108 (2002).
ABCNEWS. Changing Face of Autism: Numbers Rise as More Behaviors Included. ABCnews. Nov. 1, 2007.
ADAMS. "Summary of Defeat Autism Now! (DNN!) Oct. 2001 Conference," retrieved from the internet Dec. 18, 2008. http://puterakembara.org/rm/DAN2001.htm.
Advisory Action dated Jun. 3, 2008 for U.S. Appl. No. 10/681,018.
Aman, et al. Outcome measures for clinical drug trials in autism. CNS Spectr. Jan. 2004;9(1):36-47.
Amendment dated Oct. 28, 2009 in Reply to Final Office Action dated Apr. 28, 2009 for U.S. Appl. No. 10/681,018.
Amendment dated Nov. 13, 2009 in Reply to Final Office Action dated Jul. 27, 2004 for U.S. Appl. No. 09/990,909.
Amendment dated Dec. 12, 2007 in Reply to Office Action dated Aug. 8, 2007 for U.S. Appl. No. 11/213,382.
Amendment dated Dec. 7, 2007 in Reply to Office Action dated Aug. 7, 2007 for U.S. Appl. No. 10/681,018.
Amendment dated Feb. 2, 2004 in Reply to Office Action dated Jul. 29, 2003 for U.S. Appl. No. 09/990,909.
Amendment dated Feb. 7, 2003 in Reply to Office Action dated Jul. 30, 2002 for U.S. Appl. No. 09/990,909.
Amendment dated Feb. 7, 2009 in Reply to Office Action dated Aug. 18, 2008 for U.S. Appl. No. 10/681,018.
Amendment dated Mar. 1, 2004 in Reply to Office Action dated Aug. 26, 2003 for U.S. Appl. No. 10/041,073.
Amendment dated Mar. 24, 2010 in Reply to Final Office Action dated Sep. 24, 2009 for U.S. Appl. No. 12/046,252.
Amendment dated Mar. 4, 2008 in Reply to Office Action dated Nov. 14, 2007 for U.S. Appl. No. 11/213,255.
Amendment dated May 18, 2007 in Reply to Office Action dated Dec. 22, 2006 for U.S. Appl. No. 10/681,018.
Amendment dated May 19, 2008 in Reply to Final Office Action dated Mar. 17, 2008 for U.S. Appl. No. 10/681,018.
Amendment dated May 27, 2009 in Reply to Final Office Action dated Feb. 27, 2009 for U.S. Appl. No. 11/555,697.
Amendment dated Jun. 15, 2009 in Reply to Final Office Action dated Mar. 13, 2009 for U.S. Appl. No. 11/232,180.
Amendment dated Jun. 8, 2010 in Reply to Office Action dated Jan. 8, 2010 for U.S. Appl. No. 10/681,018.
Amendment dated Aug. 21, 2008 in Reply to Office Action dated Apr. 21, 2008 for U.S. Appl. No. 11/232,180.
Amendment dated Aug. 28, 2008 in Reply to Office Action dated Mar. 28, 2008 for U.S. Appl. No. 11/555,697.
Amendment dated Sep. 25, 2008 in Reply to Final Office Action dated Jun. 25, 2008 for U.S. Appl. No. 11/213,255.
American Family Physician. Cuts, Scrapes, and Stitches. Am Fam Physician 69(11):2647-2648 (Jun. 1, 2004).
Anderson, George M., et al. Determination of serotonin in whole blood, platelet-rich plasma, platelet-poor plasma and plasma ultrafiltrate. Life Sciences 40(11):1063-1070 (Mar. 16, 1987) [Abstract Only].
Ang, et al. Biological role and regulation of the universally conserved heat shock proteins. J Biol Chem. Dec. 25, 1991;266(36):24233-6.
Anonymous: Emulsifiers for the preparation of active dry yeast, Research Disclosure, Mason Publications, Hampshire, GB, 236(6), Dec. 1983 (attached).
APDA. Basic Information About Parkinson's Disease. Jul. 14, 2008.
Arnold, GL et al. Plasma amino acids profiles in children with autism: potential risk of nutritional deficiencies. J. Autism Dev. Disord. 33(4):449-454 (Aug. 2003) [Abstract Only].
Arribas, et al. A comparative study of the chymotrypsin-like activity of the rat liver multicatalytic proteinase and the ClpP from *Escherichia coli*. J Biol Chem. Oct. 5, 1993;268(28):21165-71.
Arrigo, et al. Expression of heat shock proteins during development in *Drosophila*. Results Probl Cell Differ. 1991;17:106-19.
ASH. Patient Information Guide—Understanding Hypertension. American Society of Hypertension. 2004. 1-7.
Ashwood, et al. Immune activation of peripheral blood and mucosal CD3+ lymphocyte cytokine profiles in children with autism and gastrointestinal symptoms. J Neuroimmunol. Dec. 19, 2005; 1-9.
Ashwood, et al. Intestinal lymphocyte populations in children with regressive autism: evidence for extensive mucosal immunopathology. J Clin Immunol. Nov. 2003;23(6):504-17.
Ashwood, et al. Spontaneous mucosal lymphocyte cytokine profiles in children with autism and gastrointestinal symptoms: mucosal immune activation and reduced counter regulatory interleukin-10. J Clin Immunol. Nov. 2004;24(6):664-73.
Austic. Development and adaptation of protein digestion. J Nutr. May 1985;115(5):686-97.
Autism Diagnosis. Autism Statistics. Www.autism-diagnosis.com/autism_statistics/autism_statistics.html. 2007.
Autism Society of America. Incidence Numbers from Other Countries, www.autism-society.org. Accessed: Jul. 14, 2008.
Avruch, J., et al. Amino acid regulation of TOR complex 1. AJP: Endocrinology and Metabolism, Am. J. Physiol. Endocrinol. Metab. 296(4):E592-E602 (Apr. 2009).
Awazuhara, et al. Antigenicity of the proteins in soy lecithin and soy oil in soybean allergy. Clin Exp Allergy. Dec. 1998;28(12):1559-64.
Axcan Pharma Inc. Cdn Prescribing Information on VIOKASE Pancrelipase, USP tablets, powder. 2000: 1-3.
Axelrod FB et al. Hereditary sensory an autonomic neuropathies: types II, III and IV. Orphanet Journal of Rare Diseases, 2:39 (2007).
Axelrod. Secretin Treatment for Gastrointestinal Dysmobility in Patients with Familial Dysautonomia. New York University School of Medicine, Grant Recipient awards, Mar.-May 2000. www.med.nyu.edu/ogars/awards/awards2000/page2.html.
Azilect et al. "Correlation between protein intake and daily levodopa dosage," Obtained from the internet May 2, 2007, http://www.azilect.eu/media/cnsnews/showitem.aspx?i=d1c603e4-3c61-4aa1-a376-6e519a5a0f80.
Bailey, et al. Co-occurring conditions associated with FMR1 gene variations: findings from a national parent survey. Am J Med Genet A. Aug. 15, 2008;146A(16):2060-9.
Bakkaloglu, et al. Atopic features in early childhood autism. Eur J Paediatr Neurol. Nov. 2008;12(6):476-9.
Balasubramanian, Mukundh N. et al. Asparagine synthetase: regulation by cell stress and involvement in tumor biology, Am. J. Physiol. Endocrinol. Metab. 304(8):E789-E799 (Apr. 15, 2013).
Barlow. A comparison of the blood pressure, kidney volume and the pancreatic secretory response following the vein administration of various secretin preparations. Am J Phys. 1927;81:182-188.
Barnhart, et al. Symptomatic granular cell tumor involving the pituitary gland in a dog: a case report and review of the literature. Vet Pathol. May 2001;38(3):332-6.
Beilmann, et al. Neoexpression of the c-met/hepatocyte growth factor-scatter factor receptor gene in activated monocytes. Blood. Dec. 1, 1997;90(11):4450-8.
Beliaev, O.A. The therapeutic efficacy of the triase preparation in experimental pancreatic exocrine insufficiency. Eksp Lin Farmakiol. 57:38-40 (1994) (Abstract Only—English Translation).
Bellanti, et al. Abnormalities of Th1 function in non-IgE food allergy, celiac disease, and ileal lymphonodular hyperplasia: a new relationship? Ann Allergy Asthma Immunol. Jun. 2003;90(6 Suppl 3):84-9.
Belmonte et al. Fragile X syndrome and autism at the intersection of genetic and neural networks. Nat Neurosci. Oct. 2006; 9(10): 1221-5 (abstract only).
Berg, et al. Section 10.5 Many Enzymes are Activated by Specific Proteolytic Cleavage. 2002.

(56) References Cited

OTHER PUBLICATIONS

Berg, et al. Section 9.1 Proteases: Facilitating a Difficult Reaction. 2002.
Berg, et al. Table of Contents. Biochemistry, 5th edition. 2002.
Bhattacharjee et al., Treatment of Pancreatic Exocrine Insufficiency with Enteric Coated Pancreatin Formulations: An Overview. International Journal of Pharmaceutical Sciences and Nanotechnology. 6(3):2125-2130 (2013).
Birnbaum, et al. Heat shock or stress proteins and their role as autoantigens in multiple sclerosis. Ann N Y Acad Sci. Dec. 19, 1997;835:157-67. Abstract only.
Blackmer. Parkinson disease: treatment and medication. Mar. 10, 2009., retrieved from the internet on Sep. 15, 2009, http://emedicine.medscape.com/article/312519-treatment.
Block, et al. A rapid food screener to assess fat and fruit and vegetable intake. Am J Prev Med. May 2000;18(4):284-8.
Blog. Acid Phosphatase Research (blog). Acid-phosphatase.blogspot.com. 2008.
Bode et al. Usefulness of a simple photometric determination of chymotrypsin activity in stools-results of a multicentre study. Clin Biochem. 1986; 19:333-37.
Boorom. Is this recently characterized gastrointestinal pathogen responsible for rising rates of inflammatory bowel disease (IBD) and IBD associated autism in Europe and the United States in the 1990s? Med Hypotheses. 2007;69(3):652-9.
Borlongan. Recent preclinical evidence advancing cell therapy for Alzheimer's disease. Exp Neurol. Sep. 2012;237(1):142-6. doi: 10.1016/j.expneurol.2012.06.024. Epub Jun. 27, 2012.
Borowitz et al., Study of a novel pancreatic enzyme replacement therapy in pancreatic insufficient subjects with cystic fibrosis J.Pediatr., 149:658-662 (2006).
Borowitz, et al. Use of pancreatic enzyme supplements for patients with cystic fibrosis in the context of fibrosing colonopathy. Consensus Committee. J Pediatr. Nov. 1995;127(5):681-4.
Bouhnik, et al. Lactulose ingestion increases faecal bifidobacterial counts: A randomized double-blind study in healthy humans. European Journal of Clinical Nutrition 58:462-466 (2004).
Bowen. Exocrine secretions of the pancreas. Jul. 5, 2006. Accessed online at www.vivo.colostate.edu/hbooks/pathphys/digestion/pancreas/exocrine.html.
Boyd, et al. Positively charged amino acid residues can act as topogenic determinants in membrane proteins. Proc Natl Acad Sci U S A. Dec. 1989;86(23):9446-50.
Bradstreet, et al. Detection of Measles Virus Genomic RNA in Cerebrospinal Fluid of Children with Regressive Autism: a Report of Three Cases. J. Am Phys Surg. 2004; 9(2):38-45.
Bray, et al. Effect of dietary protein content on weight gain, energy expenditure, and body composition during overeating. A randomized controlled trial. JAMA. Jan. 4, 2012; 307(1):47-55.
Brinkley, et al. Factor analysis of the aberrant behavior checklist in individuals with autism spectrum disorders. J Autism Dev Disord. Nov. 2007;37(10):1949-59. Epub Dec. 21, 2006.
Brown. Background to Parkinson's Disease, biomed.brown.edu. Jul. 14, 2008.
Brudnak et al. Enzyme-based therapy for autism spectrum disorders—is it worth another look? Med Hypoth. 2002; 58:422-428.
Brudnak, Mark et al., Guide to intestinal health in autism spectrum disorder, Kirkman Laboratories, (Oct. 2001).
Bruhat, et al. Amino acid limitation induces expression of CHOP, a CCAAT/enhancer binding protein-related gene, at both transcriptional and post-transcriptional levels. J Biol Chem. Jul. 11, 1997;272(28):17588-93.
Buie, et al. Evaluation, diagnosis, and treatment of gastrointestinal disorders in individuals with ASDs: a consensus report. Pediatrics. Jan. 2010;125 Suppl 1:S1-18.
Button, KS et al. Power failure: why small sample size undermines the reliability of neuroscience. Nat. Rev. Neurosci. 14:365376 (2013).

Calderon-Garciduenas, et al. Immunotoxicity and environment: immunodysregulation and systemic inflammation in children. Toxicol Pathol. 2009;37(2):161-9.
Caldwell, et al. Crystalline Pancreatic Amylase. II. Improved Method for its Preparation from Hog Pancreas Glands and Additional Studies of its Properties. J. Am. Chem. Soc. 1952; 74(16):4033-4035.
Campbell et al. A genetic variant that disrupts MET transcription is associated with autism. Proc Natl Acad Sci USA. 2006; 103(45):16834-16839.
Campbell, et al. Distinct genetic risk based on association of MET in families with cooccurring autism and gastrointestinal conditions. Pediatrics. Mar. 2009;123(3):1018-24.
Carlton. Autism and malnutrition: the milk connection. Retrieved from the internet on Feb. 18, 2008, http://www.mercola.com/2004/autism_malnutrition.htm.
Caronna, et al. Autism spectrum disorders: clinical and research frontiers. Arch Dis Child. Jun. 2008;93(6):518-23.
Carroccio et al. Effectiveness of Enteric-coated Preparations on Nutritional Parameters in Cystic Fibrosis. Digestion 41:201-206 (1988).
Carroccio et al. Role of pancreatic impairment in growth recovery during gluten-free diet in childhood celiac disease. Gastroenterology 112:1839-1844 (1997).
Carroccio, et al. Pancreatic enzyme therapy in childhood celiac disease. A double-blind prospective randomized study. Dig Dis Sci. Dec. 1995;40(12):2555-60.
Carroccio, et al. Secondary impairment of pancreatic function as a cause of severe malabsorption in intestinal giardiasis: a case report. Am J Trap Med Hyg. Jun. 1997;56(6):599-602.
Carroccio, et al. Secretin-cerulein test and fecal chymotrypsin concentration in children with intestinal giardiasis. Int J Pancreatol. Oct. 1993;14(2):175-80.
Cassidy, et al. A new concept for the mechanism of action of chymotrypsin: the role of the low-barrier hydrogen bond. Biochemistry. Apr. 15, 1997;36(15):4576-84.
CDC, *Escherichia coli*, Travelers Health, Chapter 3: Infectious Diseases Related to Travel, Jul. 10, 2015, Available Online at: wwwnc.cdc.gov/travel/yellowbook/2016/infectious-diseases-related-to-travel/escherichia-coli.
CDC. Attention-Deficit/Hyperactivity Disorder (ADHD). Www.cdc.org. 2005.
CDC. Autism Information Center/FAQs. Dept of Health and Human Services/CDC. Jan. 30, 2008.
CDC. High Blood Pressure. Division for Heart Disease Stroke Prevention. Jul. 15, 2003.
Chaignon et al. Susceptibility of staphylococcal biofilms to enzymatic treatments depends on their chemical compositions. Appl. Microbiol. Appl. Microbiol. 75:125-132 (2007).
Chazalette, J.P. et al., A double-bind placebo-controlled trial of a pancreatic enzyme formulation (Panzytrat 25000) in the treatment of impaired lipid digestion in patients with cystic fibrosis. Drug Invest., 5(5):274-280 (1993).
Chen, et al. Identification of two lysosomal membrane glycoproteins. J Cell Biol. Jul. 1985;101(1):85-95.
Chen, et al. Lysine 43 is trimethylated in subunit C from bovine mitochondrial ATP synthase and in storage bodies associated with batten disease. J Biol Chem. May 21, 2004;279(21):21883-7.
Chen, et al. Medicinal Functions of Bromelain and Its Application Prospect in Animal Husbandry, China Animal Husbandry & Veterinary Medicine. 2005; vol. 32, No. 1, p. 14-16. (in Chinese with English translation).
Chez, M. et al. Secretin and autism: A two-part clinical investigation. Journal of Autism and Developmental Disorders, 30(2), 87-94 (Apr. 2000) [Abstract Only].
Childhood Autism Rating Scale (CARS), Wikipedia, downloaded May 5, 2014.
Chung, et al. Effects of a central cholinesterase inhibitor on reducing falls in Parkinson disease. Neurology. Oct. 5, 2010;75(14):1263-9. Epub Sep. 1, 2010.
Cichoke, AJ The Complete Book of Enzyme Therapy, Penguin (1999) pp. 206-208 and 38.

(56) References Cited

OTHER PUBLICATIONS

Cichoke, et al. The complete book of enzyme therapy. Penguin. 1998: 39, 42, 47, 50, and 53.
Cichoke. Celiac disease. The complete book of enzyme therapy. Penguin. New York, NY. 1999; 174-177.
Cichoke. Influenza. In: The Complete Book of Enzyme Therapy. Anthony J. Cichoke. Avery, a member of Penguin Putnam, Inc., publisher. Ed.: Dara Stewart, pp. 37, 40-45 (1999).
Cichoke. Influenza. In: The Complete Book of Enzyme Therapy. D. Stewart, ed. Copyright 1999. Anthony J. Cichoke. Penguin Putnam, Inc., New York, New York. pp. "Contents", 50, 273-275 and 455.
Clark et al., The effect of ranitidine versus proton pump inhibitors on gastric secretions: a meta-analysis of randomized control trials, Anaesthesia, 2009, 64, pp. 652-657.
Claud, et a. Hypothesis: inappropriate colonization of the premature intestine can cause neonatal necrotizing enterocolitis. FASEB J. Jun. 2001;15(8):1398-403.
Commentary on the Japanese Pharmacopoeia, 14th ed., D929-D931, 2001.
Concerta. ADHD Myths and Facts. ADHD Myths and Facts about medication, girls, and symptoms and causes. Concerta.net. Jul. 15, 2008.
Cornish. A balanced approach towards healthy eating in autism, Journal of Human Nutrition and Dietetics 11:501-509 (1998).
Corring, et al. Development of digestive enzymes in the piglet from birth to 8 weeks. I. Pancreas and pancreatic enzymes. NutrMetab. 1978;22(4):231-43.
Couet, et al. Identification of peptide and protein ligands for the caveolin-scaffolding domain. Implications for the interaction of caveolin with caveolae-associated proteins. J Biol Chem. Mar. 7, 1997;272(10):6525-33.
Coutinho, AM et al. Variants of the serotonin transporter gene (SLC6A4) significantly contribute to hyperserotonemia in autism. Mol Psychiatry. Mar. 2004;9(3):264-71.
Cox, RJ et al. Influenza Virus: Immunity and Vaccination Strategies. Comparison of the Immune Response to Inactivated and Live, Attenuated Influenza Vaccines. Scandinavian Journal of Immunology 59, 1-15 (2004).
Coyle. Treating the Negative Symptoms of Schizophrenia: An Expert Interview with Joseph Coyle, MD. www.narsad.org/?q=node/438/latest-research. 2006.
Craig, et al. Heat shock proteins: molecular chaperones of protein biogenesis. Microbiol Rev. Jun. 1993;57(2):402-14.
Creon—FDA Prescribing information side effects and uses. Revised Apr. 2015.
Creon digestive enzymes. Celic.com/ Jun. 2009. http://www.celiac.com/gluten-free/topic/59195-creon-digestive-enzymes.
Creon. Full prescribing information. Last edited Mar. 2013. Abbvie Inc 2012. www.rxabbvie.com/pdf/creon_PI.pdf.
Croonenberghs, et al. Peripheral markers of serotonergic and noradrenergic function in post-pubertal, caucasian males with autistic disorder. Neuropsychopharmacology. Mar. 2000;22(3):275-83.
Cruse et al. Illustrated dictionary of immunology. CRC Press, New York. 1995.
Cuervo, et al. Cathepsin A regulates chaperone-mediated autophagy through cleavage of the lysosomal receptor. EMBO J. Jan. 2, 2003;22(1):47-59.
Curemark press release. Curemark Receives Investigational New Drug Clearance for CM-AT for Autism. Mar. 26, 2009. http://www.medicalnewstoday.com/releases/143723.php.
Curemark Trademark/Service mark application, Principal Register. U.S. Appl. No. 77/527,223. Filing date: Jul. 21, 2008.
Dajcs, et al. Lysostaphin is effective in treating methicillin-resistant *Staphylococcus aureus* Endophthalmitis in the rabbit. Curr Eye Res. Jun. 2001;22(6):451-7.
Daly, E., et al. Response inhibition and serotonin in autism: A functional MRI study using acute tryptophan depletion. Brain, 137(9), 2600-2610 (Sep. 2014).

Darman. An introduction to alternative medicine for psychiatric conditions. Oct. 22, 2007, retrieved on Sep. 18, 2009, http://web.archive.org/web/20071022104238/http://altp[therapies4bipolar.info/ortho/html.
Dawe, et al. Antipsychotic drugs dose-dependently suppress the spontaneous hyperactivity of the chakragati mouse. Neuroscience. Nov. 24, 2010;171(1):162-72. Epub Sep. 17, 2010.
Dawe, et al. The chakragati mouse: a mouse model for rapid in vivo screening of antipsychotic drug candidates. Biotechnol J. Nov. 2007;2(11):1344-52.
Dawn. Autism: the Latest Prevalence Rates in USA—Now 1 in 175. Disabled Women's Network Ontario. Dawn.thot.net/autism2.html. 2006.
Dawson lab. Research Projects in Synthetic Protein Chemistry. 2005; 1-2.
Delong. News on Parkinson's. The Dana Foundation. Jul. 14, 2008.
Derwent. English abstract for RU 2286785 Nov. 10, 2006. Downloaded from the Derwent file Jul. 13, 2011.
Diagnostic and Statistical Manual of Mental Disorders, Fourth Edition, Primary Care Version, Chapter 6, American Psychiatric Association (2000).
Diagnostic and Statistical Manual of Mental Disorders, Fourth Edition, Text Revision, DSM-IV-TR, American Psychiatric Association (2000).
Diaz-Hernandez, et al. Neuronal induction of the immunoproteasome in Huntington's disease. J Neurosci. Dec. 17, 2003;23(37):11653-61.
Digestive Enzyme Preparation: Pancreatin listed in Japanese Pharmacopoeia, Aug. 2008, < URL:http: > (in Japanese with English translation) < /URL:http: >.
Digestive Enzyme Wikipedia. Retrieved from the internet Sep. 10, 2009, http://en.wikipedia.org/wiki/Digestive_enzyme.
Ding, et al. Proteasome inhibition in oxidative stress neurotoxicity: implications for heat shock proteins. J Neurochem. May 2001;77(4):1010-7.
Dobbs et al. Link between helicobacter pylori infection and idiopathic parkinsonism. Medical Hypothesis. 2000; 55(2):93-98.
Dockter et al. Determination of chymotrypsin in the feces by a new photometric method. Padiatr Padol. 1985; 20(3):257-265.
Dominquez-Munoz, et al. Optimising the therapy of exocrine pancreatic insufficiency by the association of a proton pump inhibitor to enteric coated pancreatic extracts. Gut. Jul. 2006;55(7):1056-7.
Drabkin, H., et al. Initiation of protein synthesis in mammalian cells with codons other than AUG and amino acids other than methionine. Molecular and Cellular Biology, 18(9): 5140-5147 (Sep. 1998).
Dudzinska. Dissertation. Development of lipid-based enteric coatings. Oct. 18, 1988. Martin Luther University, Halle-Wittenberg, pp. 1-125.
Dupiereux, et al. Creutzfeldt-Jakob, Parkinson, lewy body dementia and Alzheimer diseases: from diagnosis to therapy. Cent Nerv Syst Agents Med Chem. Mar. 2009;9(1):2-11.
Durie et al. Uses and abuses of enzyme therapy in cystic fibrosis. Journal of the Royal Society of Medicine. 91:(Suppl. 34):2-13 (1998).
Durkin, et al. Socioeconomic inequality in the prevalence of autism spectrum disorder: evidence from a U.S. cross-sectional study. PLoS One. Jul. 1, 20102;5(7):e11551.
Eaves, et al. The criterion-related validity of the Childhood Autism Rating Scale and the Autism Behavior Checklist. J Abnorm Child Psychol. Oct. 1993;21(5):481-91. abstract only.
Edelson, et al. 3-Cyclohexene-1-glycine, an Isoleucine Antagonist. J. Am. Chem. Soc. 1958; 80(11):2698-2700.
Elkashef, et al. Biological markers of cocaine addiction: implications for medications development. Addict Biol. Jun. 2003;8(2):123-39.
Elphick, et al. Impaired luminal processing of human defensin-5 in Crohn's disease: persistence in a complex with chymotrypsinogen and trypsin. Am J Pathol. Mar. 2008;172(3):702-13.
Emc, Creon 10000 Capsules, May 18, 2015, Available Online at: www.medicines.org.uk/emc/medicine/2068.

(56) References Cited

OTHER PUBLICATIONS

EMedExpert, Antibiotics: Cephalosporins, Available online at: http://www.emedexpert.com/compare/ cephalosporins.shtml, available as early as Jun. 2, 2007 per Internet Archive Wayback Machine.

Ethridge, et al. Acute pancreatitis results in induction of heat shock proteins 70 and 27 and heat shock factor-1. Pancreas. Oct. 2000;21(3):248-56.

Evans, C. et al. Altered amino acid excretion in children with autism. Nutritional Neuroscience, 11(1):9-17 (Feb. 2008).

Evans, et al. Pancreatic insufficiency in adult celiac disease: do patients require long-term enzyme supplementation? Dig Dis Sci. Oct. 2010;55(10):2999-3004. doi: 10.1007/s10620-010-1261-y. Epub May 11, 2010.

Exocrine Pancreatic Insufficiency (Enzymes) Document downloaded online on Jan. 8, 2016 at: http://www.epi4dogs.com/enzyme.htm < http: > < /http: >.

Fafournoux, P. et al. Amino acid regulation of gene expression. Biochemical Journal, 351:1-12(2000).

Fairclough, P et al. Comparison of the absorption of two protein hydrolysates and their effects on water and electrolyte movements in the human jejunum. Gut, 21(10):829-834 (1980).

Fallingborg, et al. Measurement of gastrointestinal pH and regional transit times in normal children. J Pediatr Gastroenterol Nutr. Aug. 1990;11(2):211-4.

Fallon. Could one of the most widely prescribed antibiotics amoxicillin/clavulanate "augmentin" be a risk factor for autism? Med Hypotheses. 2005;64(2):312-5.

Family Caregiver Alliance. Fact Sheet: Parkinson's Disease. Caregiver.org. Jul. 14, 2008.

Felig, P. Amino acid metabolism in man. Annual Review of Biochemistry, 44(1):933-955 (1975). [Abstract Only].

Fernell, et al. No evidence for a clear link between active intestinal inflammation and autism based on analyses of faecal calprotectin and rectal nitric oxide. Acta Paediatr. Jul. 2007;96(7):1076-9.

Ferrone, et al. Pancreatic enzyme pharmacotherapy. Pharmacotherapy. 2007; 27:910-920.

Fido, et al. Olanzapine in the treatment of behavioral problems associated with autism: an open-label trial in Kuwait. Med Princ Pract. 2008;17(5):415-8. doi: 10.1159/000141508. Epub Aug. 6, 2008.

Filipek et al. The screening and diagnosis of autistic spectrum disorders. J. of Autism and Dev Disorders. 1999; 29(6).

Final Office Action dated Jan. 3, 2012 for U.S. Appl. No. 10/681,018.
Final Office Action dated Jan. 26, 2012 for U.S. Appl. No. 12/487,864.
Final Office Action dated Nov. 8, 2011 for U.S. Appl. No. 12/054,343.
Final Office Action dated Nov. 8, 2011 for U.S. Appl. No. 12/786,739.
Final Office Action dated Nov. 9, 2010 for U.S. Appl. No. 09/990,909.
Final Office Action dated Feb. 14, 2011 for U.S. Appl. No. 12/049,613.
Final Office Action dated Feb. 27, 2009 for U.S. Appl. No. 11/555,697.
Final Office Action dated Mar. 13, 2009 for U.S. Appl. No. 11/232,180.
Final Office Action dated Mar. 17, 2008 for U.S. Appl. No. 10/681,018.
Final Office Action dated Apr. 28, 2009 for U.S. Appl. No. 10/681,018.
Final Office Action dated May 11, 2010 for U.S. Appl. No. 11/555,697.
Final Office Action dated Jun. 25, 2008 for U.S. Appl. No. 11/213,255.
Final Office Action dated Jul. 2, 2010 for U.S. Appl. No. 12/046,252.
Final Office Action dated Jul. 27, 2004 for U.S. Appl. No. 09/990,909.

Finegold et al. Gastrointestinal microflora studies in late-onset autism. Clinical Infectious Diseases. 2002; 35(1):S6-S15.

First, M. Structured clinical interview for DSM-IV-TR axis I disorders, research version, patient edition. (SCID-I/P) New York: Biometrics Research, New York State Psychiatric Institute. (2002).

Fitzsimmons, et al. High-dose pancreatic-enzyme supplements and fibrosing colonopathy in children with cystic fibrosis. N Engl J Med. May 1, 1997;336(18):1283-9.

Flament, M.P. et al. Development of 400 µm Pellets by Extrusion-Spheronization Application with Gelucire 50/02 to Produce a "Sprinkle" Form, Drug Development and industrial Pharmacy, 30:1,43-51, DOI: 10.1081/DDC-120027510 (2004).

Fliri, et al. Drug effects viewed from a signal transduction network perspective. J Med Chem. Dec. 24, 2009;52(24):8038-46. doi: 10.1021/jm901001p.

Frossard, et al. Both thermal and non-thermal stress protect against caerulein induced pancreatitis and prevent trypsinogen activation in the pancreas. Gut. Jan. 2002;50(1):78-83.

Frossard. Trypsin activation peptide (TAP) in acute pancreatitis: from pathophysiology to clinical usefulness. JOP. Mar. 2001;2(2):69-77.

Furlano, et al. Colonic CD8 and gamma delta T-cell infiltration with epithelial damage in children with autism. J Pediatr. Mar. 2001;138(3):366-72.

Garcia et al. Detection of Giardia lamblia, Entamoeba histolytica/Entamoeba dispar, and Cryptosporidium parvum antigens in human fecal specimens using the triage parasite panel enzyme immunoassay. Am Soc for Microbiology. 2000; 38(9):3337-3340.

Gardner. Absorption of intact peptides: studies on transport of protein digests and dipeptides across rat small intestine in vitro. Q J Exp Physiol. Oct. 1982;67(4):629-37.

Garner Jr, et al. Porcine Pancreatic Lipase—A Glycoprotein. J Biol Chem. Jan. 25, 1972;247(2):561-5.

Gass, et al. Enhancement of dietary protein digestion by conjugated bile acids. Gastroenterology. Jul. 2007;133(1):16-23.

Generation Rescue. Autism and Vaccines Around the World: Vaccine Schedules, Autism Rates, and Under 5 Mortality. Apr. 1, 2009.

German, et al., Apple iPhone Review: Apple iPhone, Jun. 30, 2007; CINET.

Giglio, et al. Failure to thrive: the earliest feature of cystic fibrosis in infants diagnosed by neonatal screening. Acta Paediatr. Nov. 1997;86(11):1162-5.

Girella, E. et al. The assay of chymotrypsin in stool as a simple and effective test of exocrine pancreatic activity in cystic fibrosis. Pancreas, 3(3):254-262 (1988).

GM Chemie 2010 "Products: Hypromellose Phthalate" accessed from www.gmchemie.com on Sep. 22, 2014.

Goff, et al. Production of abnormal proteins in $E.$ $coli$ stimulates transcription of Ion and other heat shock genes. Cell. Jun. 1985;41(2):587-95.

Gonzalez, et al. Endoscopical, histological and immunological characteristics of the digestive mucosa in autistic children with gastrointestinal symptoms. 2005; 1-7.

Green, et al. Amino-terminal polymorphisms of the human beta 2-adrenergic receptor impart distinct agonist-promoted regulatory properties. Biochemistry. Aug. 16, 1994;33(32):9414-9.

Guesnet, P. et al. Docosahexaenoic acid (DHA) and the developing central nervous system (CNS)—Implications for dietary recommendations. Biochimie, 93(1):7-12(2011). [Abstract Only].

Gupta, et al. Analysis of data gaps pertaining to enterotoxigenic $Escherichia$ $coli$ in low and medium human development index countries, 1984-2005. Epidemiol Infect. 2008; 136:721-738.

Gupta, et al. Th1- and Th2-like cytokines in CD4+ and CD8+ T cells in autism. J Neuroimmunol. May 1, 1998 ;85(1):106-9.

Hadjivassiliou, et al. Does cryptic gluten sensitivity play a part in neurological illness? Lancet. Feb. 10, 1996;347(8998):369-71.

Hamel, E. et al. Effects of Cocaine on Rat Pancreatic Enzyme Secretion and Protein Synthesis, Digestive Diseases, 23(3):264-268 (Mar. 1978).

Happe et al. The neuropsychology of autism. Brain. 1996; 119:1377-1400.

Happe et al. Time to give up on a simple explanation for autism. Nat Neurosci. Oct. 2006; 9(10):1218-20.

HEALTH.com. Who is affected by Parkinson's disease, www.health.com. Jul. 14, 2008.

Heijerman, et al. Omeprazole enhances the efficacy of pancreatin (pancrease) in cystic fibrosis. Ann Intern Med. Feb. 1, 1991;114(3):200-1.

Heil, M., et al. Low endogenous fecal chymotrypsin: a possible biomarker for autism. Poster presented at the annual IMFAR Conference on Autism, Atlanta, GA.(May 2014) p. 1.

Hendren et al. Mechanistic biomarkers for autism treatment. Medical Hypotheses. 2009; 73:950-954.

Hitti. New Numbers in ADHD in U.S. Kids (Jul. 15, 2018) WebMD. 2005. 1-2.

(56) References Cited

OTHER PUBLICATIONS

Holquist et al. FDA safety page: Delayed-release vs. extended release Rxs. Drug Topics [online] Jul. 23, 2007 [Retrieved on Jul. 30, 2012] Retrieved from the internet: http://drugtopics.modernmedicine.com/drugtopics/Top+News/FDA-safety-page-Delayed-release-vs-extended-release/ArticleStandard/Article/detail/442606.

Holten, et al. Appropriate prescribing of oral beta-lactam antibiotics. Am Fam Physician. Aug. 1, 2000;62(3):611-20.

Horvath et al. Improved social and language skills after secretin administration in patients with autistic spectrum disorders. Journal of the Association for Academic Minority Physicians. Jan. 1998; 9(1):9-15.

Horvath, et al. Autism and gastrointestinal symptoms. Curr Gastroenterol Rep. Jun. 2002;4(3):251-8.

Horvath, et al. Autistic disorder and gastrointestinal disease. Curr Opin Pediatr. Oct. 2002;14(5):583-7.

Horvath, et al. Gastrointestinal abnormalities in children with autistic disorder. J Pediatr. Nov. 1999;135(5):559-63.

Hoshiko et al. The effect of the gastrointestinal hormones on colonic muscosal blood flow. Acta Medica Nagasakiensia. 1994; 39(4):125-130.

Houston. Autism—One Conference. May 2006. 1-83.

Hsiao, et al. The microbes of the intestine: an introduction to their metabolic and signaling capabilities. Endocrinol Metab Clin North Am. Dec. 2008;37(4):857-71.

Huang, et al. Apoptotic cell death in mouse models of GM2 gangliosidosis and observations on human Tay-Sachs and Sandhoff diseases. Hum Mol Genet. Oct. 1997;6(11):1879-85.

Huang, et al. Mapping of the human APOB gene to chromosome 2p and demonstration of a two-allele restriction fragment length polymorphism. Proc Natl Acad Sci U S A. Feb. 1986;83(3):644-8.

Ijuin, H. Evaluation of pancreatic exocrine function and zinc absorption in alcoholism. The Kurume Medical Journal 45.1 (1998): 1-5.

Information of Papain from Worthington Enzymes webpage http://www.worthington-biochem.com/pap/default.html Downloaded Jan. 17, 2013.

International Application No. PCT/US18/26841 International Search Report and Written Opinion dated Jul. 3, 2018.

International preliminary report on patentability dated Jul. 17, 2014 for PCT/US2013/020183.

International search report and written opinion dated Feb. 21, 2013 for PCT/US2013/020183.

International search report and written opinion dated May 9, 2013 for PCT/US2013/024453.

International search report and written opinion dated Aug. 27, 2013 for PCT/US2013/043444.

International search report and written opinion dated Jan. 18, 2011 for PCT/US2010/057341.

International search report and written opinion dated Nov. 12, 2012 for PCT/US2012/034489.

International search report and written opinion dated Feb. 15, 2011 for PCT/US2010/053484.

International search report and written opinion dated Mar. 2, 2010 for PCT/US2010/020253.

International search report and written opinion dated Mar. 5, 2010 for PCT/US2010/020259.

International search report and written opinion dated Jun. 9, 2010 for PCT/US2010/030895.

International search report and written opinion dated Sep. 25, 2009 for PCT/US2009/049374.

International search report dated Mar. 11, 2002 for PCT/US2001/25343.

International search report dated Jun. 29, 2001 for PCT/US2000/34000.

Isaksson, et al. Pain reduction by an oral pancreatic enzyme preparation in chronic pancreatitis. Digestive Dis. Sci. 1983; 28(2):97-102.

James, et al. Thimerosal neurotoxicity is associated with glutathione depletion: protection with glutathione precursors. Neurotoxicology. 2004; 26(1):1-8.

Jeffrey. Global burden of hypertension may reach 1.5 billion by 2025. Medscape Medical News. Jul. 14, 2008.

Jenkins, et al. Management of gastroenteritis. Archives of Disease in Childhood. 1990; 65:939-941.

Johnson et al. Eating Habits and Dietary Status in Young Children with Autism. J Dev Phys Disabil 20:437-448 (2008).

Juhl. Fibromyalgia and the serotonin pathway. Altern Med Rev. 1998; 3(5):367-375.

Jyonouchi, et al. Dysregulated innate immune responses in young children with autism spectrum disorders: their relationship to gastrointestinal symptoms and dietary intervention. Neuropsychobiology. 2005;51(2):77-85.

Jyonouchi, et al. Evaluation of an association between gastrointestinal symptoms and cytokine production against common dietary proteins in children with autism spectrum disorders. J Pediatr. May 2005;146(5):605-10.

Jyonouchi, et al. Proinflammatory and regulatory cytokine production associated with innate and adaptive immune responses in children with autism spectrum disorders and developmental regression. J Neuroimmunol. Nov. 1, 2001;120(1-2):170-9.

Kachrimanis, et al. Tensile strength and disintegration of tableted silicified microcrystalline cellulose: influences of interparticle bonding. J Pharm Sci. Jul. 2003;92(7):1489-501.

Kaemmerer, et al. Effects of lipid peroxidation-related protein modifications on RPE lysosomal functions and POS phagocytosis. Invest Ophthalmol Vis Sci. Mar. 2007;48(3):1342-7.

Kaminski, et al. Polymorphism of bovine beta-casein and its potential effect on human health. J Appl Genet. 2007;48(3):189-98.

Kaspar et al. New photometric assay for chymotrypsin in stool. Clinical Chemistry. 1984;30(11):1753-1757.

Katritos. New finding may have implications for schizophrenia, autism. Autism/Schizophrenia findings relating to protein, etc. Feb. 10, 2011. e-mail.

Kearney, et al. Global burden of hypertension: analysis of worldwide data. Lancet. Jan. 15-21, 2005;365(9455):217-23. Abstract only.

Keeley et al., Gradual vs. abrupt withdrawal of methylphenidate in two older dependent males. Journal of Substance Abuse Treatment. 2(2):123-125 (1985).

Keller, et al. Pancreatic enzyme supplementation therapy. Current Treatment Options in Gastroenterology 6.5 (2003): 369-374.

Kidd, P.M., Autism, an extreme challenge to integrative medicine. Part 2: medical management. Altern. Med. Rev., 7(6):472-499 (Dec. 2002).

King, et al. Effects of bacterial microflora of the lower digestive tract of free-range waterfowl on influenza virus activation. Appl Environ Microbiol. Jun. 2011;77(12):4119-25. doi: 10.1128/AEM.02578-10. Epub Apr. 29, 2011.
Klopfleisch et al. Encephalitis in a stone marten (*Martes foina*) after natural infection with highly pathogenic avian influenza virus subtype H5N1. Journal of Comparative Pathology 137:155-159 (2007).
Knivsberg, et al. A randomised, controlled study of dietary intervention in autistic syndromes. Nutr Neurosci. Sep. 2002;5(4):251-61.
Koh et al. Inflammation and wound healing: The role of the macrophage. Expert Rev Mol Med. 13:e23 (Author manuscript).
Koivu et al. Determination of Phylloquinone in Vegetables, Fruits, and Berries by High-Performance Liquid Chromatography with Electrochemical Detection. J. Agric. Food Chem. 45(12):4644-4649 (1997).
Kokai-Kun, et al. Lysostaphin as a treatment for systemic *Staphylococcus aureus* infection in a mouse model. J Antimicrob Chemother. Nov. 2007;60(5):1051-9. Epub Sep. 10, 2007.
Koller, et al. Falls and Parkinson's Disease (Abstract). Clin Neuropharmacol. 1989; 12(2):98-105.
Koplin, et al. Soy consumption is not a risk factor for peanut sensitization. J Allergy Clin Immunol. Jun. 2008;121(6):1455-9.

(56) References Cited

OTHER PUBLICATIONS

Koster et al. Evidence based medicine and extradigestive manifestations of helicobacter pylori. Acta Gastro-Enterologica Belgica. 2000; 63(4):388-392.
Krishnaswami, et al. A systematic review of secretin for children with autism spectrum disorders. Pediatrics. May 2011;127(5):e1322-5. doi: 10.1542/peds.2011-0428. Epub Apr. 4, 2011.
Kronenberg, et al. Folate deficiency induces neurodegeneration and brain dysfunction in mice lacking uracil DNA glycosylase. J Neurosci. Jul. 9, 2008;28(28):7219-30.
Kujoth, et al. Mitochondrial DNA mutations, oxidative stress, and apoptosis in mammalian aging. Science. Jul. 15, 2005;309(5733):481-4.
Kumar. Neurologic presentations of nutritional deficiencies. Neurol Clin. Feb. 2010;28(1):107-70.
Larimore. How Common is ADHD? Facts About ADHD. Jul. 15, 2008.
Lashkari, et al. Williams-Beuren Syndrome: An update and review for the primary physician. Clinical Pediatrics. 1999; 38(4):189-208.
Layer et al. Pancreatic enzyme replacement therapy. Current Gastroenterology Reports. 2001; 3:101-108.
Lebenthal, et al. Enzyme therapy for pancreatic insufficiency: present status and future needs. Pancreas. Jan. 1994;9(1):1-12.
Leeds, et al. Is exocrine pancreatic insufficiency in adult coeliac disease a cause of persisting symptoms? Aliment Pharmacol Ther. Feb. 1, 2007;25(3):265-71.
Levy, et al. Relationship of dietary intake to gastrointestinal symptoms in children with autistic spectrum disorders. Biol Psychiatry. Feb. 15, 2007;61(4):492-7.
Leyfer, et al. Comorbid psychiatric disorders in children with autism: interview development and rates of disorders. J Autism Dev Disord. Oct. 2006;36(7):849-61.
Lieberman. Pharmaceutical Dosage Forms. vol. 2: Disperse Systems. New York Marcel Dekker, Inc. 1996; 243-258.
Life Plus Somazyne accessed Jun. 10, 2016, Online at www.lifeplus.com/media/pdf/piSheets/US/ 6141-PI_EN.pdf.
LIPASE 30, Technical Data sheet, 1 page, Scientific Protein Laboratories LLC Jun. 13, 2005.
Liyanage, et al. Bioavailability of iron from micro-encapsulated iron sprinkle supplement. Food and Nutrition bulletin. 2002; 23(3):133-137.
Lloyd. Lysosome membrane permeability: implications for drug delivery. Adv Drug Deliv Rev. Mar. 30, 2000;41(2):189-200.
Lockner et al. Dietary intake and parents' perception of mealtime behaviors in preschool-age children with autism spectrum disorder and in typically developing children. J Am Diet Assoc 108(8):1360-1363 (2008).
Loh, et al. Highly tolerated amino acid substitutions increase the fidelity of *Escherichia coli* DNA polymerase I. J Biol Chem. Apr. 20, 2007;282(16):12201-9.
Lord, et al. Diagnostic Instruments in Autistic Spectrum Disorders, info.med.yale.edu. 2005;11:730-771.
Luedtke, et al. Cathepsin A is expressed in a cell- and region-specific manner in the testis and epididymis and is not regulated by testicular or pituitary factors. J Histochem Cytochem. Aug. 2000;48(8):1131-46.
MacDonald. Thyrotoxicosis treated with pancreatic extract and iodine. Lancet. 1943;244(6251)788.
MacFabe, et al. Neurobiological effects of intraventricular propionic acid in rats: possible role of short chain fatty acids on the pathogenesis and characteristics of autism spectrum disorders. Behav Brain Res. 2006;176(1):149-69.
MacReady. Parkinson's Disease Treatment: what you should know. Retrieved from the internet on Sep. 15, 2009, http://www.everydayhealth.com/parkinsons-disease-treatment-overview.aspx.
Mannino, et al. Surveillance for asthma—United States, 1960-1995. MMWR CDC Surveill Summ. Apr. 24, 1998;47(1):1-27.

Marcus, et al. A placebo-controlled, fixed-dose study of aripiprazole in children and adolescents with irritability associated with autistic disorder. J Am Acad Child Adolesc Psychiatry. Nov. 2009;48(11):1110-19.
Marczewska et al. Protein intake in parkinsonian using the EPIC food frequency questionnaire. Mov Diord. Aug. 2006; 21(8):1229-1231.
Marion et al., A New Procedure Allowing the Complete Removal and Prevention of Hemodialysis. Blood Purification, 23:339-348 (2005).
Marlicz et al. Determination of chymotrypsin in the stool in the diagnosis of chronic pancreatitis. Wiadomosci lekarskie. 1988; 41(11):704-707. (in Polish with English abstract/summary).
Marsh. Neuropsychiatric aspects of Parkinson's disease. Psychosomatics. 2000; 41(1):15-23.
Martin, et al. A rapid and sensitive spectrophotometric method for the assay of chymotrypsin. Biol Chem. Feb. 1959;234(2):294-8.
Matikainen, et al. Autonomic dysfunction in long-standing alcoholism. Alcohol. 1986;21(1):69-73. Abstract only.
Matthews, D. Intestinal absorption of amino acids and peptides. Proceedings of the Nutrition Society, 31(2):171-177(1972).
Maurin, et al. Cellular adaptation to amino acid availability: mechanisms involved in the regulation of gene expression. 2006; 319-326.
Mayo Clinic Staff. Autism. Retrieved from internet Mar. 10, 2008, http://www.mayoclinic.com/health/autism/DS00348DSECTION=2.
Mayo Clinic Staff. Bipolar disorder. Jan. 4, 2008, http://www.mayoclinic.com/health/bipolardisorder/DS00356/DSECTION=symptoms.
Mayo Clinic Staff. Obsessive-compulsive disorder. Dec. 21, 2006. http://www.preferredalternatives.org/lat/WellnessLibrary/anxiety&PanicDisorders/Obsessive-CompulsiveDisorder/Obsessive-CompulsiveDisorder-Mayoclinic.pdf.
Mayo Clinic Staff. Oppositional defiant disorder. Dec. 19, 2007, http://www.mayoclinic.com/health/oppositional-defiant-disorder/DS00630/DSECTION=symptoms.
McAlonan, et al. Brain anatomy and sensorimotor gating in Asperger's syndrome, ain. Jul. 2002;125(Pt 7):1594-606.
McClung, C., et al. Regulation of gene expression and cocaine reward by CREB and DeltaFosB. Nature Neuroscience, 6(11):1208-1215 (2003). [Abstract Only].
McClung, C.A. et al. DeltaFosB: A molecular switch for long-term adaptation in the brain. Molecular Brain Research, 132(2):146-154 (Dec. 20, 2004).
McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.
McCracken, et al. Risperidone in children with autism and serious behavioral problems. N Engl J Med. Aug. 1, 2002 ;347(5):314-21.
Medori et al. Fatal Familial Insomnia, A Prion Disease With a Mutation at Condon 178 of The Prion Protein Case. N Engl J Med 326:444-449 (1992).
Medsafe. Data sheet for alpha-lactose, Jul. 21, 2008, http://www.medsafe.govt.nz/Profs/Datasheet/a/Alphalactulosesyrup.htm.
Medscape. Burden of Hypertension in the United States Greater Than Ever. www.medscape.com. Jul. 14, 2004.
Melmed, et al. Metabolic markers and gastrointestinal symptoms in children with autism and related disorders. J Pediatr Gast Nutr. 2000; 31:S31-S32. Abstract only.
Merck. Autism, Merck manual online medical library home addition, retrieved from the internet Mar. 10, 2008, http://www.mercl.com/mmhge/sec23/ch286/ch286b.html.
Merriam-Webster 2014 "Definition: Precipitate" accessed from www.mirriam-webster.com on Sep. 22, 2014.
MeSH browser. "Child Development Disorders, Pervasive," and "Attention Deficit and Disruptive Behavior Disorders," National Library of medicine. 2001, http://www.nlm.nih.gov/mesh/2002/Mbrowser.html.
Meyer-Lindenberg, et al. Neural mechanisms in Williams syndrome: a unique window to genetic influences on cognition and behavior. Nat. Rev. Neurosci. 2006; 7(5):380-93.

(56) References Cited

OTHER PUBLICATIONS

Michael's Naturopathic Programs, Digestive Enzymes, Product #011161, Accessed on Jun. 10, 2016, online at: www.michaelshealth.com/retail/digestive-enzymes-659.html.
Michell et al. Biomarkers and Parkinson's disease. Brain. 2004; 127(8):1693-1705.
Millipore EMD catalog (online). Papain, unit definition, EMD Millipore Corp, 2013. Downloaded May 13, 2013.
Minamino, et al. Vascular cell senescence: contribution to atherosclerosis. Circ Res. Jan. 5, 2007;100(1):15-26.
Ming, et al. Autism spectrum disorders: concurrent clinical disorders. J Child Neurol. Jan. 2008;23(1):6-13.
Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.
Mitsui, et al. Role of aminopeptidases in the blood pressure regulation. Biological and Pharmaceutical Bulletin of Japan, Pharmaceutical Society of Japan. 2004; 27(6):768-771.
Mizutani, et al. Effects of placental proteases on maternal and fetal blood pressure in normal pregnancy and preeclampsia. Am J Hypertens. Jun. 1996;9(6):591-7.
Mononen, et al. Aspartylglycosaminuria in the Finnish population: identification of two point mutations in the heavy chain of glycoasparaginase. Proc Natl Acad Sci U S A. Apr. 1, 1991;88(7):2941-5.
Moretti, et al. Acute pancreatitis: hypertonic saline increases heat shock proteins 70 and 90 and reduces neutrophil infiltration in lung injury. Pancreas. Jul. 2009;38(5):507-14. Abstract only.
Morimoto, R. The heat shock response: Systems biology of proteotoxic stress in aging and disease. Cold Spring Harbor Symposia on Quantitative Biology, 76:91-99 (2011) (Epub: Feb. 27, 2012).
Mosqueira, et al. Chronic hypoxia impairs muscle function in the *Drosophila* model of Duchenne's muscular dystrophy (DMD). PLoS One. Oct. 20, 2010;5(10):e13450.
Munasinghe et al. Digestive enzyme supplementation for autism spectrum disorders: a double-blind randomized controlled trial. J Autism Dev Disord. Sep. 2010;40(9):1131-8.
Munesue, et al. High prevalence of bipolar disorder comorbidity in adolescents and young adults with high-functioning autism spectrum disorder: a preliminary study of 44 outpatients. Journal of Affective Disorders 111.2-3 (2008): 170-175.
Nachaegari et al. Coprocessed excipients for solid dosage forms. Pharmaceutical Technology. 2004; p. 52, 54, 56 ,58, 60, 64.
Nagamoto. Jacobson: Psychiatric Secrets, 2nd ed. 2001. Ch 28 Antipsychotic meds.
Naushad, Shaik Mohammad et al. Autistic children exhibit distinct plasma amino acid profile. Indian Journal of Biochemistry and Biophysics, 50(5):474-478 (Oct. 2013).
Naver.com entry for Rare Disease Information: Osteopenia—Osteopsathyrosis, Fragilitasossium, Fragilitasossium (accessed Sep. 25, 2019).
Nestler, E.J. Molecular basis of long-term plasticity underlying addiction. Nature Reviews Neuroscience, 2(2):119-128 (Feb. 2001).
Nestler, et al. Delta-FosB: A sustained molecular switch for addiction. PNAS 98(20): 11042-11046 (Sep. 25, 2001).
Neuer, et al. The role of heat shock proteins in reproduction. Hum Reprod Update. Mar.-Apr. 2000;6(2):149-59.
Neumeyer, Ann. M. et al. Brief Report: Bone Fractures in Children and Adults with Autism Spectrum Disorders. J. Autism Dev. Disord. 45(3):881-887 (Mar. 2016).
Nevo et al. Acute immune polyneuropathies: correlations of serum antibodies to Campylobacter jejuni and helicobacter pylori with anti-gm antibodies and clinical patterns of disease. J of Inf Diseases . 1997; 175(S2):S154-6.
Newhorizons. ADD/ADHD: New Perspectives on Attentional Priority Disorders. New Horizons for Learning. Jul. 15, 2008.
NIH, "Celiac Disease", National Digestive Diseases Information Clearinghouse: Bethesda, MD, 2008; 12 pages.
NIH. National Institutes of Health. National Diabetes Statistics 2007. diabetes.niddk.nih.gov. Jun. 1, 2008.
NINDS Guillain-Barre Syndrome Information Page, retrieved from the internet Sep. 15, 2009, http://www.ninds.nih.gov/disorders/gbs/gbs.htm.
NINDS Dysautonomia Information Page, retrieved from the internet Sep. 10, 2009, http://www.ninds.nih.gov/disorders/dysautonomia/dysautonomia.htm.
No Author. RSDSA, 2015: Telltale signs and symptoms of CRPS/RSD on the web at rsds.org/telltale-signs-and-symptoms-of-crpsrsd. [Accessed: Sep. 5, 2018].
Norton, L. et al. Leucine regulates translation initiation of protein synthesis in skeletal muscle after exercise. The Journal of Nutrition, 136(2):533S-537S (Feb. 2006).
Notice of allowance dated Jan. 2, 2014 for U.S. Appl. No. 13/204,881.
Notice of allowance dated Feb. 2, 2015 for U.S. Appl. No. 13/926,822.
Notice of Allowance dated Feb. 17, 2012 for U.S. Appl. No. 10/681,018.
Notice of allowance dated Feb. 20, 2015 for U.S. Appl. No. 12/386,051.
Notice of allowance dated Feb. 27, 2015 for U.S. Appl. No. 14/037,696.
Notice of allowance dated Mar. 1, 2016 for U.S. Appl. No. 14/087,930.
Notice of Allowance dated Mar. 21, 2012 for U.S. Appl. No. 12/487,864.
Notice of allowance dated Apr. 3, 2015 for U.S. Appl. No. 13/737,225.
Notice of allowance dated Apr. 10, 2015 for U.S. Appl. No. 13/144,290.
Notice of allowance dated Apr. 14, 2015 for U.S. Appl. No. 13/144,286.
Notice of Allowance dated Apr. 15, 2011 for U.S. Appl. No. 12/487,868.
Notice of allowance dated Apr. 22, 2016 for U.S. Appl. No. 14/528,715.
Notice of Allowance dated Apr. 29, 2011 for U.S. Appl. No. 12/046,402.
Notice of Allowance dated May 23, 2011 for U.S. Appl. No. 09/990,909.
Notice of Allowance dated May 29, 2013 for U.S. Appl. No. 13/481,087.
Notice of allowance dated Jun. 12, 2014 for U.S. Appl. No. 13/448,061.
Notice of Allowance dated Jun. 27, 2011 for U.S. Appl. No. 12/238,415.
Notice of Allowance dated Jun. 28, 2011 for U.S. Appl. No. 12/487,868.
Notice of Allowance dated Jun. 30, 2011 for U.S. Appl. No. 09/990,909.
Notice of Allowance dated Jul. 3, 2012 for U.S. Appl. No. 13/271,783.
Notice of Allowance dated Jul. 8, 2011 for U.S. Appl. No. 12/046,402.
Notice of Allowance dated Aug. 8, 2011 for U.S. Appl. No. 12/426,794.
Notice of allowance dated Aug. 11, 2014 for U.S. Appl. No. 13/193,346.
Notice of allowance dated Aug. 19, 2013 for U.S. Appl. No. 13/208,963.
Notice of allowance dated Aug. 30, 2013 for U.S. Appl. No. 12/047,818.
Notice of allowance dated Sep. 9, 2015 for U.S. Appl. No. 13/193,346.
Notice of allowance dated Sep. 15, 2014 for U.S. Appl. No. 14/037,652.
Notice of Allowance dated Sep. 20, 2011 for U.S. Appl. No. 12/283,090.
Notice of allowance dated Oct. 29, 2013 for U.S. Appl. No. 13/204,881.
Notice of allowance dated Nov. 16, 2015 for U.S. Appl. No. 14/493,734.
Notice of allowance dated Dec. 23, 2014 for U.S. Appl. No. 14/007,793.
Notice of allowance dated Dec. 23, 2015 for U.S. Appl. No. 12/493,122.
O'Connell. Hypertension Guide, cmbi.bjmu.edu. Jul. 14, 2008.
Office action dated Jan. 12, 2012 for U.S. Appl. No. 12/047,818.
Office action dated Jan. 15, 2014 for U.S. Appl. No. 13/836,135.
Office action dated Jan. 15, 2016 for U.S. Appl. No. 13/502,989.

(56) References Cited

OTHER PUBLICATIONS

Office action dated Jan. 16, 2014 for U.S. Appl. No. 12/046,252.
Office action dated Jan. 16, 2015 for U.S. Appl. No. 12/535,676.
Office action dated Jan. 22, 2013 for U.S. Appl. No. 13/562,999.
Office action dated Jan. 24, 2014 for U.S. Appl. No. 12/054,343.
Office action dated Jan. 24, 2014 for U.S. Appl. No. 12/786,739.
Office action dated Jan. 25, 2013 for U.S. Appl. No. 13/208,963.
Office action dated Jan. 26, 2016 for U.S. Appl. No. 12/054,343.
Office action dated Jan. 29, 2016 for U.S. Appl. No. 12/786,739.
Office Action dated Feb. 1, 2012 for U.S. Appl. No. 12/493,122.
Office action dated Feb. 1, 2016 for U.S. Appl. No. 13/503,844.
Office action dated Feb. 14, 2013 for U.S. Appl. No. 13/193,346.
Office action dated Feb. 14, 2013 for U.S. Appl. No. 13/407,408.
Office action dated Feb. 17, 2016 for U.S. Appl. No. 14/713,178.
Office action dated Feb. 21, 2013 for U.S. Appl. No. 12/047,818.
Office action dated Feb. 26, 2016 for U.S. Appl. No. 12/535,676.
Office action dated Mar. 2, 2016 for U.S. Appl. No. 14/693,711.
Office Action dated Mar. 5, 2012 for U.S. Appl. No. 12/535,676.
Office action dated Mar. 5, 2013 for U.S. Appl. No. 12/493,122.
Office action dated Mar. 6, 2015 for U.S. Appl. No. 13/757,412.
Office action dated Mar. 11, 2014 for U.S. Appl. No. 11/533,818.
Office Action dated Mar. 19, 2012 for U.S. Appl. No. 13/204,881.
Office action dated Mar. 22, 2016 for U.S. Appl. No. 13/733,873.
Office Action dated Mar. 23, 2012 for U.S. Appl. No. 13/271,783.
Office Action dated Mar. 29, 2011 for U.S. Appl. No. 12/054,343.
Office Action dated Mar. 30, 2011 for U.S. Appl. No. 12/786,739.
Office action dated Mar. 30, 2016 for U.S. Appl. No. 14/296,091.
Office action dated Apr. 4, 2016 for U.S. Appl. No. 13/313,629.
Office Action dated Apr. 5, 2012 for U.S. Appl. No. 11/555,697.
Office action dated Apr. 5, 2016 for U.S. Appl. No. 14/713,242.
Office action dated Apr. 6, 2015 for U.S. Appl. No. 14/493,734.
Office action dated Apr. 6, 2016 for U.S. Appl. No. 13/313,708.
Office Action dated Apr. 9, 2012 for U.S. Appl. No. 13/208,963.
Office action dated Apr. 10, 2014 for U.S. Appl. No. 13/502,989.
Office action dated Apr. 13, 2016 for U.S. Appl. No. 14/612,604.
Office action dated Apr. 16, 2014 for U.S. Appl. No. 13/705,763.
Office action dated Apr. 21, 2015 for U.S. Appl. No. 13/660,642.
Office action dated Apr. 21, 2015 for U.S. Appl. No. 14/087,930.
Office action dated Apr. 22, 2015 for U.S. Appl. No. 13/836,135.
Office action dated Apr. 24, 2015 for U.S. Appl. No. 12/786,739.
Office Action dated Apr. 27, 2011 for U.S. Appl. No. 10/681,018.
Office action dated Apr. 27, 2015 for U.S. Appl. No. 12/054,343.
Office Action dated Apr. 28, 2011 for U.S. Appl. No. 12/283,090.
Office action dated May 6, 2015 for U.S. Appl. No. 12/493,122.
Office action dated May 7, 2015 for U.S. Appl. No. 13/705,763.
Office action dated May 9, 2013 for U.S. Appl. No. 13/204,881.
Office action dated May 12, 2014 for U.S. Appl. No. 13/733,873.
Office action dated May 13, 2014 for U.S. Appl. No. 13/313,629.
Office action dated May 15, 2013 for U.S. Appl. No. 13/502,989.
Office action dated May 15, 2014 for U.S. Appl. No. 13/448,061.
Office action dated May 16, 2014 for U.S. Appl. No. 13/313,708.
Office Action dated May 24, 2011 for U.S. Appl. No. 12/487,864.
Office action dated May 27, 2015 for U.S. Appl. No. 13/502,989.
Office action dated Jun. 3, 2015 for U.S. Appl. No. 13/002,136.
Office action dated Jun. 13, 2012 for U.S. Appl. No. 12/493,122.
Office action dated Jun. 17, 2014 for U.S. Appl. No. 13/737,225.
Office action dated Jun. 17, 2014 for U.S. Appl. No. 13/757,412.
Office action dated Jun. 19, 2014 for U.S. Appl. No. 12/386,051.
Office action dated Jun. 25, 2013 for U.S. Appl. No. 13/144,286.
Office action dated Jun. 25, 2013 for U.S. Appl. No. 13/144,290.
Office action dated Jun. 27, 2012 for U.S. Appl. No. 12/493,147.
Office action dated Jun. 27, 2014 for U.S. Appl. No. 14/007,793.
Office action dated Jun. 29, 2011 for U.S. Appl. No. 11/555,697.
Office action dated Jul. 7, 2014 for U.S. Appl. No. 12/535,676.
Office action dated Jul. 11, 2012 for U.S. Appl. No. 12/573,353.
Office action dated Jul. 15, 2013 for U.S. Appl. No. 13/002,136.
Office action dated Jul. 17, 2015 for U.S. Appl. No. 13/733,873.
Office action dated Jul. 18, 2012 for U.S. Appl. No. 12/047,818.
Office action dated Jul. 31, 2013 for U.S. Appl. No. 13/757,412.
Office action dated Aug. 2, 2013 for U.S. Appl. No. 12/535,676.
Office action dated Aug. 7, 2014 for U.S. Appl. No. 13/836,135.
Office action dated Aug. 13, 2012 for U.S. Appl. No. 13/208,963.
Office action dated Aug. 14, 2013 for U.S. Appl. No. 13/448,061.
Office action dated Aug. 28, 2013 for U.S. Appl. No. 13/313,629.
Office action dated Aug. 29, 2014 for U.S. Appl. No. 13/144,286.
Office action dated Aug. 31, 2015 for U.S. Appl. No. 12/535,676.
Office action dated Sep. 8, 2015 for U.S. Appl. No. 11/533,818.
Office action dated Sep. 9, 2013 for U.S. Appl. No. 13/502,989.
Office action dated Sep. 10, 2015 for U.S. Appl. No. 13/313,629.
Office action dated Sep. 11, 2015 for U.S. Appl. No. 13/313,708.
Office action dated Sep. 13, 2012 for U.S. Appl. No. 13/481,087.
Office action dated Sep. 18, 2014 for U.S. Appl. No. 13/502,989.
Office action dated Sep. 19, 2014 for U.S. Appl. No. 11/533,818.
Office action dated Sep. 19, 2014 for U.S. Appl. No. 13/737,225.
Office action dated Sep. 30, 2014 for U.S. Appl. No. 13/144,290.
Office action dated Sep. 30, 2014 for U.S. Appl. No. 13/660,642.
Office Action dated Jan. 21, 2011 for U.S. Appl. No. 12/386,051.
Office Action dated Jan. 29, 2002 for U.S. Appl. No. 09/707,395.
Office Action dated Jan. 8, 2010 for U.S. Appl. No. 10/681,018.
Office action dated Oct. 2, 2014 for U.S. Appl. No. 12/054,343.
Office action dated Oct. 6, 2014 for U.S. Appl. No. 12/493,122.
Office action dated Oct. 9, 2014 for U.S. Appl. No. 12/786,739.
Office Action dated Oct. 1, 2001 for U.S. Appl. No. 09/466,559.
Office action dated Oct. 10, 2012 for U.S. Appl. No. 13/204,881.
Office action dated Oct. 19, 2011 for U.S. Appl. No. 12/386,051.
Office action dated Oct. 24, 2013 for U.S. Appl. No. 13/313,708.
Office action dated Oct. 25, 2012 for U.S. Appl. No. 13/144,286.
Office action dated Oct. 25, 2012 for U.S. Appl. No. 13/144,290.
Office action dated Oct. 30, 2015 for U.S. Appl. No. 14/528,715.
Office Action dated Oct. 5, 2010 for U.S. Appl. No. 12/046,402.
Office action dated Nov. 7, 2014 for U.S. Appl. No. 13/705,763.
Office Action dated Nov. 14, 2007 for U.S. Appl. No. 11/213,255.
Office Action dated Nov. 15, 2010 for U.S. Appl. No. 12/238,415.
Office action dated Nov. 16, 2015 for U.S. Appl. No. 13/705,763.
Office action dated Nov. 19, 2015 for U.S. Appl. No. 14/713,242.
Office action dated Nov. 20, 2015 for U.S. Appl. No. 14/296,091.
Office action dated Nov. 20, 2015 for U.S. Appl. No. 14/612,604.
Office action dated Nov. 21, 2014 for U.S. Appl. No. 13/926,822.
Office Action dated Nov. 25, 2009 for U.S. Appl. No. 11/232,180.
Office Action dated Nov. 26, 2001 for U.S. Appl. No. 09/466,559.
Office action dated Nov. 29, 2013 for U.S. Appl. No. 13/193,346.
Office action dated Dec. 6, 2012 for U.S. Appl. No. 13/002,136.
Office action dated Dec. 10, 2013 for U.S. Appl. No. 13/407,408.
Office action dated Dec. 10, 2015 for U.S. Appl. No. 13/836,135.
Office action dated Dec. 12, 2013 for U.S. Appl. No. 13/144,286.
Office action dated Dec. 13, 2013 for U.S. Appl. No. 12/493,122.
Office action dated Dec. 13, 2013 for U.S. Appl. No. 13/144,290.
Office action dated Dec. 15, 2011 for U.S. Appl. No. 12/493,147.
Office action dated Dec. 15, 2015 for U.S. Appl. No. 14/087,930.
Office action dated Dec. 16, 2013 for U.S. Appl. No. 12/535,676.
Office action dated Dec. 18, 2014 for U.S. Appl. No. 14/037,696.
Office action dated Dec. 18, 2015 for U.S. Appl. No. 14/640,385.
Office Action dated Dec. 19, 2005 for U.S. Appl. No. 10/730,567.
Office action dated Dec. 19, 2014 for U.S. Appl. No. 13/733,873.
Office Action dated Dec. 22, 2006 for U.S. Appl. No. 10/681,018.
Office action dated Dec. 24, 2015 for U.S. Appl. No. 13/757,412.
Office Action dated Mar. 18, 2008 for U.S. Appl. No. 11/468,379.
Office Action dated Mar. 25, 2008 for U.S. Appl. No. 11/213,382.
Office Action dated Mar. 28, 2008 for U.S. Appl. No. 11/555,697.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jun. 30, 2004 for U.S. Appl. No. 10/730,567.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.
Office Action dated Jul. 30, 2002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.

(56) References Cited

OTHER PUBLICATIONS

Office Action dated Aug. 25, 2010 for U.S. Appl. No. 12/487,868.
Office Action dated Aug. 26, 2003 for U.S. Appl. No. 10/041,073.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Sep. 22, 2004 for U.S. Appl. No. 10/730,567.
Office Action dated Sep. 24, 2009 for U.S. Appl. No. 12/046,252.
Office Action dated May 11, 2016 U.S. Appl. No. 14/713,242.
Okahata, et al. Lipid-coated enzymes as efficient catalysts in organic media. Trends in Biotechnology. 1997; 15(2):50-54.
O'Keefe, Stephen J.D. et al. The Exacerbation of Pancreatic Endocrine Dysfunction by Potent Pancreatic Exocrine Supplements in Patients with Chronic Pancreatitis. J. Clin. Gastroenterol. 32(4):319-323 (2001).
Olivar-Parra, et al. Training referential communicative skills to individuals with autism spectrum disorder: a pilot study. Psychological Reports. 2011; 109:921-939.
Owley, et al. Multisite, double-blind, placebo-controlled trial of porcine secretin in autism. J Am Acad Child Adolesc Psychiatry. Nov. 2001;40(11):1293-9.
P.Ya. Grigoryev et al., Reference Guide on Gastroenterology, Moscow, MIA-2003, pp. 454,460,465.
Pancrease. Patient information leaflet. Pancrease HL Capsules. Last updated Apr. 30, 2013. Janssen-cilag LTD. www.medicines.org.uk/EMC/medicine/7326.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Pancreatin 8X USP Powder. Product Specification. Jul. 2000. In: Product Manual. American Laboratories Incorporated. Omaha, NE. p. 1.
Parisi et al. Evaluation of new rapid commercial enzyme immunoassay for detection of Crytosporidium oocysts in untreated stool specimens. J Clin Microbiol. 1995; 33(7):1963-1965.
Park, et al. Increased apoptosis in cystinotic fibroblasts and renal proximal tubule epithelial cells results from cysteinylation of protein kinase Cdelta. J Am Soc Nephrol. Nov. 2006;17(11):3167-75.
Parkinsons Disease Foundation. Parkinson's Disease Q&A. 2007. 1-44.
Parkinsons Disease Foundation. Ten Frequently-Asked Questions about Parkinson's Disease. 2006.
Parracho, et al. Differences between the gut microflora of children with autistic spectrum disorders and that of healthy children. J Med Microbiol. Oct. 2005;54(Pt 10):987-91.
Patel, et al. Formulation and evaluation of mucoadhesive glipizide microspheres. AAPS PharmSciTech. 2005; 6(1):E49-E55.
Patton, J. et al. Factor structure of the Barratt impulsiveness scale. Journal of Clinical Psychology, 51(6): 768-774 (Nov. 1995).
PDTALKS. Motivational & Inspirational Speaking From a Parkinson's Patient Perspective. pdtalks.com/Parkinson_s_Disease.html. Jul. 14, 2008.
Pending U.S. Appl. No. 16/499,988, filed Oct. 1, 2019.
Perman et al. Role of pH in production of hydrogen from carbohydrates by colonic bacterial flora. J Clin Invest. 1981; 24(4):684-685.
Persico, et al. Searching for ways out of the autism maze: genetic, epigenetic and environmental clues. Trends Neurosci. Jul. 2006;29(7):349-58.
Peters et al. Prevalence of enteric parasites in homosexual patients attending an outpatient clinic. J of Clin Micro. 1986; 24(4):684-685.
Peters, et al. Treatment of alcoholic polyneuropathy with vitamin B complex: a randomised controlled trial. Alcohol. Nov.-Dec. 2006;41(6):636-42. Epub Aug. 21, 2006.
Petrolatum: Pharmaceutical Excipients. London: Pharmaceutical Press. 2006. 1-6.
Pisani, et al. Levodopa-induced dyskinesia and striatal signaling pathways. Proc Natl Acad Sci U S A. Mar. 3, 2009;106(9):2973-4. Epub Feb. 26, 2009.

Polanczyk, et al. The worldwide prevalence of ADHD: a systematic review and metaregression analysis. Am J Psychiatry. Jun. 2007;164(6):942-8.
Ponsky, et al. Alterations in gastrointestinal physiology after Roux-en-Y gastric bypass. J Am Coll Surg. Jul. 2005;201(1):125-31.
Preliminary Amendment dated May 18, 2009 for U.S. Appl. No. 12/046,252.
Proesmans, Marijke et al. Omeprazole, a proton pump inhibitor, improves residual steatorrhoea in cystic fibrosis patients treated with high dose pancreatic enzymes. European Journal of Pediatrics 162(11): 760-763 (Nov. 2003).
Puri, et al. Isolated segmental duodenal ganglionosis. Indian Journal of Radiology and Imaging. 2000; 153-154.
Qi, et al. Solubility and emulsifying properties of soy protein isolates modified by pancreatin. Journal of Food Science 62.6 (1997): 1110-1115.
Raimondo, et al. Rapid endoscopic secretin simulation test and discrimination of chronic pancreatitis and pancreatic cancer from disease controls. Clin Gastroenterol Hepatol. Sep. 2003;1(5):397-403.
Rajakumar, et al. Proteasomal activity in placentas from women with preeclampsia and intrauterine growth restriction: implications forexpression of HIF-alpha proteins. Placenta. Mar. 2008;29(3):290-9. Epub Jan. 28, 2008.
Rakonczay, et al. A new severe acute necrotizing pancreatitis model induced by L-ornithine in rats. Crit Care Med. Jul. 2008;36(7):2117-27.
Ray, et al. Growth factor regulation of enterocyte nutrient transport during intestinal adaptation. Am J Surg. Apr. 2002;183(4):361-71.
Reeves, G. et al. Pharmacological Management of Attention-deficit hyperactivity disorder, Expert Opinion on Pharmacotherapy, 5:6; 1313-1320. (Feb. 25, 2005)DOI: 10.1517/14656566.5.6.1313 http://dx.doi.org/10.1517/14656566.5.6.1313.
Regan, et al. Comparative effects of antacids, cimetidine and enteric coating on the therapeutic response to oral enzymes in severe pancreatic insufficiency. N Engl J Med. Oct. 20, 1977;297(16):854-8.
Remtulla et al. Stool chymotrypsin activity measured by a spectrophotometric procedure to identify pancreatic disease in infants. Clinical Biochemistry. Dec. 1986; 19:341-342.
Response dated Jun. 17, 2008 to Advisory Action dated Jun. 3, 2008 for U.S. Appl. No. 10/681,018.
Revolution health. Enzyme therapy, revolutionhealth.com/drugs-treatments/enzyme-therapy. Sep. 2, 2008.
Richards, et al. Diagnosis, management, and treatment of Alzheimer disease: a guide for the internist. Arch Intern Med. Apr. 26, 1999;159(8):789-98.
Rider, et al. Perspective of biochemical research in the neuronal ceroid-lipofuscinosis. Am J Med Genet. Feb. 15, 1992;42(4):519-24.
Riedel, L. et al. Limitations of faecal chymotrypsin as a screening test for chronic pancreatitis. Gut, 32:321-324 (1991).
Rivest, J. et al. A dynamic model of protein digestion in the small intestine of pigs. Journal of Animal Science, 78(2):328-240 (Feb. 2000).
Robinson, T. et al. Incentive-sensitization and addiction. Addiction, 96(1):103-114 (Jan. 2001).
Rogers. No more heartburn: Stop the pain in 30 days—naturally. 2000; 172.
Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.
Roxas, et al. Colds and influenza: a review of diagnosis and conventional, botanical, and nutritional considerations. Alternative Medicine Review. 2007; 12(1):25-48.
Rubenstein, et al. Model of autism: increased ratio of excitation/inhibition in key neural systems. Genes Brain Behav. Oct. 2003;2(5):255-67.
Rudell, et al. The anterior piriform cortex is sufficient for detecting depletion of an indispensable amino acid, showing independent cortical sensory function. J Neurosci. Feb. 2, 2011;31(5):1583-90. Abstract only.

(56) References Cited

OTHER PUBLICATIONS

Sabra, et al. Linkage of ileal-lymphoid-nodular hyperplasia (ILNH), food allergy and CNS developmental: evidence for a non-IgE association. Ann Aller Asth Immunol. 1999; 82(1):81. Abstract only.

Sahelian. Enzymes, raysahelian.com/enzymes.html. Sep. 2, 2008.

Salpekar, et al. Bipolar Spectrum Disorder Comorbid With Autism Spectrum Disorder; NADD Bulletin, vol. X, 2007. No. 6, Article 1, pp. 1-5, downloaded from http://www.thenadd.org/nadd-bulletin/archive/volunne-x/ on Dec. 11, 2018.

Sandler et al. Short term benefit from oral vancomycin treatment of regressive-onset autism. J of Child Neuro. 2000; 15(7):42-435.

Sandler, et al. Lack of benefit of a single dose of synthetic human secretin in the treatment of autism and pervasive developmental disorder. N Engl J Med. Dec. 9, 1999;341(24):1801-6.

Schafer, et al. Stress kinases and heat shock proteins in the pancreas: possible roles in normal function and disease. J Gastroenterol. 2000;35(1):1-9.

Schain, RJ et al. Studies on 5-hydroxyindole metabolism in autistic and other mentally retarded children. J. Pediatr. 58:315-320 (1961) [Summary Only].

Schedl, H. et al. Absorption of I-methionine from the human small intestine. Journal of Clinical Investigation, 47(2): 417-425 (1968).

Schiller. Review article: the therapy of constipation. Aliment Pharmacol Ther. 2001; 15:749-763.

Schizophreniform disorder. Merck Manuals Online Medical Library. Nov. 2005. (in Japanese with English translation).

Schneider, et al. Oral human immunoglobulin for children with autism and gastrointestinal dysfunction: a prospective, open-label study. J Autism Dev Disord. Nov. 2006;36(8):1053-64.

Schreck et al. Food preferences and factors influencing food selectivity for children with autism spectrum disorders. Res Develop Disabil. 2006; 27:353-363.

Schumann. Medical, nutritional and technological properties of lactulose. An update. Eur J Nutr. Nov. 2002;41 Suppl 1:I17-25.

Seltzer, et al. The Symptoms of Autism Spectrum Disorders in Adolescence and Adulthood. Journal of Autism and Developmental Disorders. 2003; 33(6):565-581.

Seneca et al. Enhancement of brain l-dopa concentration with a-chymotrypsin. J American Geriatrics Society. 1973; 256-258. Abstract only.

Serna, et al. Pathogenesis and treatment of Shiga toxin-producing *Escherichia coli* infections. Curr Opin Gastroenterol. Jan. 2008;24(1):38-47.

Settembre, et al. A block of autophagy in lysosomal storage disorders. Hum Mol Genet. Jan. 1, 2008;17(1):119-29.

Shadel. Expression and maintenance of mitochondrial DNA: new insights into human disease pathology. Am J Pathol. Jun. 2008;172(6):1445-56.

Shaul. Report to the Chairman and Ranking Minority Member, Subcommittee on Human Rights and Wellness, Committee on Government Reform, House of Representatives. GEO. Jan. 2005. 1-40.

Shelby, et al. Enzymatic debridement with activated whole pancreas. American Journal of Surgery. Oct. 1958; 96(4):545-549.

Sherwood et al. A new class of high-functionality excipients: silicified microcrystalline cellulose. Pharm Tech. 1998; 22(10):78-88.

Sherwood, et al. Activation of trypsinogen in large endocytic vacuoles of pancreatic acinar cells. Proc Natl Acad Sci U S A. Mar. 27, 2007;104(13):5674-9.

Shimabukuro, et al. Medical expenditures for children with an autism spectrum disorder in a privately insured population. J Autism Dev Disord. 2007;38(3):546-52.

Shpacovitch, et al. Protease-activated receptors: novel PARtners in innate immunity. Trends Immunol. Dec. 2007;28(12):541-50.

Shpacovitch, et al. Role of protease-activated receptors in inflammatory responses, innate and adaptive immunity. J Leukoc Biol. Jun. 2008;83(6):1309-22.

Sienaert, et al. Evidence-based treatment strategies for treatment-resistant bipolar depression: a systematic review. Bipolar Disord. Feb. 2013;15(1):61-9. doi: 10.1111/bdi.12026. Epub Nov. 27, 2012.

Sillanaukee, et al. Improved diagnostic classification of alcohol abusers by combining carbohydrate-deficient transferrin and gamma-glutamyltransferase. Clin Chem. Apr. 2001;47(4):681-5.

Simonoff, et al. Psychiatric disorders in children with autism spectrum disorders: prevalence, comorbidity, and associated factors in a population-derived sample. J Am Acad Child Adolesc Psychiatry. Aug. 2008;47(8):921-9.

Singh, et al. Plasma increase of interleukin-12 and interferon-gamma. Pathological significance in autism. J Neuroimmunol. May 1996;66(1-2):143-5.

Singh, Manjit. Alcoholic pancreatitis in rats fed ethanol in a nutritionally adequate liquid diet. International Journal of Pancreatology, 2:311-324 (1987).

Skeels et al. Crytosporidium infection in Oregon public health clinic patients 1985-88: the value of statewide laboratory surveillance. AJPH. 1990; 80(3):305-308.

Skinner, et al. Treatment of Prion Disease with Heterologous Prion Proteins. PLoS One. Jul. 2, 2015;10(7):e0131993. doi: 10.1371/journal.pone.0131993. eCollection 2015.

Smith, et al. Fecal chymotrypsin and trypsin determinations. Canadian Medical Association Journal. 1971; 104(8):691-4 and 697.

Sousa, et al. Polymorphisms in leucine-rich repeat genes are associated with autism spectrum disorder susceptibility in populations of European ancestry. Mol Autism. Mar. 25, 2010;1(1):7.

Statemaster. Number of Children with Autism (most recent w/graph) by state. Statemaster.com Jul. 14, 2008.

Statemaster. Number of Children with Autism (most recent) by state. Statemaster.com Jul. 14, 2008.

Statemaster. Number of Children with Autism (per capita)(most recent) by state. Statemaster.com Jul. 14, 2008.

Stein, et al. Nitrogen metabolism in normal and hyperkinetic boys. Am J Clin Nutr. Apr. 1984;39(4):520-4.

Steinherz, et al. Patterns of amino acid efflux from isolated normal and cystinotic human leucocyte lysosomes. J Biol Chem. Jun. 10, 1982;257(11):6041-9.

Sternby, et al. Carboxyl Ester Lipase (Bile Salt-Stimulated Lipase), Colipase, Lipase, and Phospholipase A2 Levels in Pancreatic Enzyme Supplements, 1997, Scandinavian Journal of Gastroenterology 32(3): 261-267.

Stoll, et al. Enteral nutrient intake level determines intestinal protein synthesis and accretion rates in neonatal pigs. Am J Physiol Gastrointest Liver Physiol. Aug. 2000;279(2):G288-94.

Stott, et al. MMR and Autism in Perspective: the Denmark Story. J. Am Phys Surg. 2004; 9(3):89-91.

Strader, et al. Structural basis of ß-adrenergic receptor function. FASEB J. May 1989;3(7):1825-32.

Sturmey. Secretin is an ineffective treatment for pervasive developmental disabilities: a review of 15 double-blind randomized controlled trials. Res Dev Disabil. Jan.-Feb. 2005;26(1):87-97.

Sundstrom, et al. A deadly prion disease: fatal familial insomnia. J Neurosci Nurs. Dec. 2003;35(6):300-5. Abstract only.

Swayne, et al. Pathobiology of H5N2 Mexican avian influenza virus infections of chickens. Vet Pathol. Nov. 1997;34(6):557-67.

Tager-Flusberg, et al. Language disorders: autism and other pervasive developmental disorders. Pediatr Clin North Am. Jun. 2007;54(3):469-81, vi.

Tamaro. Vitamin K deficiency as a cause of autistic symptoms. Http://web.archive.org/web/20090612022246/http://www.gutresearch.com/VitaminK.pdf. Published Jun. 12, 2009 as per Wayback Engine.

Tang, G. et al. Loss of mTOR-dependent macroautophagy causes autistic-like synaptic pruning deficits. Neuron, 83(5):1131-1143 (Sep. 3, 2014).

Terrie, et al. Understanding Pancreatic Enzyme Products. Dec. 15, 2008.

The Alzheimer's Association. Basics of Alzheimer's Disease. 2005, 32 pages. http://www.alz.org/national/documents/brochure_Basicsofalz_low/pdf.

Thefreedictionary. Term Sprinkles. Www.thefreedictionary.com. Accessed Nov. 2, 2011. 1 page.

(56) References Cited

OTHER PUBLICATIONS

Therapeutic research center. Approved Pancreatic Enzyme Products. Pharmacist's Letter/Prescriber's Letter 2010. Oct. 2010. 1-3.
Thomas, et al. Defective protein folding as a basis of human disease. Trends Biochem Sci. Nov. 1995;20(11):456-9.
Tiedermann, et al. Identification of a potent natural triterpenoid inhibitor of proteosome chymotrypsin-like activity and NF-kappaB with antimyeloma activity in vitro and in vivo. Blood. Apr. 23, 2009;113(17):4027-37.
Torrente, et al. Focal-enhanced gastritis in regressive autism with features distinct from Crohn's and Helicobacter pylori gastritis. Am J Gastroenterol. Apr. 2004;99(4):598-605.
Torrente, et al. Small intestinal enteropathy with epithelial IgG and complement deposition in children with regressive autism. Mol Psychiatry. 2002;7(4):375-82, 334.
Tran, et al. Treatment of complex regional pain syndrome: a review of the evidence. Can J Anaesth. Feb. 2010;57(2):149-66.
Trauner, et al. Specific cognitive deficits in young children with cystinosis: evidence for an early effect of the cystinosin gene on neural function. J Pediatr. Aug. 2007;151(2):192-6.
Troy. Pancreatic Enzymes. Remington: The Science and Practice of Pharmacy, 21st edition. Lippincot Williams & Wilkins, 2006. p. 1304.
Tsan, et al. Heat shock proteins and immune system. J Leukoc Biol. Jun. 2009;85(6):905-10.
Tsang et al. Extragastroduodenal conditions associated with Helicobacter pylori infection. Hong Kong Medical Journal. 1999; 5(2):169-174.
Tuohy, K.M et al. Using probiotics and prebiotics to improve gut health. Reviews, Therapeutic Focus, DDT 8(15) Aug. 2003.
U.S. Appl. No. 11/533,818 Final Office Action dated Jun. 7, 2016.
U.S. Appl. No. 12/054,343 Final Office Action dated May 10, 2017.
U.S. Appl. No. 12/054,343 Non-Final Office Action dated Dec. 26, 2017.
U.S. Appl. No. 12/054,343 Office Action dated Aug. 19, 2016.
U.S. Appl. No. 12/535,676 Non-Final Office Action dated Apr. 21, 2017.
U.S. Appl. No. 12/535,676 Non-Final Office Action dated Sep. 6, 2018.
U.S. Appl. No. 12/535,676 Office Action dated Sep. 13, 2016.
U.S. Appl. No. 12/786,739 Final Office Action dated Jun. 23, 2017.
U.S. Appl. No. 12/786,739 Final Office Action dated Sep. 25, 2018.
U.S. Appl. No. 12/786,739 Non-Final Office Action dated Jan. 4, 2018.
U.S. Appl. No. 12/786,739 Office Action dated Sep. 20, 2016.
U.S. Appl. No. 13/002,136 Advisory Office Action dated Jul. 9, 2018.
U.S. Appl. No. 13/002,136 Final Office Action dated Jan. 8, 2018.
U.S. Appl. No. 13/002,136 Final Office Action dated Jun. 24, 2016.
U.S. Appl. No. 13/002,136 Non-Final Office Action dated Dec. 18, 2018.
U.S. Appl. No. 13/002,136 Non-Final Office Action dated Feb. 27, 2017.
U.S. Appl. No. 13/193,346 Notice of Allowability dated Jul. 14, 2016.
U.S. Appl. No. 13/193,346 Notice of Allowability dated Jun. 2, 2016.
U.S. Appl. No. 13/313,629 Notice of Allowance dated Dec. 22, 2016.
U.S. Appl. No. 13/313,708 Notice of Allowance dated Dec. 15, 2016.
U.S. Appl. No. 13/502,989 Notice of Allowance dated Aug. 10, 2016.
U.S. Appl. No. 13/503,844 Final Office Action dated Nov. 30, 2017.
U.S. Appl. No. 13/503,844 Office Action dated Aug. 25, 2016.
U.S. Appl. No. 13/503,844 Office Action dated Mar. 27, 2017.
U.S. Appl. No. 13/705,763 Final Office Action dated May 24, 2016.
U.S. Appl. No. 13/733,873 Final Office Action dated Feb. 21, 2018.
U.S. Appl. No. 13/733,873 Non-Final Office Action dated May 25, 2017.
U.S. Appl. No. 13/757,412 Final Office Action dated Jun. 30, 2016.
U.S. Appl. No. 13/757,412 Final Office Action dated Sep. 12, 2017.
U.S. Appl. No. 13/757,412 Office Action dated Apr. 16, 2019.
U.S. Appl. No. 13/757,412 Office Action dated Feb. 10, 2017.
U.S. Appl. No. 13/836,135 Final Office Action dated Dec. 14, 2018.
U.S. Appl. No. 13/836,135 Final Office Action dated May 15, 2017.
U.S. Appl. No. 13/836,135 Non-Final Office Action dated Mar. 15, 2018.
U.S. Appl. No. 13/836,135 Notice of Allowance dated Apr. 25, 2019.
U.S. Appl. No. 13/836,135 Office Action dated Jul. 22, 2016.
U.S. Appl. No. 14/296,091 Final Office Action dated Aug. 23, 2017.
U.S. Appl. No. 14/296,091 Final Office Action dated Jan. 3, 2017.
U.S. Appl. No. 14/296,091 Final Office Action dated Oct. 1, 2018.
U.S. Appl. No. 14/296,091 Non-Final Office Action dated Mar. 22, 2018.
U.S. Appl. No. 14/612,580 Final Office Action dated Aug. 10, 2017.
U.S. Appl. No. 14/612,580 Notice of Allowability dated Mar. 1, 2018.
U.S. Appl. No. 14/612,580 Notice of Allowance dated Jan. 12, 2018.
U.S. Appl. No. 14/612,580 Office Action dated Sep. 21, 2016.
U.S. Appl. No. 14/612,604 Notice of Allowance dated Jul. 20, 2016.
U.S. Appl. No. 14/639,425 Notice of Allowance dated Mar. 10, 2017.
U.S. Appl. No. 14/639,425 Office Action dated Jul. 14, 2016.
U.S. Appl. No. 14/640,385 Supplemental Notice of Allowability dated May 26, 2016.
U.S. Appl. No. 14/693,711 Final Office Action dated Dec. 15, 2016.
U.S. Appl. No. 14/693,711 Notice of Allowability dated May 26, 2017.
U.S. Appl. No. 14/693,711 Notice of Allowance dated Apr. 21, 2017.
U.S. Appl. No. 14/713,178 Advisory Office Action dated Jan. 19, 2017.
U.S. Appl. No. 14/713,178 Final Office Action dated Oct. 14, 2016.
U.S. Appl. No. 14/713,178 Notice of Allowance dated Apr. 12, 2017.
U.S. Appl. No. 14/713,221 Final Office Action dated Jun. 16, 2016.
U.S. Appl. No. 14/713,221 Non-Final Office Action dated Dec. 30, 2016.
U.S. Appl. No. 14/713,221 Notice of Allowance dated Oct. 19, 2017.
U.S. Appl. No. 14/713,242 Final Office Action dated Jan. 9, 2019.
U.S. Appl. No. 14/713,242 Final Office Action dated Jul. 21, 2017.
U.S. Appl. No. 14/713,242 Non-Final Office Action dated Mar. 29, 2018.
U.S. Appl. No. 14/713,242 Office Action dated Dec. 7, 2016.
U.S. Appl. No. 14/921,896 Final Office Action dated Jan. 25, 2018.
U.S. Appl. No. 14/921,896 Notice of Allowability dated Sep. 12, 2018.
U.S. Appl. No. 14/921,896 Notice of Allowance dated Jul. 18, 2018.
U.S. Appl. No. 14/921,896 Office Action dated Apr. 26, 2017.
U.S. Appl. No. 15/089,842 Final Office Action dated Dec. 4, 2018.
U.S. Appl. No. 15/089,842 Non-Final Office Action dated Jun. 26, 2018.
U.S. Appl. No. 15/089,842 Office Action dated Dec. 8, 2017.
U.S. Appl. No. 15/164,493 Non-Final Office Action dated Feb. 27, 2018.
U.S. Appl. No. 15/164,493 Notice of Allowance dated Nov. 15, 2018.
U.S. Appl. No. 15/185,511 Notice of Allowance dated Nov. 16, 2017.
U.S. Appl. No. 15/265,415 Non-Final Office Action dated Apr. 11, 2018.
U.S. Appl. No. 15/265,620 Non-Final Office Action dated Jan. 22, 2019.
U.S. Appl. No. 15/265,620 Non-Final Office Action dated Jun. 20, 2018.
U.S. Appl. No. 15/354,940 Non-Final Office Action dated Nov. 2, 2018.
U.S. Appl. No. 15/593,121 Non-Final Office Action dated Mar. 8, 2018.
U.S. Appl. No. 15/593,129 Office Action dated Jan. 3, 2019.
U.S. Appl. No. 12/786,739 Office Action dated May 8, 2019.

(56) References Cited

OTHER PUBLICATIONS

U.S. Appl. No. 13/733,873 Office Action dated May 16, 2019.
U.S. Appl. No. 15/074,115 Office Action dated Mar. 6, 2019.
U.S. Appl. No. 15/265,415 Notice of Allowance dated Dec. 26, 2018.
U.S. Appl. No. 15/354,940 Final Office Action date Aug. 21, 2019.
U.S. Appl. No. 15/593,121 Notice of Allowance dated Dec. 26, 2018.
U.S. Appl. No. 15/840,883 Office Action dated Aug. 8, 2019.
U.S. Appl. No. 12/535,676 Office Action dated Jun. 26, 2019.
U.S. Appl. No. 13/002,136 Office Action dated Jun. 21, 2019.
U.S. Appl. No. 14/612,580 Office Action dated Dec. 24, 2015.
U.S. Appl. No. 15/089,842 Notice of Allowance dated Mar. 29, 2019.
Uhlmann, et al. Potential viral pathogenic mechanism for new variant inflammatory bowel disease. Mol Pathol. Apr. 2002;55(2):84-90.
ULTRESA—FDA Prescribing Information Side Effects and Uses. Revised Sep. 2014.
ULTRESA. Highlights of prescribing information. Aptalis Pharma US Inc. Revised Mar. 2012.
Unis, et al. A randomized, double-blind, placebo-controlled trial of porcine versus synthetic secretin for reducing symptoms of autism. J Am Acad Child Adolesc Psychiatry. Nov. 2002;41(11):1315-21.
UPI. Number of autistic Calif, students triples. United Press International. Jul. 12, 2008.
USDA. FDA Drug Safety Communication: Clostridium difficile-associated diarrhea can be associated with stomach acid drugs known as proton pump inhibitors (PPIs). Safety announcement. Feb. 8, 2012. Accessed Apr. 1, 2013. http://www.fda.gov/drugs/drugsafety/ucm290510.htm.
USP (32)-NF(27) 2009, Pancreatin, V.3, pp. 3194-3195.
Valicenti-McDermott, et al. Frequency of gastrointestinal symptoms in children with autistic spectrum disorders and association with family history of autoimmune disease. J Dev Behav Pediatr. Apr. 2006;27(2 Suppl):S128-36.
Vargas, et al. Neuroglial activation and neuroinflammation in the brain of patients with autism. Ann Neurol. Jan. 2005;57(1):67-81.
Vellard. The enzyme as drug: application of enzymes as pharmaceuticals. Curr Opin Biotechnol. Aug. 2003;14(4):444-50.
Vilanova, et al. Preparative isolation of the two forms of pig pancreatic pro-(carboxypeptidase A) and their monomeric carboxypeptidases A. Biochem J. Aug. 1, 1985;229(3):605-9.
VIOKACE—FDA Prescribing Information, Side Effects and Uses. Revised Mar. 2012.
VIOKACE. Highlights of prescribing information. Aptalis Pharma US Inc. Revised Mar. 2012.
Vojdani, et al. Antibodies against CNS antigens in autism: Possible cross-reaction with dietary proteins and infectious agent antigens. Neuropsychiatric Disorders and Infection. 2004; 19:171-186.
Vojdani, et al. Heat shock protein and gliadin peptide promote development of peptidase antibodies in children with autism and patients with autoimmune disease. Clin Diagn Lab Immunol. May 2004;11(3):515-24.
Vojdani, et al. Immune response to dietary proteins, gliadin and cerebellar peptides in children with autism. Nutr Neurosci. Jun. 2004;7(3):151-61.
Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (Part 1) Dec. 1999;38(12 Suppl):32S-54S.
Volkmar, et al. Practice Parameters for the Assessment and Treatment of Children, Adolescents, and Adults with Autism and other Pervasive Developmental Disorders. American Academy of Child and Adolescent Psychiatry. J Am Acad Child Adolesc Psychiatry. (Part 2) Dec. 1999;38(12):1611-6.
Wakefield, et al. Enterocolitis in children with developmental disorders. Am J Gastroenterol. Sep. 2000;95(9):2285-95.
Wakefield, et al. Ileal-lymphoid-nodular hyperplasia, non-specific colitis, and pervasive developmental disorder in children. Lancet. Feb. 28, 1998;351(9103):637-41.
Wakefield, et al. Review article: the concept of entero-colonic encephalopathy, autism and opioid receptor ligands. Aliment Pharmacol Ther. Apr. 2002;16(4):663-74.
Wakefield, et al. The significance of ileo-colonic lymphoid nodular hyperplasia in children with autistic spectrum disorder. Eur J Gastroenterol Hepatol. Aug. 2005;17(8):827-36.
Wakefield. Autistic enterocolitis: is it a histopathological entity? Histopathology. 2006; 1-5.
Wakefield. Enterocolitis, Autism, and Measles Virus. Consensus in Child Neurology: Biological Bases and Clinical Perspectives in Autism. 2002; 74-81.
Wakefield. The gut-brain axis in childhood developmental disorders. J Pediatr Gastroenterol Nutr. May-Jun. 2002;34 Suppl 1:S14-7.
Walsh, et al. Heat shock and the role of the HSPs during neural plate induction in early mammalian CNS and brain development. Cell Mol Life Sci. Feb. 1997;53(2):198-211.
Walsh, et al. Reduced violent behavior following chemical therapy. Physiology and behavior. 2004; 82:835-839.
Wang, et al. Activation of Ras/Erk pathway by a novel MET-interacting protein RanBPM. J Biol Chem. Sep. 27, 2002;277(39):36216-22.
Wang, et al. Effect of chymotrypsin C and related proteins on pancreatic cancer cell migration. Acta Biochim Biophys Sin (Shanghai). May 2011;43(5):362-71. Epub Apr. 2, 2011. Jan. 7, 2011. Abstract only.
We Move, PD Workbook, The WEMOVE Clinician's Guide to Parkinson's Disease, 2006.
Weintraub, et al. Morphometric studies of pancreatic acinar granule formation in NCTR-Balb/c mice. J Cell Sci. May 1992;102 ( Pt 1):141 -7.
Welch, et al. Brain effects of chronic IBD in areas abnormal in autism and treatment by single neuropeptides secretin and oxytocin. J Mol Neurosci. 2004;25(3):259-74.
Wender et al. Prevalence of attention deficit disorder, residual type, and other psychiatric disorders in patients with irritable colon syndrome. Am J Psychiatry. 1983; 140(12):1579-82 Abstract only.
Whitehouse. Fact Sheet: Combating Autism Act of 2006. www.whitehouse.gov. Dec. 19, 2006.
Williams, et al. Eating habits of children with autism. Pediatr Nurs. May-Jun. 2000;26(3):259-64.
Williams, et al. Intravenous secretin for autism spectrum disorders (ASD). Cochrane Database Syst Rev. Apr. 18, 2012;4:CD003495. doi: 10.1002/14651858.CD003495.pub3.
Williams, K. et al. Cochrane Review: Selective serotonin reuptake inhibitors (SSRIs) for autism spectrum disorders (ASD). Evidence-Based Child Health: A Cochrane Review Journal, 6(4):1044-1078 (Jul. 2011). [Abstract Only].
Wisniewski, et al. Therapeutic approaches for prion and Alzheimer's diseases. FEBS J. Aug. 2007;274(15):3784-98. Epub Jul. 6, 2007.
Witmer. ADD and ADHD Statistics—CDC Report Looks at Attention-Deficit/Hyperactivity Disorder. About.com—Parenting of Adolescents. Jul. 15, 2008.
Wohlman et al. Enhancement of drug activity by chymotrypsin, penicillin penetration into granulomatous lesions and inflammatory fluids. Cellular and Molecular Life Sciences. 1969; 25(9):953-954.
Wolfson, D., Making sense of digestive enzymes, Klaire Labs, Mar. 13, 2006.
Woodward et al. Ischaemic enterocolitis complicating aidiopathic dysautonomia. Gut. 1998; 43:285-287.
Xu. Pancreatin therapy in chronic pancreatitis. Clin J Dig, May 2005; 25(5):313-315. (in Chinese with English translation).
YAHOO!.com. Who is affected by Parkinson's disease. Yahoo! Health. Jul. 14, 2008.
Yang, et al. Polymeric Porous Framework of a Bismuth Citrate-Based Complex: A Potential Vehicle for Drug Delivery. Medical News Today. Dec. 17, 2010. 1-4.
Yang, Xinyi et al. Advances in anti-staphylococcal agent lysostaphin. Chinese Journal of New Drugs 14(9):1113-1117 (2005).

(56) References Cited

OTHER PUBLICATIONS

Yazbak. Autism in the United States: a perspective. Journal of American Physicians and Surgeons. 2003;8:103-107.
Youngberg, et al. Comparison of gastrointestinal pH in cystic fibrosis and healthy subjects. Dig Dis Sci. May 1987;32(5):472-80.
Yuan, et al.. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. EMBO J. Sep. 15, 1997;16(18):5483-90.
ZENPEP—FDA Prescribing Information, Side Effects and Uses. Revised Sep. 2014.
ZENPEP. Highlights of prescribing information. Eurand Pharmaceuticals Inc. Revised Jul. 2011.
Zhang et al. Lactulose-mannitol intestinal permeability test in children with diarrhea caused by rotavirus and cryptosporidium. J of Pediatric Gastro & Nutrition. 2000; 31(1):16-21.
Beers et al., The Merck Manual of Diagnosis and Therapy. Eighteenth Edition. Section 15: 1713-1717 (2006).
Beers et al., The Merck Manual of Diagnosis and Therapy. Eighteenth Edition. Section 19: 2308-2313 (2006).
Beers et al., The Merck Manual of Diagnosis and Therapy. Eighteenth Edition. Section 19: 2486-2489 (2006).
Fafournoux, et al. Amino acid regulation of gene expression. Biochem J. Oct. 1, 2000;351(Pt 1):1-12.
Fan et al., Guidelines for Standard Operation of Toxicological Safety Assessment (vol. 1). University of Electronic Science and Technology Press (2009).
Harrison, Bipolar Disorder. Healing Depression Naturally, Twin Streams. Kensington Publishing Corp: 31-32. (2004).
Merriam Webster Dictionary: definition of prevent.
Molinari et al., Fecal chymotrypsin and alastase-1 determination on one single stool collected at random: diagnostic value for exocrine pancreatic status. Clinical Biochemistry 37: 758-763 (2004).
Nater et al., Determinants of the diurnal course of salivary alpha-amylase. Psychoneuroendocrinology 32: 392-401 (2007).
The Diagnostic and Statistical Manual of Mental Disorders (DSM IV), published by the American Psychiatric Association, Fourth Edition, Primary CareVersion, Washington, DC, American Psychiatric Association, (2000).
Thomas, Bipolar Disorder-Balancing Moods by Balancing Nutrients; What Doctors Don't Tell You. 14)7): 1-13(2003).
Types of Fats, Healthwise-Mich Med, pp. 1-2, downloaded from https://www/uofmhealth.org/health-library/aa160619 on Feb. 3, 2021.
U.S. Appl. No. 13/002,136 Final Office Action dated Sep. 11, 2020.
U.S. Appl. No. 13/002,136 Notice of Allowance dated Feb. 24, 2021.
U.S. Appl. No. 13/757,412 Final Office Action dated Dec. 22, 2020.
U.S. Appl. No. 15/840,883 Non-Final Office Action dated Apr. 30, 2021.
U.S. Appl. No. 15/889,917 Non-Final Office Action dated Sep. 3, 2020.
U.S. Appl. No. 15/889,917 Notice of Allowance dated Mar. 29, 2021.
U.S. Appl. No. 16/103,192 Non-Final Office Action dated Feb. 10, 2021.
U.S. Appl. No. 16/103,192 Non-Final Office Action dated Nov. 26, 2021.
U.S. Appl. No. 16/281,908 Notice of Allowance dated Nov. 3, 2020.
U.S. Appl. No. 16/281,937 Non-Final Office Action dated Mar. 17, 2021.
U.S. Appl. No. 16/281,937 Notice of Allowance dated Dec. 2, 2021.
U.S. Appl. No. 16/422,079 Notice of Allowance dated Mar. 3, 2021.
U.S. Appl. No. 16/422,462 Non-Final Office Action dated Jul. 22, 2021.
U.S. Appl. No. 16/884,701 Non-Final Office Action dated Jun. 10, 2021.
Xie, Development and Application of New Traditional Chinese Medicine 2nd Edition. People's Medical Publishing House (2000).

\* cited by examiner

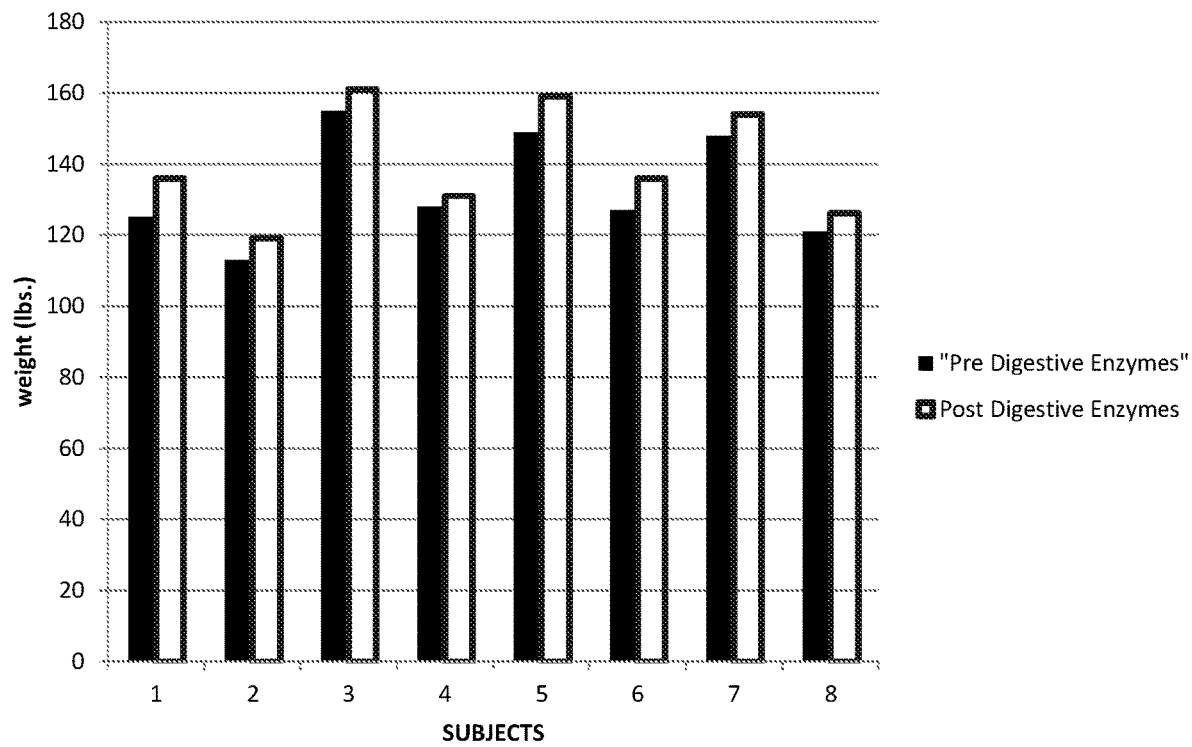

METHODS OF TREATING CELIAC DISEASE

CROSS-REFERENCE

This application is a continuation of U.S. application Ser. No. 13/836,135, filed Mar. 15, 2013, now U.S. Pat. No. 10,350,278, issued Jul. 16, 2019, which claims the benefit of U.S. Provisional Application No. 61/653,253, filed May 30, 2012, which application is incorporated herein by reference in its entirety.

RELATED APPLICATIONS

This application is related to the following Patents and Patents Pending, each of which are fully incorporated herein by reference: U.S. application Ser. No. 09/707,395 filed Nov. 7, 2000, issued on Oct. 14, 2003 as U.S. Pat. No. 6,632,429 B1, entitled "Methods for Treating Pervasive Developmental Disorders"; U.S. application Ser. No. 11/555,697 filed Nov. 2, 2006, entitled "Methods for Treating and Diagnosing Parkinson's Disease and Related Dysautonomic Disorders"; U.S. application Ser. No. 11/533,818 filed on Sep. 21, 2006, entitled "Pharmaceutical Preparations for Attention Deficit Disorder, Attention Deficit Hyperactivity Disorder and Other Associated Disorders"; U.S. application Ser. No. 12/386,051 filed Apr. 13, 2009, entitled "Enzyme Delivery Systems and Methods of Preparation and Use"; U.S. application Ser. No. 12/493,147 filed Jun. 26, 2009, entitled "Methods and Compositions for the Treatment of Symptoms of Complex Regional Pain Syndrome"; International Application No. PCT/US09/49374 filed Jul. 1, 2009, entitled "Methods and Compositions for the Treatment of Symptoms of Neurological and Mental Health Disorders"; U.S. application Ser. No. 12/426,794 filed Apr. 20, 2009, issued on Dec. 27, 2011 as U.S. Pat. No. 8,084,025, entitled "A Method for the Treatment of the Symptoms of Drug and Alcohol Addiction"; U.S. application Ser. No. 12/493,122 filed Jun. 26, 2009, entitled "Methods and Compositions for the Treatment of Symptoms of Williams Syndrome"; U.S. application Ser. No. 11/232,180 filed Sep. 21, 2005, entitled "Combination Enzyme for Cystic Fibrosis"; U.S. Provisional Application No. 61/102,818 filed Oct. 3, 2008, entitled "Pharmaceutical Preparation for the Treatment of Symptoms of Prion Diseases and Method of Making Same"; U.S. Provisional Application No. 61/253,805 filed Oct. 21, 2009, entitled "Methods and Compositions for the Prevention and Treatment of Influenza", and International Application No. PCT/US12/34489 filed Apr. 20, 2012, entitled "Compounds for the Treatment of Neuropsychiatric Disorders".

BACKGROUND OF THE INVENTION

Celiac Disease, also known as sprue, non-tropical sprue, gluten intolerance or gluten-sensitive enteropathy, is a condition that damages the lining of the small intestine and prevents it from absorbing parts of food important for general health. The damage is due to a reaction to eating gluten, which is found in wheat, barley, rye, and possibly oats. Parts of these grains can be found in a whole host of processed foods.

Celiac Disease is both a disease of malabsorption, as nutrients are not absorbed properly, and an abnormal immune reaction to gluten. The exact cause of Celiac Disease is unknown. The lining of the intestines contain areas called villi, which maximize the intestine's ability to absorb nutrients. When people with Celiac Disease eat foods or use products that contain gluten, their immune system reacts by damaging these villi.

Celiac Disease has a strong genetic component associated with the Histocompatibility-Linked-Antigen (HLA) region of the human genome. Environmental factors may also play a role in triggering the disease. People who have a family member with Celiac Disease are at greater risk for developing the disease. Sometimes the disease is triggered or becomes active for the first time after surgery, pregnancy, childbirth, viral infection or severe emotional stress. The disorder is most common in Caucasians and persons of European ancestry with women being typically affected more often than men.

No description in the Background Section should be taken as an admission that such disclosure constitutes prior art to the instant invention.

SUMMARY OF THE INVENTION

The present disclosure provides a method for using digestive enzymes and their derivatives to alleviate the symptoms of Celiac Disease and related disorders. The method comprises administering to the individual a digestive enzyme either naturally or recombinantly derived, or their derivatives, in an amount effective to reduce the symptoms of Celiac Disease. Digestive enzymes generally comprise all proteases, amylases, and lipases, as well as other proteins secreted in a mammal that affect the digestive process either directly or indirectly.

The disorders that present symptoms potentially suitable for alleviation according to a method described herein include, but are not limited to, Celiac Disease, celiac sprue, non-tropical sprue, gluten-sensitive enteropathy, irritable bowel syndrome and chronic fatigue.

Prior to the present application the use of digestive enzymes in the treatment of Celiac Disease has not been elucidated. The use of compositions comprising high doses of digestive enzymes to address the lack of protein digestion experienced by those with Celiac Disease is described herein.

The application of these enzymes of the high protease classification as applied to individuals with Celiac Disease represents a novel discovery for the use of digestive enzymes.

In one aspect, provided herein is a method for treating a subject exhibiting one or more symptoms of Celiac Disease or a related disorder comprising, administering a therapeutically effective amount of a composition comprising digestive enzymes to the individual. In one embodiment, the disorders comprise Celiac Disease, non-tropical sprue, and celiac sprue.

In another embodiment, the symptoms of Celiac Disease which are potentially suited for alleviation are for example, gastrointestinal symptoms, and include, but are not limited to, irritable bowel syndrome, protein deficiency, iron-deficiency anemia caused by menstrual blood loss or protein deficiency, inflammatory bowel disease, diverticulitis, intestinal infections, stool abnormalities, diarrhea which may be protracted or intermittent, constipation, alternating constipation with diarrhea, abdominal pain, bloating, gas or indigestion, decreased appetite (may also be increased or unchanged), lactose intolerance, nausea and vomiting, stools that float, are foul smelling, bloody, or "fatty", and/or unexplained weight loss.

In certain embodiments, the symptoms of celiac and related disorders which are potentially suited for alleviation include, but are not limited to: depression, anxiety, chronic headaches, migraines, fatigue, memory loss, dementia, mania, hypomania, malaise (which may be protracted), seizures, tingling or numbness especially in the extremities and the head, seizures, and irritable and fussy behavior in children.

In another embodiment, the symptoms of celiac and related disorders which are potentially suited for alleviation are those, for example, which represent metabolic, dermatological, immunological or hormonal symptoms and include, but are not limited to, bruising easily, hair loss, mouth ulcers, nosebleeds, missed menstrual periods, Vitamin B12 deficiency, vitamin deficiencies, mineral deficiencies, osteoporosis, delayed growth in children, itchy skin (dermatitis herpetiformis), muscle cramps, joint pain, short stature, poor weight gain, slowed growth, failure to thrive, low cholesterol, pancreatic cancer, lymphoma, gastric cancer, colon cancer and intestinal cancer.

In one embodiment, the digestive enzymes are manufactured using technology selected from the group consisting of enteric coating, lipid encapsulation, direct compression, dry granulation, wet granulation and any combination thereof. In another embodiment, the preparation is administered orally via a dosage formulation selected from the group consisting of pills, tablets, capsules, microcapsules, mini-capsules, time-released capsules, mini-tabs, sprinkles, and any combination thereof. In one embodiment, the total amount of protease ranges per dose from 10,000 to about 1,500,000 U.S.P. units.

Another aspect relates to the method for treating Celiac Disease and related disorders in a subject comprising administering an effective amount of a composition comprising one or more digestive enzymes to the individual. In one embodiment the symptoms of Celiac Disease and related disorders are selected from a group comprising gastrointestinal symptoms and include, but are not limited to, irritable bowel syndrome, protein deficiency, iron-deficiency anemia caused by menstrual blood loss or protein deficiency, inflammatory bowel disease, diverticulitis, intestinal infections, stool abnormalities, diarrhea which may be protracted or intermittent, constipation, alternating constipation with diarrhea, abdominal pain, bloating, gas or indigestion, decreased appetite (may also be increased or unchanged), lactose intolerance, nausea and vomiting, stools that float, are foul smelling, bloody, or "fatty", and unexplained weight loss. In yet another embodiment the symptoms comprise those which are neurological or neuropsychiatric symptoms and include but are not limited to: depression, anxiety, chronic headaches, migraines, fatigue, memory loss, dementia, mania, hypomania, malaise (which may be protracted) seizures, tingling or numbness especially in the extremities and the head, seizures and irritable and fussy behavior in children. In another embodiment, the symptoms are metabolic, dermatological, immunological or hormonal and include, but are not limited to, bruising easily, hair loss, mouth ulcers, nosebleeds, missed menstrual periods, low cholesterol, Vitamin B12 deficiency, vitamin deficiencies, mineral deficiencies, osteoporosis, delayed growth in children, itchy skin (dermatitis herpetiformis), muscle cramps, joint pain, short stature, poor weight gain, slowed growth, failure to thrive, lymphoma, gastric cancer, colon cancer, intestinal cancer and pancreatic cancer.

Provided herein are compositions of digestive enzymes which are useful in the prevention or treatment of one or more symptoms of Celiac Disease or a related disorder. Digestive enzymes generally comprise all proteases, amylases, and lipases, as well as other proteins secreted in a mammal that affect the digestive process either directly or indirectly. Treatment of Celiac Disease or a related disorder encompasses stasis of one or more symptoms (i.e., they do not worsen), as well as reduction (partial or complete) of one or more symptoms. In one embodiment, one or more symptoms of such disorders are reduced in severity or duration by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100%. In another embodiment, one or more symptoms of such disorders are reduced in severity or duration by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold or more. Compositions may include not only one or more digestive enzymes, but also one or more pharmaceutically acceptable carriers, excipients, buffers, fillers, binders, stabilizers, surfactants, diluents, extracts, lubricants, fillers, flavorings, preservatives, colorants, diluents, and coating agents, such as vegetable oil, crystalline oils, taste maskers, etc.

Digestive enzymes to be used in a composition described herein include amylase, lipase, protease, and any combination thereof. In one embodiment, the composition comprising digestive enzyme comprises amylase, lipase and protease. In another embodiment, the composition comprises amylase and lipase. In another embodiment, the composition comprises amylase and protease. In another embodiment, the composition comprises lipase and protease. The enzymes and the amount of each enzyme present in such compositions may be empirically determined by a physician based upon the patient to be treated. In another embodiment, the digestive enzyme is further selected from the group consisting of chymotrypsin, trypsin, pancreatin, papain and any combination thereof. Digestive enzymes may be derived from a source selected from the group consisting of animal enzymes, plant enzymes, synthetic enzymes, recombinant enzymes and any combination thereof. In one embodiment the animal enzyme is derived from a mammal. In another embodiment, the mammal is a pig. In one embodiment, digestive enzymes are derived from a mammalian pancreas. In one embodiment the pancreas is a pig pancreas.

Compositions (preparations) comprising digestive enzymes may be manufactured using any appropriate technology including, but not limited to, enteric coating, lipid encapsulation, direct compression, dry granulation, wet granulation, and any combination thereof. A preparation may be an oral dosage formulation such as, for example, pills, tablets, capsules, microcapsules, mini-capsules, time released capsules, mini-tabs, sprinkles, and any combination thereof. In one embodiment digestive enzymes are provided as a pharmaceutical composition. In one embodiment the pharmaceutical composition is in the form of encapsulated sprinkles. In one embodiment the encapsulation is a lipid coating. In one embodiment the lipid coating is a soy lipid coating.

In one embodiment, the total amount of protease in a composition ranges from about 5,000 to about 1,500,000 U.S.P. units/dose. In another embodiment, the total amount of amylase in a composition ranges from about 1,000 to about 15,000,000 U.S.P. units/dose. In another embodiment, the total amount of lipase in a composition ranges from about 1,500 to about 282,000 U.S.P. units/dose.

In any of such methods, one or more of the formulations described herein may be administered to a subject.

Provided herein is a pharmaceutical composition comprising digestive enzymes for use in the methods described herein, wherein the digestive enzymes comprise about 23,000 U.S.P. units/dose of lipase, about 144,000 U.S.P. units/dose of amylase and about 140,000 U.S.P. units/dose of protease.

Provided herein is a pharmaceutical composition comprising digestive enzymes for use in the methods described herein, wherein the digestive enzymes comprise about 23,040 U.S.P. units/dose of lipase, about 144,000 U.S.P. units/dose of amylase and about 140,400 U.S.P. units/dose of protease.

Provided herein is a pharmaceutical composition comprising digestive enzymes for use in the methods described herein, wherein the digestive enzymes comprise about 16,800 U.S.P. units/dose of lipase, about 70,000 U.S.P. units/dose of protease, and about 70,000 U.S.P. units/dose of amylase.

Provided herein is a pharmaceutical composition comprising digestive enzymes for use in the methods described herein, wherein the digestive enzymes comprise about 16,800 U.S.P. units/dose of lipase, about 110,000 U.S.P. units/dose of protease, and about 70,000 U.S.P. units/dose of amylase.

A dose of a pharmaceutical composition described herein may be formulated for oral administered in an amount of, for example, about 3 teaspoons, about 2.75 teaspoons, about 2.5 teaspoons, about 2.25 teaspoons, about 2 teaspoons, about 1.75 teaspoons, about 1.5 teaspoons, about 1.25 teaspoons, about 1 teaspoon, about ½ teaspoon, about ¼ teaspoon, or about ⅛ teaspoon.

A dose of a composition described herein may be formulated for oral administered in an amount of, for example, about ½ tablet, about 1 tablet, about 1.5 tablets, about 2 tablets, about 2.5 tablets, about 3 tablets, about 3.5 tablets, or about 4 tablets.

Compositions contemplated herein include, but are not limited to, pellets, capsules, caplets, beadlets, sprinkles, tablets, softgels or other carriers.

In one embodiment, a dose of a composition comprises about 8,400 U.S.P. units lipase, 35,000 U.S.P. units protease, and about 35,000 U.S.P. units amylase.

In one embodiment, a dose of a composition comprises about 8,400 U.S.P. units lipase, 35,000 U.S.P. units protease, and about 35,000 U.S.P. units amylase.

In one embodiment, a dose of a composition comprises about 16,800 U.S.P. units Lipase, about 70,000 U.S.P. units Protease, and about 70,000 U.S.P. units Amylase.

In one embodiment, a dose of a composition comprises about 33,600 U.S.P. units Lipase, about 140,000 U.S.P. units Protease, and about 140,000 U.S.P. units Amylase.

In one embodiment, a dose of a composition comprises about 50,400 U.S.P. units Lipase, about 210,000 U.S.P. units Protease, and about 210,000 U.S.P. units Amylase.

In one embodiment, a dose of a composition comprises about 67,200 U.S.P. units Lipase, about 280,000 U.S.P. units Protease, and about 280,000 U.S.P. units Amylase.

In one embodiment, a dose of a composition comprises about 84,000 U.S.P. units Lipase, about 350,000 U.S.P. units Protease, and about 350,000 U.S.P. units Amylase.

In one embodiment, a dose of a composition comprises about 100,800 U.S.P. units Lipase, about 420,000 U.S.P. units Protease, and about 420,000 U.S.P. units Amylase.

In one embodiment, a dose of a composition comprises about 117,600 U.S.P. units Lipase, about 490,000 U.S.P. units Protease, and about 490,000 U.S.P. units Amylase.

In one embodiment, a dose of a composition comprises about 134,400 U.S.P. units Lipase, about 560,000 U.S.P. units Protease, and about 560,000 U.S.P. units Amylase.

In one embodiment, a dose of a composition comprises about 151,200 U.S.P. units Lipase, about 630,000 U.S.P. units Protease, and about 630,000 U.S.P. units Amylase.

In one embodiment, a dose of a composition comprises about 168,000 U.S.P. units Lipase, about 700,000 U.S.P. units Protease, and about 700,000 U.S.P. units Amylase.

In one embodiment, a dose of a composition comprises about 184,800 U.S.P. units Lipase, about 770,000 U.S.P. units Protease, and about 770,000 U.S.P. units Amylase.

In one embodiment, a dose of a composition comprises about 201,600 U.S.P. units Lipase, about 840,000 U.S.P. units Protease, and about 840,000 U.S.P. units Amylase.

In one embodiment, a dose of a composition comprises about 218,400 U.S.P. units Lipase, about 910,000 U.S.P. units Protease, and about 910,000 U.S.P. units Amylase.

In one embodiment, a dose of a composition comprises about 235,200 U.S.P. units Lipase, about 980,000 U.S.P. units Protease, and about 980,000 U.S.P. units Amylase.

In one embodiment, a dose of a composition comprises about 252,000 U.S.P. units Lipase, about 1,050,000 U.S.P. units Protease, and about 1,050,000 U.S.P. units Amylase.

Any of the doses may be optionally supplemented with additional protease. In one embodiment, a dose may be supplemented with about 0 U.S.P. units; about 20,000 U.S.P. units; about 40,000 U.S.P. units; about 60,000 U.S.P. units; about 80,000 U.S.P. units; about 100,000 U.S.P. units; about 120,000 U.S.P. units; about 140,000 U.S.P. units; or about 160,000 U.S.P. units protease.

In one embodiment, a dose of pharmaceutical composition comprises digestive enzymes, wherein the digestive enzymes comprise a dose as set forth in Table 1.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is a graph illustrating increase in weight gain prior to and following administration of enzyme compositions to eight patients with Celiac Disease.

DETAILED DESCRIPTION OF THE INVENTION

The present inventors have identified compositions comprising digestive enzymes which are useful for prevention and/or treatment of Celiac Disease (CD).

Celiac Disease

Celiac Disease affects people in all parts of the world. Originally thought to be a rare childhood syndrome, Celiac Disease is now known to be a common genetic disorder. More than 2 million people in the United States have the disease, or about 1 in 133 people. Among people who have a first-degree relative such as a parent, sibling, or child diagnosed with Celiac Disease, as many as 1 in 22 may have the disease.

Gluten (from Latin gluten "glue") is a protein composite that appears in foods processed from wheat and related species, including barley and rye. It is utilized in the processing of food to give it elasticity, for example with dough, helping it to rise and keep its shape, and often giving the final product a chewy texture. It is used in products that range from foodstuffs to lipsticks and other cosmetics.

Gluten is the composite of a gliadin and a glutelin, which exist conjoined with starch, in the endosperm of various grass-related grains. The prolamin and glutelin from wheat—gliadin, which is alcohol soluble, and glutenin, which is only soluble in dilute acids or alkalis—compose about 80% of the protein contained in wheat seed.

Being insoluble in water, the gliadin and glutelin can be purified by washing away the associated starch. Worldwide, gluten is a source of protein, both in foods prepared directly from sources containing it, and as an additive to foods otherwise low in protein.

The seeds of most flowering plants have endosperms with stored protein to nourish embryonic plants during germination. True gluten, with gliadin and glutenin, is limited to certain members of the grass family. The stored proteins of maize and rice are sometimes called glutens, but their proteins differ from wheat gluten by lacking gliadin.

Gluten is extracted from flour by washing out the starch: starch is water-soluble while gluten is not, and gluten binds together strongly, while starch dissolved in cold water is mobile. If a saline solution is used instead of water, a purer protein is obtained, with certain harmless impurities going into solution with the starch. However, on an industrial scale, starch is the prime product, making cold water the favored solvent.

In home or restaurant cooking, a ball of wheat flour dough is kneaded under water until the starch dissolves out. In industrial production, a slurry of wheat flour is kneaded vigorously by machinery until the starch dissolves and the gluten condenses into a mass. This mass is collected by centrifugation, and then transported through several stages integrated in a continuous process. Approximately 65% of the water in the wet gluten is removed by means of a screw press; the remainder is sprayed through an atomizer nozzle into a drying chamber, where it remains at an elevated temperature a short time to evaporate the water without denaturing the gluten. The process yields a flour-like powder with 7% moisture content, which is air-cooled and pneumatically transported to a receiving vessel. In the final step, the collected gluten is sifted and milled to produce a uniform product.

Recognizing Celiac Disease can be difficult because some of its symptoms are seen in other diseases. Celiac Disease can be often misdiagnosed as irritable bowel syndrome, iron-deficiency anemia caused by menstrual blood loss, inflammatory bowel disease, diverticulitis, intestinal infections, and chronic fatigue syndrome. As a result, Celiac Disease has long been under diagnosed or misdiagnosed.

Abnormalities with stools are the hallmark of the disease. Most individuals experience protracted diarrhea when they have Celiac Disease. However some individuals experience constipation, some have alternating constipation with diarrhea and still others experience very little problems with their stools.

Other gastrointestinal symptoms associated with Celiac Disease include: abdominal pain, bloating, gas, or indigestion, decreased appetite (may also be increased or unchanged), lactose intolerance, nausea and vomiting, stools that float, are foul smelling, bloody, or "fatty", and unexplained weight loss (although people can be overweight or of normal weight). Further symptoms of Celiac Disease may include diarrhea which may be intermittent, an accompanying lactose intolerance, nausea, vomiting which may be intermittent or connected to the ingestion of food, More symptoms may include easy bruising, depression, anxiety, chronic headaches, migraines, fatigue, malaise (which may be protracted), hair loss, mouth ulcers, seizures, muscle cramps, joint pains, tingling or numbness, especially in the extremities and the head, nosebleeds, and missed menstrual periods.

As the intestines in Celiac Disease do not absorb many important vitamins, minerals and other parts of food, the following symptoms may arise over time: bruising easily, depression or anxiety, fatigue, delayed growth in children, hair loss, itchy skin (dermatitis herpetiformis), missed menstrual periods, mouth ulcers, muscle cramps and joint pain, nosebleeds, seizures, tingling or numbness in the hands or feet, unexplained short height and osteoporosis.

Children with Celiac Disease may have defects in the tooth enamel and changes in tooth color, delayed puberty, diarrhea, constipation, fatty or foul-smelling stools, nausea, or vomiting, irritable and fussy behavior, poor weight gain, slowed growth and shorter than normal height for their age and depression.

Individuals with Celiac Disease have higher than normal levels of certain autoantibodies, proteins that react against the body's own cells or tissues in their blood. Diagnosis of Celiac Disease may include blood tests for high levels of anti-tissue transglutaminase antibodies (tTGA) or anti-endomysium antibodies (EMA). If test results are negative but Celiac Disease is still suspected, additional blood tests may be needed. Also an anti-gliadin antibody may be detected in the blood. The following indirect markers may be found in Celiac Disease: low albumin in the blood, high levels of alkaline phosphatase, low cholesterol, abnormal complete blood count, low iron and decreased prothrombin time, as well as other clotting factors.

Dermatitis herpetiformis (DH) is an intensely itchy, blistering skin rash that affects 15 to 25 percent of people with Celiac Disease. The rash usually occurs on the elbows, knees, and buttocks. Most people with DH have no digestive symptoms of Celiac Disease. DH is diagnosed through blood tests and a skin biopsy. If the antibody tests are positive and the skin biopsy has the typical findings of DH, patients do not need to have an intestinal biopsy. Both the skin disease and the intestinal disease respond to a gluten-free diet and recur if gluten is added back into the diet. The rash symptoms can be controlled with immunosuppressants such as dapsone. Because dapsone does not treat the intestinal condition, people with DH must maintain a gluten-free diet.

Up to 30% of patients with Celiac Disease also complain of concomitant chronic headaches or migraines. Systemic inflammatory responses to undigested proteins may lead to the advent of headaches and migraines.

There presently is no cure for Celiac Disease, and multiple attempts to secure a pharmaceutical treatment of any kind have been unsuccessful. The only known treatment heretofore for Celiac Disease is a gluten-free diet. A dietitian is generally employed to help teach the individual with Celiac Disease how to employ the gluten free diet. Individuals with Celiac Disease can learn from a dietitian how to read ingredient lists and identify foods that contain gluten in order to make informed decisions at the grocery store and when eating out.

Following the gluten free diet will stop symptoms, heal existing intestinal damage, and prevent further damage. Improvement begins within days of starting the diet. The small intestine usually heals in 3 to 6 months in children but may take several years in adults. A healed intestine means a person now has villi that can absorb nutrients from food into the bloodstream.

To stay well, people with Celiac Disease must avoid gluten for the rest of their lives. Eating even a small amount of gluten can damage the small intestine. The damage will occur in anyone with the disease, including people without noticeable symptoms. Depending on a person's age at diagnosis, some problems will not improve, such as short stature and dental enamel defects.

Some people with Celiac Disease show no improvement on the gluten-free diet. The most common reason for poor response to the diet is that small amounts of gluten are still being consumed. Hidden sources of gluten include additives such as modified food starch, preservatives, and stabilizers made with wheat. And because many corn and rice products are produced in factories that also manufacture wheat products, they can be contaminated with wheat gluten.

Rarely, the intestinal injury will continue despite a strictly gluten-free diet. People with this condition, known as refractory Celiac Disease, have severely damaged intestines that cannot heal. Because their intestines are not absorbing enough nutrients they may need to receive nutrients directly into their bloodstream through a vein, or intravenously. Researchers are evaluating drug treatments for refractory Celiac Disease.

Diagnosis

Americans are not routinely screened for Celiac Disease. However, because Celiac Disease is hereditary, family members of a person with the disease may wish to be tested. Four to 12 percent of an affected person's first-degree relatives will also have the disease.

Screening for Celiac Disease generally refers to testing for the presence of auto-antibodies in the blood in people without symptoms. There are several tests that can be used to assist in diagnosis including, but not limited to, albumin levels (may be low), alkaline phosphatase levels (high level may be a sign of bone loss), clotting factor abnormalities, cholesterol (may be low), complete blood count (CBC—test for anemia), liver enzymes (transaminases), and prothrombin time. Blood tests can detect several special antibodies, called anti-tissue transglutaminase antibodies (tTGA) or anti-endomysium antibodies (EMA).

If the tests are positive, upper endoscopy is usually performed to sample a piece of tissue (biopsy) from the first part of the small intestine (duodenum). The biopsy may show a flattening of the villi in the parts of the intestine below the duodenum.

The level of symptoms may determine the order of the tests, but tests lose their usefulness if the patient is already taking a gluten-free diet. Intestinal damage begins to heal within weeks of gluten being removed from the diet, and antibody levels decline over months. For those who have already started on a gluten-free diet, it may be necessary to perform a re-challenge with some gluten-containing food in one meal a day over 2-6 weeks before repeating the tests.

High-risk symptoms include, for example, weight loss, anemia (hemoglobin less than 120 g/l in females or less than 130 g/l in males), or diarrhea (more than three loose stools per day).

Serological blood tests may be used to make a diagnosis of Celiac Disease. IgA anti-endomysial antibodies can detect Celiac Disease with a sensitivity and specificity of 90% and 99% according to a systematic review. The systematic review estimates that the prevalence of Celiac Disease in primary care patients with gastrointestinal symptoms to be about 3%. Serology for anti-tTG antibodies was initially reported to have a high sensitivity (99%) and specificity (>90%) for identifying Celiac Disease; however, the systematic review found the two tests were similar. Modern anti-tTG assays rely on a human recombinant protein as an antigen. tTG testing should be done first as it is an easier test to perform. An equivocal result on tTG testing should be followed by antibodies to endomysium.

If the tests are positive, upper endoscopy is usually performed to sample a piece of tissue (biopsy) from the first part of the small intestine (duodenum). The biopsy may show a flattening of the villi in the parts of the intestine below the duodenum. Genetic testing of the blood for specific markers is also available to help determine who may be at risk for Celiac Disease. A follow-up biopsy or blood test may be ordered several months after the diagnosis and treatment. These tests evaluate your response to treatment. Normal results mean that you have responded to treatment, which confirms the diagnosis. However, this does not mean that the disease has been cured.

If blood tests and symptoms suggest Celiac Disease, a biopsy of the small intestine should be performed to confirm the diagnosis. During the biopsy, the doctor removes tiny pieces of tissue from the small intestine to check for damage to the villi. To obtain the tissue sample, an endoscope is used which is inserted through the patient's mouth and stomach into the small intestine. The doctor then takes the samples using instruments passed through the endoscope.

Compositions and Formulations

The invention also relates to a specific blend of enzymes, with or without coating, with or without other components as described above whereby enzyme administration occurs in individuals with Celiac Disease and related disorders, including but not limited to: celiac sprue, non-tropical sprue, gluten-sensitive enteropathy and irritable bowel syndrome.

Digestive enzymes are produced by the salivary glands, glands in the stomach, the pancreas and glands in the small intestines. Digestive enzymes produced by the pancreas are secreted into the duodenum, or upper segment of the small intestine, raising the pH to around 5 or 6, and they assist in the digestion of food components, including carbohydrates, lipids, proteins and nucleic acids.

Pancreatic enzymes administered to humans are commonly of porcine origin. Manufacturers of enzyme preparations for these individuals have used enteric coatings for targeted complete delivery in the distal portion of the small intestine, where lipase activity is important.

Digestive enzymes generally comprise all proteases, amylases and lipases, as well as other proteins secreted in a mammal which affect the digestive process either directly or indirectly.

Digestive enzymes to be used in the compositions and methods described herein include, for example, pancreatic enzymes. There are two types of pancreatic enzymes which have U.S.P. designations: pancreatin and pancrealipase. Pancreatin is a substance containing enzymes, principally amylase, lipase, and protease, obtained from the pancreas of the hog *Sus scrofa* Linne var. *domesticus* Gray (Fam. Suidae) or of the ox *Bos Taurus* Linne (Fam. Bocidae). Pancreatin contains, in each mg, not less than 25 U.S.P. units of amylase activity, not less than 2 U.S.P. units of lipase activity, and not less than 25 U.S.P. of protease activity. More information on Pancreatin is provided in Example 1 below. In contrast, pancrealipase U.S.P. refers to a cream-colored, amorphous powder, having a faint, characteristic (meaty), but not offensive odor, which contains Lipase in an amount of not less than 24 U.S.P. Units/mg; Protease in an amount of not less than 100 U.S.P. Units/mg; and Amylase in an amount of not less than 100 U.S.P. Units/mg; with not more than 5% fat and not more than 5% loss on drying.

In another aspect, this disclosure relates to a pharmaceutical composition comprising a therapeutically effective amount of an enzyme preparation, which comprises a core amount of pancreatic or digestive enzymes effective for treating a subject susceptible to treatment by the enzymes, specifically those suffering with Celiac Disease or a related disorder.

In another aspect, this disclosure relates to a pharmaceutical composition comprising a therapeutically effective amount of an enzyme preparation, which comprises a core amount of pancreatic or digestive enzymes effective for treating a subject susceptible to treatment by the enzymes, specifically those suffering with Celiac Disease and related disorders.

Compositions comprising an effective amount of the compound may be administered via any conventional route including but not limited to oral, parenteral, intramuscular, intravenous, transmuscosal, transdermal, via suppository or other method. Further the oral administration can be in the form of pellets, capsules, caplets, beadlets, sprinkles, tablets, softgels or other carrier. The enzymes may be coated or uncoated.

The composition of the dosage form may include other components, generally utilized in pharmaceutical preparations including but not limited to binders, extracts, lubricants, fillers, flavorings, preservatives, colorants, taste maskers, diluents, and coating agents, such as vegetable oil, crystalline oils, and other coating methodologies.

In one embodiment, the digestive enzymes comprise amylase, lipase, protease, or a combination thereof. In another embodiment, the digestive enzyme is further selected from the group consisting of chymotrypsin, trypsin, pancreatin, papain and any combination thereof. Digestive enzymes may be derived from a source selected from the group consisting of animal enzymes, plant enzymes, synthetic enzymes, recombinant enzymes and any combination thereof. In one embodiment the digestive enzymes are pancreatic digestive enzymes. In one embodiment, the animal enzyme is derived from a mammal. In one embodiment the mammal is a pig. In one embodiment, digestive enzymes are derived from a mammalian pancreas. In one embodiment the pancreas is a pig pancreas.

In yet another embodiment of the present disclosure, digestive enzymes comprise proteases, amylases, and lipases, as well as other proteins secreted in a mammal that affect the digestive process either directly or indirectly. In one embodiment, the digestive or pancreatic enzyme composition comprises one or more of the following: amylases, proteases, cellulase, papaya, bromelain, lipases, chymotrypsin, trypsin, and elastase.

In one embodiment of the present disclosure, digestive enzymes comprise proteases, amylases and lipases, as well as other proteins secreted in a mammal that affect the digestive process either directly or indirectly. In one aspect, digestive enzymes present in the composition include an amylase, a protease, or a lipase.

In another aspect, digestive enzymes present in the composition include two or more of: an amylase, a protease, and a lipase.

In one aspect, digestive enzymes present in the composition include an amylase, a protease, and a lipase.

In another aspect, a composition may further contain one or more of cellulase, papaya, bromelain, chymotrypsin, and trypsin.

In one embodiment, the digestive or pancreatic enzyme composition comprises one or more of the following: amylases, proteases, cellulase, papaya, bromelain, lipases, chymotrypsin, and trypsin.

Compositions may contain an amount of protease from about 5,000; about 7,500; about 10,000; about 15,000; about 20,000; about 25,000; about 30,000; about 35,000; about 40,000; about 50,000; about 55,000; about 65,000; about 70,000; about 75,000; about 90,000; about 95,000; about 100,000; about 110,000; about 115,000; about 130,000; about 140,000; about 140,400; about 150,000; about 155,000; about 160,000; about 170,000; about 175,000; about 180,000; about 190,000; about 195,000; about 200,000; about 210,000; about 220,000; about 230,000; about 240,000; about 250,000; about 280,000; about 290,000; about 300,000; about 310,000; about 320,000; about 330,000; about 340,000; about 350,000; about 360,000; about 370,000; about 380,000; about 390,000; about 400,000; about 410,000; about 420,000; about 430,000; about 440,000; about 450,000; about 465,000; about 470,000; about 480,000; about 490,000; about 500,000; about 510,000; about 520,000; about 530,000; about 540,000; about 550,000; about 560,000; about 570,000; about 580,000; about 590,000; about 600,000; about 610,000; about 620,000; about 630,000; about 640,000; about 650,000; about 660,000; about 670,000; about 680,000; about 690,000; about 700,000; about 710,000; about 720,000; about 730,000; about 740,000; about 750,000; about 760,000; about 770,000; about 780,000; about 790,000; about 800,000; about 810,000; about 820,000; about 830,000; about 840,000; about 850,000; about 860,000; about 870,000; about 880,000; about 890,000; about 900,000; about 910,000; about 920,000; about 930,000; about 940,000; about 950,000; about 960,000; about 970,000; about 980,000; about 990,000; about 1,000,000; about 1,010,000; about 1,020,000; about 1,020,000; about 1,030,000; about 1,040,000; about 1,050,000; about 1,060,000; about 1,070,000; about 1,080,000; about 1,090,000; about 1,100,000; about 1,100,000; about 1,120,000; about 1,130,000; about 1,140,000; about 1,150,000; about 1,170,000; about 1,190,000; about 1,200,000; about 1,210,000; about 1,250,000; about 1,300,000; about 1,350,000; about 1,400,000; about 1,450,000; or about 1,500,000; about 1,200,000; about 1,250,000; about 1,300,000; about 1,350,000; about 1,400,000; about 1,450,000; or about 1,500,000 U.S.P. units/dose along with all values in between per dose.

Compositions may contain an amount of amylase from about 1,000 to about 15,000,000; from about 5,000 to about 1,000,000; from about 15,000 to about 750,000; from about 50,000 to about 500,000; from about 75,000 to about 250,000; from about 95,000 to about 200,000; or from about 100,000 to about 150,000 U.S.P. units/dose. Compositions may contain an amount of amylase including, but not limited to, about 1,000; about 3,000; about 5,000; about 7,500; about 10,000; about 15,000; about 20,000; about 25,000; about 30,000; about 35,000; about 40,000; about 50,000; about 65,000; about 70,000; about 75,000; about 100,000; about 140,000; about 144,000; about 210,000; about 280,000; about 350,000; about 420,000; about 490,000; about 500,000; about 560,000; about 630,000; about 700,000; about 770,000; about 840,000; about 910,000; about 980,000; about 1,000,000; about 1,050,000; about 2,000,000; about 3,000,000; about 4,000,000; about 5,000,000; about 6,000,000; about 7,000,000; about 8,000,000; about 9,000,000; about 10,000,000; about 11,000,000; about 12,000,000; about 13,000,000; about 14,000,000; and about 15,000,000 U.S.P. units/dose, along with all values in-between per dose Compositions may contain an amount of lipase from about 1,500 to about 282,000; from about 5,000 to about 200,000; from about 5,000 to about 150,000; from about 75,000 to about 100,000; from about 10,000 to about 75,000; from about 15,000 to about 50,000; or from about 20,000 to about 40,000 U.S.P. units/dose. Compositions may contain an amount of lipase including, but not limited to, about 1,500; about 1,880; about 2,000; about 3,000; about 5,000; about 7,500; about 8,400; about 10,000; about 15,000; about 16,800; about 20,000; about 23,000; about 23,040; about 25,000; about 30,000; about 33,600; about 40,000; about 50,000; about 50,400; about 65,000; about 67,200; about 75,000; about 84,000; about 100,000; about 100,800; about 117,600; about 125,000; about 134,400; about 150,000; about 151,200; about 168,000; about 184,800; about 200,000; about 201,600; about 218,400; about 235,200; about 250,000; about 252,000; and about 282,000 U.S.P. units/dose along with all values in-between per dose.

In another embodiment, the digestive enzyme composition is comprised of protease, lipase, and amylase where the activity of protease is between about 5,000 to about 1,500,000 U.S.P. units/dose, or between about 10,000 to about 1,500,000 U.S.P. units/dose including, but not limited to, about 5,000; about 7,500; about 10,000; about 15,000; about 20,000; about 25,000; about 30,000; about 35,000; about 40,000; about 50,000; about 55,000; about 65,000; about 70,000; about 75,000; about 90,000; about 95,000; about 100,000; about 110,000; about 115,000; about 130,000; about 140,000; about 140,400; about 150,000; about 155,000; about 160,000; about 170,000; about 175,000; about 180,000; about 190,000; about 195,000; about 200,000; about 210,000; about 220,000; about 230,000; about 240,000; about 250,000; about 280,000; about 290,000; about 300,000; about 310,000; about 320,000; about 330,000; about 340,000; about 350,000; about 360,000; about 370,000; about 380,000; about 390,000; about 400,000; about 410,000; about 420,000; about 430,000; about 440,000; about 450,000; about 465,000; about 470,000; about 480,000; about 490,000; about 500,000; about 510,000; about 520,000; about 530,000; about 540,000; about 550,000; about 560,000; about 570,000; about 580,000; about 590,000; about 600,000; about 610,000; about 620,000; about 630,000; about 640,000; about 650,000; about 660,000; about 670,000; about 680,000; about 690,000; about 700,000; about 710,000; about 720,000; about 730,000; about 740,000; about 750,000; about 760,000; about 770,000; about 780,000; about 790,000; about 800,000; about 810,000; about 820,000; about 830,000; about 840,000; about 850,000; about 860,000; about 870,000; about 880,000; about 890,000; about 900,000; about 910,000; about 920,000; about 930,000; about 940,000; about 950,000; about 960,000; about 970,000; about 980,000; about 990,000; about 1,000,000; about 1,010,000; about 1,020,000; about 1,020,000; about 1,030,000; about 1,040,000; about 1,050,000; about 1,060,000; about 1,070,000; about 1,080,000; about 1,090,000; about 1,100,000; about 1,100,000; about 1,120,000; about 1,130,000; about 1,140,000; about 1,150,000; about 1,170,000; about 1,190,000; about 1,200,000; about 1,210,000; about 1,250,000; about 1,300,000; about 1,350,000; about 1,400,000; about 1,450,000; or about 1,500,000; about 1,200,000; about 1,250,000; about 1,300,000; about 1,350,000; about 1,400,000; about 1,450,000; or about 1,500,000 U.S.P. units/dose along with all values in between per dose and where the ratio of protease to lipase is such that the amount of lipase is never more than 0.188 times the amount of protease; and further wherein the ratio of protease activity to amylase activity is between 1:0.1 and 1:10.

In some embodiments, the digestive enzyme composition comprises at least one protease and at least one lipase, wherein the ratio of total proteases to total lipases (in U.S.P. units) ranges from about 5.371:1 to about 20:1 including 5.371:1, 6:1, 7:1, 8:1, 9:1, 10:1, 11:1, 12;1, 13;1, 14:1, 15:1, 16;1, 17:1, 18:1, 19:1 and 20:1, along with all values in-between. In some embodiments, the ratio of proteases to lipases ranges from about 5.371:1 to about 10:1 including 5.371:1, 6:1, 7:1, 8:1, 9:1, and 10:1, along with all values in-between.

In yet another embodiment, the digestive enzyme composition comprises at least one protease and at least one lipase, wherein the ratio of total proteases to total lipases (in U.S.P. units/dose) ranges from about 5.371:1 to about 20:1 including 5.371:1, 6:1, 7.1, 8.1, 9:1, 10:1, 11:1, 12:1, 13:1, 14:1, 15:1, 16:1, 17:1, 18:1, 19:1, and 20:1, along with all values in-between. In another embodiment, the digestive enzyme composition comprises at least one protease and at least one lipase, wherein the ratio of total proteases to total lipases (in U.S.P. units/dose) ranges from about 1:1 to about 20:1. In yet another embodiment, the ratio of proteases to lipases ranges from about 4:1 to about 10:1. In one embodiment, the ratio of proteases to lipases ranges from about 5.371:1 to about 10:1 including 5.371:1, 6:1, 7:1, 8:1, 9:1, and 10:1 along with all values in-between. In one embodiment, the digestive enzyme composition comprises at least one protease and at least one amylase, wherein the ratio of total proteases to total amylases (in U.S.P. units/dose) ranges from about 1:0.1 to about 1:10 including 1:0.25, 1:0.5, 1:0.75, 1:1, 1:1.25, 1:1.5, 1:1.75:1:2, 1:1.25, 1:1.5, 1:1.75, 1:1.2, 1:1.25, 1:1.5, 1:1.75, 1:1.2, 1:1.25, 1:1.5, 1:1.75, 1:1.2:1:1.5, 1:2, 1:3, 1:4, 1:5, 1:6, 1:7, 1:8, 1.9 and 1:10 along with all values in-between.

In another embodiment, the digestive enzyme composition is comprised of protease, lipase, and amylase where the activities are: protease between about 5,000 to about 1,500,000 U.S.P. units/dose, or between about 10,000 to about 1,500,000 U.S.P. units/dose including about 5,000; about 7,500; about 10,000; about 15,000; about 20,000; about 25,000; about 30,000; about 35,000; about 40,000; about 50,000; about 55,000; about 65,000; about 70,000; about 75,000; about 90,000; about 95,000; about 100,000; about 110,000; about 115,000; about 130,000; about 140,000; about 140,400; about 150,000; about 155,000; about 160,000; about 170,000; about 175,000; about 180,000; about 190,000; about 195,000; about 200,000; about 210,000; about 220,000; about 230,000; about 240,000; about 250,000; about 280,000; about 290,000; about 300,000; about 310,000; about 320,000; about 330,000; about 340,000; about 350,000; about 360,000; about 370,000; about 380,000; about 390,000; about 400,000; about 410,000; about 420,000; about 430,000; about 440,000; about 450,000; about 465,000; about 470,000; about 480,000; about 490,000; about 500,000; about 510,000; about 520,000; about 530,000; about 540,000; about 550,000; about 560,000; about 570,000; about 580,000; about 590,000; about 600,000; about 610,000; about 620,000; about 630,000; about 640,000; about 650,000; about 660,000; about 670,000;

about 680,000; about 690,000; about 700,000; about 710,000; about 720,000; about 730,000; about 740,000; about 750,000; about 760,000; about 770,000; about 780,000; about 790,000; about 800,000; about 810,000; about 820,000; about 830,000; about 840,000; about 850,000; about 860,000; about 870,000; about 880,000; about 890,000; about 900,000; about 910,000; about 920,000; about 930,000; about 940,000; about 950,000; about 960,000; about 970,000; about 980,000; about 990,000; about 1,000,000; about 1,010,000; about 1,020,000; about 1,020,000; about 1,030,000; about 1,040,000; about 1,050,000; about 1,060,000; about 1,070,000; about 1,080,000; about 1,090,000; about 1,100,000; about 1,100,000; about 1,120,000; about 1,130,000; about 1,140,000; about 1,150,000; about 1,170,000; about 1,190,000; about 1,200,000; about 1,210,000; about 1,250,000; about 1,300,000; about 1,350,000; about 1,400,000; about 1,450,000; or about 1,500,000; about 1,200,000; about 1,250,000; about 1,300,000; about 1,350,000; about 1,400,000; about 1,450,000; or about 1,500,000 U.S.P. units/dose along with all values in between per dose and where the ratio of protease to lipase is such that the amount of lipase is never more than 0.188 times the amount of protease and where the ratio of protease activity to amylase activity is between 1:0.1 and 1:10.

In yet another embodiment, the digestive enzyme composition comprises at least one protease and at least one lipase, wherein the ratio of total proteases to total lipases (in U.S.P. units/dose) ranges from about 5.371:1 to about 20:1 including 5.371:1, 6:1, 7.1, 8.1, 9:1, 10:1, 11:1, 12:1, 13:1, 14:1, 15:1, 16:1, 17:1, 18:1, 19:1, and 20:1, along with all values in-between. In another embodiment, the digestive enzyme composition comprises at least one protease and at least one lipase, wherein the ratio of total proteases to total lipases (in U.S.P. units/dose) ranges from about 1:1 to about 20:1. In yet another embodiment, the ratio of proteases to lipases ranges from about 4:1 to about 10:1. In one embodiment, the ratio of proteases to lipases ranges from about 5.371:1 to about 10:1 including 5.371:1, 6:1, 7:1, 8:1, 9:1, and 10:1 along with all values in-between. In yet another embodiment, the ratio of proteases to lipases ranges from about 1:3 to about 1:0.57. In another embodiment, the ratio of proteases to lipases ranges from about 1:4 to about 1:0.05

In one embodiment, the digestive enzyme composition comprises at least one protease and at least one amylase, wherein the ratio of total proteases to total amylases (in U.S.P. units/dose) ranges from about 1:0.1 to about 1:10 including 1:0.25, 1:0.5, 1:0.75, 1:1, 1:1.25, 1:1.5, 1:1.75:1:2, 1:1.25, 1:1.5, 1:1.75, 1:1.2, 1:1.25, 1:1.5, 1:1.75, 1:1.2, 1:1.25, 1:1.5, 1:1.75, 1:1.2:1:1.5, 1:2, 1:3, 1:4, 1:5, 1:6, 1:7, 1:8, 1.9 and 1:10 along with all values in-between.

In another embodiment, the digestive enzyme composition comprises at least one protease and at least one amylase, wherein the ratio of total proteases to total amylases (in U.S.P. units/dose) ranges from about 1:6 to about 1:0.14. In another embodiment, the ratio of proteases to amylases ranges from about 1:7 to about 1:0.125.

In yet another embodiment, the digestive enzyme composition comprises at least one protease wherein the activity of protease is from about 5,000; about 7,500; about 10,000; about 15,000; about 20,000; about 25,000; about 30,000; about 35,000; about 40,000; about 50,000; about 55,000; about 65,000; about 70,000; about 75,000; about 90,000; about 95,000; about 100,000; about 110,000; about 115,000; about 130,000; about 140,000; about 140,400; about 150,000; about 155,000; about 160,000; about 170,000; about 175,000; about 180,000; about 190,000; about 195,000; about 200,000; about 210,000; about 220,000; about 230,000; about 240,000; about 250,000; about 280,000; about 290,000; about 300,000; about 310,000; about 320,000; about 330,000; about 340,000; about 350,000; about 360,000; about 370,000; about 380,000; about 390,000; about 400,000; about 410,000; about 420,000; about 430,000; about 440,000; about 450,000; about 465,000; about 470,000; about 480,000; about 490,000; about 500,000; about 510,000; about 520,000; about 530,000; about 540,000; about 550,000; about 560,000; about 570,000; about 580,000; about 590,000; about 600,000; about 610,000; about 620,000; about 630,000; about 640,000; about 650,000; about 660,000; about 670,000; about 680,000; about 690,000; about 700,000; about 710,000; about 720,000; about 730,000; about 740,000; about 750,000; about 760,000; about 770,000; about 780,000; about 790,000; about 800,000; about 810,000; about 820,000; about 830,000; about 840,000; about 850,000; about 860,000; about 870,000; about 880,000; about 890,000; about 900,000; about 910,000; about 920,000; about 930,000; about 940,000; about 950,000; about 960,000; about 970,000; about 980,000; about 990,000; about 1,000,000; about 1,010,000; about 1,020,000; about 1,020,000; about 1,030,000; about 1,040,000; about 1,050,000; about 1,060,000; about 1,070,000; about 1,080,000; about 1,090,000; about 1,100,000; about 1,100,000; about 1,120,000; about 1,130,000; about 1,140,000; about 1,150,000; about 1,170,000; about 1,190,000; about 1,200,000; about 1,210,000; about 1,250,000; about 1,300,000; about 1,350,000; about 1,400,000; about 1,450,000; or about 1,500,000; about 1,200,000; about 1,250,000; about 1,300,000; about 1,350,000; about 1,400,000; about 1,450,000; or about 1,500,000 U.S.P. units/dose along with all values in between per dose.

In yet another embodiment, the digestive enzyme composition comprises only one or more coated or uncoated proteases, wherein the activity of protease is between 10,000 to 1,500,000; from about 25,000 to about 1,000,000; from about 50,000 to about 750,000; from about 75,000 to about 500,000; from about 85,000 to about 250,000; from about 95,000 to about 200,000; or from about 110,000 to about 150,000 U.S.P. units/dose. Compositions may contain an amount of protease including, but not limited to, about 5,000; about 7,500; about 10,000; about 15,000; about 20,000; about 25,000; about 30,000; about 35,000; about 40,000; about 50,000; about 55,000; about 65,000; about 70,000; about 75,000; about 90,000; about 95,000; about 100,000; about 110,000; about 115,000; about 130,000; about 140,000; about 140,400; about 150,000; about 155,000; about 160,000; about 170,000; about 175,000; about 180,000; about 190,000; about 195,000; about 200,000; about 210,000; about 220,000; about 230,000; about 240,000; about 250,000; about 280,000; about 290,000; about 300,000; about 310,000; about 320,000; about 330,000; about 340,000; about 350,000; about 360,000; about 370,000; about 380,000; about 390,000; about 400,000; about 410,000; about 420,000; about 430,000; about 440,000; about 450,000; about 465,000; about 470,000; about 480,000; about 490,000; about 500,000; about 510,000; about 520,000; about 530,000; about 540,000; about 550,000; about 560,000; about 570,000; about 580,000; about 590,000; about 600,000; about 610,000; about 620,000; about 630,000; about 640,000; about 650,000; about 660,000; about 670,000; about 680,000; about 690,000; about 700,000; about 710,000; about 720,000; about 730,000; about 740,000; about 750,000; about 760,000; about 770,000; about 780,000; about 790,000; about 800,000; about 810,000; about 820,000; about 830,000; about 840,000; about 850,000; about 860,000; about 870,000; about 880,000;

about 890,000; about 900,000; about 910,000; about 920,000; about 930,000; about 940,000; about 950,000; about 960,000; about 970,000; about 980,000; about 990,000; about 1,000,000; about 1,010,000; about 1,020,000; about 1,020,000; about 1,030,000; about 1,040,000; about 1,050,000; about 1,060,000; about 1,070,000; about 1,080,000; about 1,090,000; about 1,100,000; about 1,100,000; about 1,120,000; about 1,130,000; about 1,140,000; about 1,150,000; about 1,170,000; about 1,190,000; about 1,200,000; about 1,210,000; about 1,250,000; about 1,300,000; about 1,350,000; about 1,400,000; about 1,450,000; or about 1,500,000; about 1,200,000; about 1,250,000; about 1,300,000; about 1,350,000; about 1,400,000; about 1,450,000; or about 1,500,000 U.S.P. units/dose along with all values in between per dose. An added benefit is that this formulation will be useful in very young infants who are not able to tolerate lipase activity.

Provided herein is a pharmaceutical composition comprising digestive enzymes for use in the methods described herein, wherein the digestive enzymes comprise about 23,000 U.S.P. units/dose of lipase, about 144,000 U.S.P. units/dose of amylase and about 140,000 U.S.P. units/dose of protease.

Provided herein is a pharmaceutical composition comprising digestive enzymes for use in the methods described herein, wherein the digestive enzymes comprise about 23,040 U.S.P. units/dose of lipase, about 144,000 U.S.P. units/dose of amylase and about 140,400 U.S.P. units/dose of protease.

Provided herein is a pharmaceutical composition comprising digestive enzymes for use in the methods described herein, wherein the digestive enzymes comprise about 16,800 U.S.P. units/dose of lipase, about 70,000 U.S.P. units/dose of protease, and about 70,000 U.S.P. units/dose of amylase.

Provided herein is a pharmaceutical composition comprising digestive enzymes for use in the methods described herein, wherein the digestive enzymes comprise about 16,800 U.S.P. units/dose of lipase, about 110,000 U.S.P. units/dose of protease, and about 70,000 U.S.P. units/dose of amylase.

Compositions contemplated herein include, but are not limited to, pellets, capsules, caplets, beadlets, sprinkles, tablets, softgels or other carriers.

Provided herein are dose forms of a composition provided herein. Non-limiting exemplary doses are set forth in Table 1.

| Dose | Supplemented with Protease |
|---|---|
| Lipase, U.S.P. units 8,400<br>Protease, U.S.P. units 35,000<br>Amylase, U.S.P. units 35,000 | Protease, U.S.P. units 0;<br>Protease, U.S.P. units 20,000;<br>Protease, U.S.P. units 40,000;<br>Protease, U.S.P. units 60,000;<br>Protease, U.S.P. units 80,000;<br>Protease, U.S.P. units 100,000;<br>Protease, U.S.P. units 120,000;<br>Protease, U.S.P. units 140,000; or<br>Protease, U.S.P. units 160,000. |
| Lipase, U.S.P. units 16,800<br>Protease, U.S.P. units 70,000<br>Amylase, U.S.P. units 70,000 | Protease, U.S.P. units 0;<br>Protease, U.S.P. units 20,000;<br>Protease, U.S.P. units 40,000;<br>Protease, U.S.P. units 60,000;<br>Protease, U.S.P. units 80,000;<br>Protease, U.S.P. units 100,000;<br>Protease, U.S.P. units 120,000;<br>Protease, U.S.P. units 140,000; or<br>Protease, U.S.P. units 160,000. |
| Lipase, U.S.P. units 33,600<br>Protease, U.S.P. units 140,000<br>Amylase, U.S.P. units 140,000 | Protease, U.S.P. units 0;<br>Protease, U.S.P. units 20,000;<br>Protease, U.S.P. units 40,000;<br>Protease, U.S.P. units 60,000;<br>Protease, U.S.P. units 80,000;<br>Protease, U.S.P. units 100,000;<br>Protease, U.S.P. units 120,000;<br>Protease, U.S.P. units 140,000; or<br>Protease, U.S.P. units 160,000. |
| Lipase, U.S.P. units 50,400<br>Protease, U.S.P. units 210,000<br>Amylase, U.S.P. units 210,000 | Protease, U.S.P. units 0;<br>Protease, U.S.P. units 20,000;<br>Protease, U.S.P. units 40,000;<br>Protease, U.S.P. units 60,000;<br>Protease, U.S.P. units 80,000;<br>Protease, U.S.P. units 100,000;<br>Protease, U.S.P. units 120,000;<br>Protease, U.S.P. units 140,000; or<br>Protease, U.S.P. units 160,000. |
| Lipase, U.S.P. units 67,200<br>Protease, U.S.P. units 280,000<br>Amylase, U.S.P. units 280,000 | Protease, U.S.P. units 0;<br>Protease, U.S.P. units 20,000;<br>Protease, U.S.P. units 40,000;<br>Protease, U.S.P. units 60,000;<br>Protease, U.S.P. units 80,000;<br>Protease, U.S.P. units 100,000;<br>Protease, U.S.P. units 120,000;<br>Protease, U.S.P. units 140,000; or<br>Protease, U.S.P. units 160,000. |
| Lipase, U.S.P. units 84,000<br>Protease, U.S.P. units 350,000<br>Amylase, U.S.P. units 350,000 | Protease, U.S.P. units 0;<br>Protease, U.S.P. units 20,000;<br>Protease, U.S.P. units 40,000;<br>Protease, U.S.P. units 60,000;<br>Protease, U.S.P. units 80,000;<br>Protease, U.S.P. units 100,000;<br>Protease, U.S.P. units 120,000;<br>Protease, U.S.P. units 140,000; or<br>Protease, U.S.P. units 160,000. |
| Lipase, U.S.P. units 100,800<br>Protease, U.S.P. units 420,000<br>Amylase, U.S.P. units 420,000 | Protease, U.S.P. units 0;<br>Protease, U.S.P. units 20,000;<br>Protease, U.S.P. units 40,000;<br>Protease, U.S.P. units 60,000;<br>Protease, U.S.P. units 80,000;<br>Protease, U.S.P. units 100,000;<br>Protease, U.S.P. units 120,000;<br>Protease, U.S.P. units 140,000; or<br>Protease, U.S.P. units 160,000. |
| Lipase, U.S.P. units 117,600<br>Protease, U.S.P. units 490,000<br>Amylase, U.S.P. units 490,000 | Protease, U.S.P. units 0;<br>Protease, U.S.P. units 20,000;<br>Protease, U.S.P. units 40,000;<br>Protease, U.S.P. units 60,000;<br>Protease, U.S.P. units 80,000;<br>Protease, U.S.P. units 100,000;<br>Protease, U.S.P. units 120,000;<br>Protease, U.S.P. units 140,000; or<br>Protease, U.S.P. units 160,000. |
| Lipase, U.S.P. units 134,400<br>Protease, U.S.P. units 560,000<br>Amylase, U.S.P. units 560,000 | Protease, U.S.P. units 0;<br>Protease, U.S.P. units 20,000;<br>Protease, U.S.P. units 40,000;<br>Protease, U.S.P. units 60,000;<br>Protease, U.S.P. units 80,000;<br>Protease, U.S.P. units 100,000;<br>Protease, U.S.P. units 120,000;<br>Protease, U.S.P. units 140,000; or<br>Protease, U.S.P. units 160,000. |
| Lipase, U.S.P. units 151,200<br>Protease, U.S.P. units 630,000<br>Amylase, U.S.P. units 630,000 | Protease, U.S.P. units 0;<br>Protease, U.S.P. units 20,000;<br>Protease, U.S.P. units 40,000;<br>Protease, U.S.P. units 60,000;<br>Protease, U.S.P. units 80,000;<br>Protease, U.S.P. units 100,000;<br>Protease, U.S.P. units 120,000;<br>Protease, U.S.P. units 140,000; or<br>Protease, U.S.P. units 160,000. |
| Lipase, U.S.P. units 168,000<br>Protease, U.S.P. units 700,000<br>Amylase, U.S.P. units 700,000 | Protease, U.S.P. units 0;<br>Protease, U.S.P. units 20,000;<br>Protease, U.S.P. units 40,000;<br>Protease, U.S.P. units 60,000;<br>Protease, U.S.P. units 80,000;<br>Protease, U.S.P. units 100,000; |

| Dose | Supplemented with Protease |
|---|---|
| | Protease, U.S.P. units 120,000; |
| | Protease, U.S.P. units 140,000; or |
| | Protease, U.S.P. units 160,000. |
| Lipase, U.S.P. units 184,800 | Protease, U.S.P. units 0; |
| Protease, U.S.P. units 770,000 | Protease, U.S.P. units 20,000; |
| Amylase, U.S.P. units 770,000 | Protease, U.S.P. units 40,000; |
| | Protease, U.S.P. units 60,000; |
| | Protease, U.S.P. units 80,000; |
| | Protease, U.S.P. units 100,000; |
| | Protease, U.S.P. units 120,000; |
| | Protease, U.S.P. units 140,000; or |
| | Protease, U.S.P. units 160,000. |
| Lipase, U.S.P. units 201,600 | Protease, U.S.P. units 0; |
| Protease, U.S.P. units 840,000 | Protease, U.S.P. units 20,000; |
| Amylase, U.S.P. units 840,000 | Protease, U.S.P. units 40,000; |
| | Protease, U.S.P. units 60,000; |
| | Protease, U.S.P. units 80,000; |
| | Protease, U.S.P. units 100,000; |
| | Protease, U.S.P. units 120,000; |
| | Protease, U.S.P. units 140,000; or |
| | Protease, U.S.P. units 160,000. |
| Lipase, U.S.P. units 218,400 | Protease, U.S.P. units 0; |
| Protease, U.S.P. units 910,000 | Protease, U.S.P. units 20,000; |
| Amylase, U.S.P. units 910,000 | Protease, U.S.P. units 40,000; |
| | Protease, U.S.P. units 60,000; |
| | Protease, U.S.P. units 80,000; |
| | Protease, U.S.P. units 100,000; |
| | Protease, U.S.P. units 120,000; |
| | Protease, U.S.P. units 140,000; or |
| | Protease, U.S.P. units 160,000. |
| Lipase, U.S.P. units 235,200 | Protease, U.S.P. units 0; |
| Protease, U.S.P. units 980,000 | Protease, U.S.P. units 20,000; |
| Amylase, U.S.P. units 980,000 | Protease, U.S.P. units 40,000; |
| | Protease, U.S.P. units 60,000; |
| | Protease, U.S.P. units 80,000; |
| | Protease, U.S.P. units 100,000; |
| | Protease, U.S.P. units 120,000; |
| | Protease, U.S.P. units 140,000; or |
| | Protease, U.S.P. units 160,000. |
| Lipase, U.S.P. units 252,000 | Protease, U.S.P. units 0; |
| Protease, U.S.P. units 1,050,000 | Protease, U.S.P. units 20,000; |
| Amylase, U.S.P. units 1,050,000 | Protease, U.S.P. units 40,000; |
| | Protease, U.S.P. units 60,000; |
| | Protease, U.S.P. units 80,000; |
| | Protease, U.S.P. units 100,000; |
| | Protease, U.S.P. units 120,000; |
| | Protease, U.S.P. units 140,000; or |
| | Protease, U.S.P. units 160,000. |

Provided herein is a dose of a pharmaceutical composition that comprises digestive enzymes for use in the methods described herein, wherein the dose comprises about 8,400 U.S.P. units lipase, 35,000 U.S.P. units protease, and about 35,000 U.S.P. units amylase.

Provided herein is a dose of a pharmaceutical composition comprising digestive enzymes for use in the methods described herein, wherein the dose comprises about 16,800 U.S.P. units Lipase, about 70,000 U.S.P. units Protease, and about 70,000 U.S.P. units Amylase.

Provided herein is a dose of a pharmaceutical composition comprising digestive enzymes for use in the methods described herein, wherein the dose comprises about 33,600 U.S.P. units Lipase, about 140,000 U.S.P. units Protease, and about 140,000 U.S.P. units Amylase.

Provided herein is a dose of a pharmaceutical composition comprising digestive enzymes for use in the methods described herein, wherein the dose comprises about 50,400 U.S.P. units Lipase, about 210,000 U.S.P. units Protease, and about 210,000 U.S.P. units Amylase.

Provided herein is a dose of a pharmaceutical composition comprising digestive enzymes for use in the methods described herein, wherein the dose comprises about 67,200 U.S.P. units Lipase, about 280,000 U.S.P. units Protease, and about 280,000 U.S.P. units Amylase.

Provided herein is a dose of a pharmaceutical composition comprising digestive enzymes for use in the methods described herein, wherein the dose comprises about 84,000 U.S.P. units Lipase, about 350,000 U.S.P. units Protease, and about 350,000 U.S.P. units Amylase.

Provided herein is a dose of a pharmaceutical composition comprising digestive enzymes for use in the methods described herein, wherein the dose comprises about 100,800 U.S.P. units Lipase, about 420,000 U.S.P. units Protease, and about 420,000 U.S.P. units Amylase.

Provided herein is a dose of a pharmaceutical composition comprising digestive enzymes for use in the methods described herein, wherein the dose comprises about 117,600 U.S.P. units Lipase, about 490,000 U.S.P. units Protease, and about 490,000 U.S.P. units Amylase.

Provided herein is a dose of a pharmaceutical composition comprising digestive enzymes for use in the methods described herein, wherein the dose comprises about 134,400 U.S.P. units Lipase, about 560,000 U.S.P. units Protease, and about 560,000 U.S.P. units Amylase.

Provided herein is a dose of a pharmaceutical composition comprising digestive enzymes for use in the methods described herein, wherein the dose comprises about 151,200 U.S.P. units Lipase, about 630,000 U.S.P. units Protease, and about 630,000 U.S.P. units Amylase.

Provided herein is a dose of a pharmaceutical composition comprising digestive enzymes for use in the methods described herein, wherein the dose comprises about 168,000 U.S.P. units Lipase, about 700,000 U.S.P. units Protease, and about 700,000 U.S.P. units Amylase.

Provided herein is a dose of a pharmaceutical composition comprising digestive enzymes for use in the methods described herein, wherein the dose comprises about 184,800 U.S.P. units Lipase, about 770,000 U.S.P. units Protease, and about 770,000 U.S.P. units Amylase.

Provided herein is a dose of a pharmaceutical composition comprising digestive enzymes for use in the methods described herein, wherein the dose comprises about 201,600 U.S.P. units Lipase, about 840,000 U.S.P. units Protease, and about 840,000 U.S.P. units Amylase.

Provided herein is a dose of a pharmaceutical composition comprising digestive enzymes for use in the methods described herein, wherein the dose comprises about 218,400 U.S.P. units Lipase, about 910,000 U.S.P. units Protease, and about 910,000 U.S.P. units Amylase.

Provided herein is a dose of a pharmaceutical composition comprising digestive enzymes for use in the methods described herein, wherein the dose comprises about 235,200 U.S.P. units Lipase, about 980,000 U.S.P. units Protease, and about 980,000 U.S.P. units Amylase.

Provided herein is a dose of a pharmaceutical composition comprising digestive enzymes for use in the methods described herein, wherein the dose comprises about 252,000 U.S.P. units Lipase, about 1,050,000 U.S.P. units Protease, and about 1,050,000 U.S.P. units Amylase.

Any of the doses may be optionally supplemented with additional protease. In one embodiment, a dose may be supplemented with about 0 U.S.P. units; about 20,000 U.S.P. units; about 40,000 U.S.P. units; about 60,000 U.S.P. units; about 80,000 U.S.P. units; about 100,000 U.S.P. units; about 120,000 U.S.P. units; about 140,000 U.S.P. units; or about 160,000 U.S.P. units protease.

A dose of a pharmaceutical composition described herein may be formulated for oral administered in an amount of, for example, about 3 teaspoons, about 2.75 teaspoons, about 2.5 teaspoons, about 2.25 teaspoons, about 2 teaspoons, about 1.75 teaspoons, about 1.5 teaspoons, about 1.25 teaspoons, about 1 teaspoon, about ½ teaspoon, about ¼ teaspoon, or about ⅛ teaspoon.

Alternatively, a dose of a pharmaceutical composition described herein may be formulated for oral administered in an amount of, for example, about ½ tablet, about 1 tablet, about 1.5 tablets, about 2 tablets, about 2.5 tablets, about 3 tablets, about 3.5 tablets, about 4 tablets, about 4.5 tablets, about 5 tablets, about 5.5 tablets, or about 6 tablets.

Provided herein is a single composition that comprises a dose of Formulation A and a dose of Formulation B. Compositions contemplated herein include, but are not limited to, pellets, capsules, caplets, beadlets, sprinkles, tablets, softgels or other carriers.

In one embodiment, a composition comprises a dose of about ¼ teaspoon of formulation A comprises about 16,800 U.S.P. units lipase, about U.S.P. units 70,000 protease, and about 70,000 U.S.P. units amylase.

In another embodiment, a composition comprises a dose of about ⅛ teaspoon of formulation A and about ½ teaspoon of formulation B, where the composition comprises about 8,400 U.S.P. units lipase, about 55,000 U.S.P. units protease, about U.S.P. units 35,000 amylase.

In one embodiment, a composition comprises a dose of about ⅛ teaspoon of formulation A and about ⅛ teaspoon of formulation B, where the composition comprises about 8,400 U.S.P. units lipase, about 75,000 U.S.P. units protease, and about 35,000 U.S.P. units amylase.

In one embodiment, a composition comprises a single dosage form of a composition dose of about ¼ teaspoon of formulation A and ½ teaspoon of formulation B, where the composition comprises about 16,800 U.S.P. units lipase, about U.S.P. units 90,000 protease, and about 70,000 U.S.P. units amylase.

In yet another embodiment, the digestive enzyme composition comprises only one more protease and only one or more amylases, which may be coated or uncoated, wherein the ratio of total proteases to total amylases (in U.S.P. units/dose) ranges from about 1:0.1 to about 1:10 including 1:0.25, 1:0.5, 1:0.75, 1:1, 1:1.25, 1:1.5, 1:1.75:1:2, 1:1.25, 1:1.5, 1:1.75, 1:1.2, 1:1.25, 1:1.5, 1:1.75, 1:1.2, 1:1.25, 1:1.5, 1:1.75, 1:1.2:1:1.5, 1:2, 1:3, 1:4, 1:5, 1:6, 1:7, 1:8, 1.9 and 1:10 along with all values in-between. In another embodiment, the digestive enzyme composition comprises at least one protease and at least one amylase, wherein the ratio of total proteases to total amylases (in U.S.P. units/dose) ranges from about 1:6 to about 1:0.14. In another embodiment, the ratio of proteases to amylases ranges from about 1:7 to about 1:0.125. An added benefit is that this formulation will be useful in very young infants who are not able to tolerate lipase activity.

In one embodiment the coated or uncoated digestive enzymes to be administered are comprised of pancreatin, pancrelipase, or a combination thereof. In one embodiment a coating technology can be used, such as the ones described in U.S. Pat. No. 6,835,397, U.S. RE40,059, U.S. Pat. No. 6,153,236, or US 2009-0004285 which are herein incorporated by reference in their entirety.

Enzyme preparations with non-lipid enteric coatings can be used to deliver lipases in individuals in need of lipase administration. Certain methods and enzyme compositions for use in treating children and other individuals in, for example, U.S. Pat. Nos. 7,138,123, 6,660,831, 6,632,429, 6,534,063, which is herein incorporated by reference in its entirety.

The composition of the dosage form may include other components, generally utilized in pharmaceutical preparations including but not limited to binders, disintegrants, extracts, lubricants, fillers, flavorings, preservatives, colorants, taste maskers, diluents and coating agents, such as vegetable oil, crystalline oils, and other coating methodologies.

In one embodiment, coating of a digestive enzyme preparation is used to obtain release at selected transit times or in selected locations of the gastrointestinal tract of humans. In one aspect, this disclosure relates to controlled release enzyme preparations administered to a subject with Celiac Disease or a related disorder.

In yet another aspect, this disclosure relates to an enzyme delivery system comprising a coated enzyme preparation having particles which comprise: (a) a core comprising pancreatic or digestive enzymes present in an amount from about 5% to 99% by weight of the particles; and (b) a generally uniform coating to provide for controlled release of the enzymes, the coating comprising an emulsifiable lipid. In one aspect, the coated enzyme preparation particles of the enzyme delivery system are non-aerosolizable.

In some embodiments a coated digestive enzyme preparation comprising (a) a core containing a digestive enzyme particle, where the enzyme present in an amount of from about 5% to 95% by weight of the particles, including 5%, 10%, 15%, 20%, 25%, 30%, 35%, 40%, 45%, 50%, 55%, 60%, 65%, 70%, 75%, 80%, 85%, 90% and 95% by weight, along with all values in-between; and (b) a coating comprising a crystallizable lipid, wherein the coating continuously coats the core and the crystallizable lipid releases the enzyme upon exposure to physiological conditions.

In some embodiments a coated enzyme preparation having particles which comprise: (a) a core comprising pancreatic or other digestive enzymes present in an amount of from about 5% to 95% by weight of the particles, including 5%, 10%, 15%, 20%, 25%, 30%, 35%, 40%, 45%, 50%, 55%, 60%, 65%, 70%, 75%, 80%, 85%, 90% and 95% by weight along with all values in-between; and (b) a generally uniform coating to provide for controlled release of the enzymes, the coating comprising a crystallizable lipid. In some embodiments, the coated enzyme preparation particles of the enzyme delivery system are non-aerosolizable.

The present disclosure also relates to methods of making the enzyme preparations by lipid coating and/or encapsulation of digestive enzymes. The methods comprise providing an emulsifiable lipid, and coating pancreatic/digestive enzyme particles with the lipid. The digestive enzymes comprise 5 to 99% of the coated enzyme preparations by weight.

In another aspect as described herein, the inventors have discovered that the methods of this disclosure produce coated digestive enzyme preparations comprising digestive and/or pancreatic enzymes coated with an emulsifiable lipid alone, or with a lipid blend to achieve a controlled rate of enzyme release, with increased release of the pancreatic/digestive enzyme upon exposure of the coated preparation to a suitable solvent. The inventors have discovered that coated pancreatic/digestive enzyme preparations having a coating consisting essentially of one or more monoglycerides exhibit time-sensitive biologically-suitable release of the pancreatic/digestive enzymes upon exposure of the coated composite to a solvent, such as water, while protecting against release in 0.1 N HCl or acidic gastric fluid.

The nature of the human digestive tract creates challenges for the delivery of digestive enzymes to patients susceptible to treatment with digestive enzymes. Multiple temperature and pH changes over the course of the digestive tract make specific delivery a challenge but a necessity. For instance, pH as low as 1 is encountered in the stomach, but rapidly increases to a more basic pH of 5-6 in the proximal small intestine. For example, generally the pH in the stomach is approximately 1.2, the pH in the duodenum is about 5.0 to 6.0; the pH in the jejunum is about 6.8, and the pH is about 7.2 in the proximal ileum and about 7.5 in the distal ileum. The low pH in the stomach that changes rapidly to a more basic pH of 5-6 in the proximal small intestines calls for a specific delivery method depending upon where the enzyme is to be delivered.

Delivery of digestive enzymes can also be challenging due to the rapid degradation and denaturing of enzymes at ambient room temperature, as well as the enhanced degradation and denaturing that can occur with high temperature, pressure, humidity and/or exposure to light. Moisture and heat together can quickly destabilize enzymes, reducing their effectiveness, and weaken their potency leading to inaccurate dosing and shortened shelf life. Denaturation or destabilization of the enzymes can reduce their effectiveness by reducing the dose of active enzymes to less than the amount needed for effective treatment. In one embodiment, to protect and stabilize the pancreatic/digestive enzyme from unfavorable conditions such as oxidation, the pancreatic/digestive enzyme (core) is coated or encapsulated in a continuous coating containing an emulsifiable lipid. In another aspect, this disclosure provides new coated enzyme preparations with improved shelf life.

Manufacturers of enzyme preparations have used enteric coatings to deliver lipases in individuals requiring administration of lipases. Because the porcine enzymes are delivered in a mixture of proteases, lipases and amylases, and because these compositions for human consumption were prepared for lipase delivery, the uses of these enteric coatings, which include such substances as hypromellose phthalate, dimethicone 1000, and dibutyl phthalate, preclude delivery of proteases at the proper location for protein digestion, which is the duodenum. All other enzyme preparations presently on the market contain at least one of these enteric coating substances and/or other additives in the preparation.

In one embodiment the present disclosure includes a coated digestive enzyme preparation and/or composite, which in some embodiments is an encapsulated pancreatic/digestive enzyme preparation. In other aspects, the disclosure includes enzyme delivery systems and pharmaceutical compositions comprising coated pancreatic/digestive enzyme preparations. These coated or encapsulated enzyme preparations contain cores comprising pancreatic or digestive enzyme particles, and a coating comprising an emulsifiable lipid.

The coatings in the digestive/pancreatic enzyme preparations create a barrier to degradation and denaturation, and allow more accurate levels of active enzymes to be utilized by treated individuals. The lipid coating of this disclosure provides a significant barrier to moisture, humidity and exposure to light by allowing for a physical barrier as well as one that prevents and/or reduces hydrolysis. The coated enzyme preparations undergo less hydrolysis as a result of protection from moisture in the environment by the lipid coating. As a result of the present disclosure, pancreatic/digestive enzymes are provided which can tolerate storage conditions (e.g., moisture, heat, oxygen, etc.) for long periods of time thus enabling extended shelf life. The coating of the encapsulated enzyme preparation protects the enzyme from the environment and provides emulsification in a solvent without detracting from the abrasion resistance of the coating. The disclosure thus further relates to more stable enzyme preparations.

It is another aspect of the present disclosure to make an enzyme preparation without the use of extenders colorants, dyes, flow enhancers and other additives to reduce the potential for allergens and other sensitivity reactions in children and other treated individuals. It has been discovered that in some embodiments, the digestive enzymes can be encapsulated with a single lipid excipient to improve retention of enzyme activity, ease of administration, tolerability, and safety of administration, among other properties. Surprisingly, digestive enzyme particles containing lipases can be successfully encapsulated with coating consisting essentially of only hydrogenated soy oil.

Porcine pancreatic/digestive enzymes possess a significant odor and taste, similar to cured or smoked pork. This taste and smell can be strong and offensive to some individuals taking enzyme replacement, and especially to children. In one embodiment, the addition of a lipid coating provides significant odor and taste masking to the enzyme preparation, which allows for the tolerance of taste, as the lipid coating is odorless and tasteless. The use of this method of taste masking not involving the use of color, dyes, perfumes or other substances is preferable for the administration of medications, which have an unpleasant or undesirable taste and odor. In another embodiment, this disclosure relates to coated digestive enzyme preparations with improved taste and odor.

In some embodiments, the coatings on the digestive enzyme particle cores are preferably continuous coatings. By "continuous", it is meant that the pancreatic/digestive enzyme is completely surrounded. The continuous coating fully surrounds or encapsulates the pancreatic/digestive enzymes. The encapsulation provides protection of the pancreatic/digestive enzyme from conditions such as moisture and oxidation.

In the manufacture of pharmaceuticals, encapsulation refers to a range of techniques used to enclose medicines in a relatively stable shell known as a capsule, allowing them to, for example, be taken orally or be used as suppositories. "Encapsulate" as used herein means that the coating completely surrounds the pancreatic/digestive enzyme. A coated or encapsulated preparation may contain one or more digestive enzyme particles enveloped in one coating to form one coated or encapsulated digestive enzyme particle in the coated or encapsulated digestive enzyme preparation.

The two main types of capsules are hard-shelled capsules, which are normally used for dry, powdered ingredients, and soft-shelled capsules, primarily used for oils and for active ingredients that are dissolved or suspended in oil. Both of these classes of capsule are made both from gelatin and from plant-based gelling substances like carrageenans and modified forms of starch and cellulose, and the latter form is usually seamless. Capsules are made in two parts by dipping metal rods in molten gelatin solution. The capsules are supplied as closed units to the pharmaceutical manufacturer. Before use, the two halves are separated, the capsule is filled with powder (either by placing a compressed slug of powder into one half of the capsule, or by filling one half of the capsule with loose powder) and the other half of the capsule is pressed on. The advantage of inserting a slug of compressed powder is that control of weight variation is better, but the machinery involved is more complex.

Sprinkle capsules are a dosage form consisting of small beads or granules of an active drug contained in a capsule that can be readily administered by simply opening up the capsule and distributing the contents over something to be swallowed.

In addition, the encapsulation also provides controlled release of the pancreatic/digestive enzyme. In one embodiment, the emulsification properties of the coating in a solvent allows for controlled release of the enzyme in the gastrointestinal (GI) system, preferably the region of the GI tract where the enzymes are to be utilized. For example, for conditions requiring treatment with proteases, the release of the protease portion of the enzymes is necessary in the proximal small intestine, thereby necessitating a lipid encapsulation, which has a dissolution profile showing a release of between 10% to 100% of the active substance into solution over a time period of between 30 and 90 minutes. In one embodiment, the dissolution profile shows a release of about 20%, 30%, 40%, 50%, 60%, 70%, 80%, 90% or 100%, and all values in between, of the coated substance into solution over a time period of about 30, 35, 40, 45, 50, 55, 60, 65, 70, 75, 80, 85 or 90 minutes and all values in between. Dissolution profiles may be obtained using methods and conditions known to those of skill in the art. For example, dissolution profiles can be determined at various pHs, including pH 1, 2, 3, 4, 5, 6, 7, 8, 9, 10 and all values in between.

The rate of release of the bioactive substance can also be controlled by the addition of additives as described below. When the preparations are exposed to a solvent, the solvent interacts with the mollifiable lipid in the coating and results in emulsification of the coating and release of the bioactive substance.

A suspension is a heterogeneous fluid containing solid particles that are sufficiently large for sedimentation. Usually they must be larger than 1 micrometer. The internal phase (solid) is dispersed throughout the external phase (fluid) through mechanical agitation, with the use of certain excipients or suspending agents. Unlike colloids, suspensions will eventually settle. An example of a suspension would be sand in water. The suspended particles are visible under a microscope and will settle over time if left undisturbed. This distinguishes a suspension from a colloid in which the suspended particles are smaller and do not settle. Colloids and suspensions are different from a solution, in which the dissolved substance (solute) does not exist as a solid and solvent and solute are homogeneously mixed. Oftentimes, powders of active ingredients may be packaged such that the addition of a diluent dissolves the powder and holds it in a liquid suspension.

A pharmaceutical preparation may be prepared in which an excipient provides a matrix to capture and protect a product before delivery. Pharmaceutical preparations may be prepared whereby the individual who takes the preparation has a reduction in the number of capsules/tablets per dosage; i.e., the preparation is stabilized and may contain a therapeutically effective amount of a protease, an amylase, and/or a lipase. Preparations may include, for example, a stabilizing matrix consisting essentially of a solidified microcrystalline cellulose which captures and protects therapeutically effective amounts of digestive enzyme particles within the stabilizing matrix. This can be done, for example, through the use of what is known in the art as PROSOLV® technology.

PROSOLV® is a combination of excipients which allow for optimized flow, compaction and product uniformity. This technology allows for uniformity in this combination, as well as manufacturing a very small tablet which would be amenable for children. With PROSOLV® technology, the ingredients are not just blended, but are co-processed, which assures that equal particles are uniformly distributed and these results are easily reproducible. This allows for stability and superb product quality.

Whether utilizing the PROSOLV® method or other methodology, the one or more digestive enzymes will be formulated and manufactured such that the particles will be uniformly distributed and there will be no overage with respect to the amount of enzyme found in the preparation. Said new drug formulation can be found in, but is not limited to, formulations which include digestive/pancreatic enzymes with and without the utilization of the PROSOLV® technology.

In a further embodiment, a direct compression method may be used for the manufacture of a pharmaceutical tablet preparation including the steps of: (a) forming an active blend by blending an intimate admixture of silicified microcrystalline cellulose and a therapeutic agent comprising one or more digestive enzymes; (b) forming a color blend by blending an intimate admixture of one or more pharmaceutically acceptable dyes and silicified microcrystalline cellulose if color is necessary; (c) combining the active blend, the color blend and a disintegrant into a pre-blend; (d) adding a lubricant to the pre-blend to form a final blend; and (e) compressing the final blend to form a pharmaceutical tablet preparation or a mixture of time released microtabs or a time released tablet.

This may be accomplished by combining the digestive enzymes with one of the patented PROSOLV® technologies, i.e.: PROSOLV® SMCC 50 or PROSOLV® SMCC 90, or other PROSOLV® technologies. When employing the PROSOLV® method, the silicified microcrystalline cellulose (SMCC) used in the preparation of the present invention may be any commercially available combination of microcrystalline cellulose granulated with colloidal silicon dioxide. The SMCC generally will be as described in Sherwood et al, *Pharm. Tech.*, October 1998, 78-88 and U.S. Pat. No. 5,585,115, which is incorporated herein by reference in its entirety. SMCC can be obtained commercially from Edward Mendell Company, Inc., a subsidiary of Penwest Ltd., under the name PROSOLV® SMCC. There are different grades of SMCC available, with particle size being the differentiating property among the grades. For example, PROSOLV® SMCC 90 has a median particle size, by sieve analysis, in the region of 90 micrometers. PROSOLV® SMCC 50 has a median particle size, by sieve analysis, in the region of about 40-50 micrometers.

A pharmaceutical composition described herein may be prepared using a direct compression method, a dry granulation method, or by wet granulation. Preferably, the digestive/pancreatic enzyme preparation may be prepared using a direct compression process. This preferred process consists of two main steps: blending and compression.

The blending step is composed of an active blend, color blend, pre-blend, and final blend (lubrication). The formulation of the present invention may include a number of other ingredients for optimal characteristics of the pharmaceutical composition. Such other ingredients and the amounts to be used are within the knowledge of one in the art and are known in the pharmaceutical arts. These may include disintegrates, lubricants and/or coloring agents among others. Suitable disintegrants include, for example, sodium starch glycolate, other starches such as pregelatinized starch, and celluloses. Suitable lubricants may be provided, such as magnesium stearate, calcium stearate, talc and stearic acid. Any coloring agent certified by the FDA may be used, such as FD&C Yellow #6, among others.

When used as a pharmaceutical preparation, elixirs contain an active ingredient that is dissolved in a solution that contains some percentage (usually 40-60%) of ethyl alcohol and is designed to be taken orally.

Syrups are oftentimes employed as a base for medicinal purposes and consist of a concentrated or saturated solution of refined sugar in distilled water.

A suspension of liquid droplets or fine solid particles in a gas is called an aerosol. This can take the form of an oral spray.

A gum may be devised whereby an active ingredient is incorporated into a vegetative resinous substance (e.g., acacia) and released via the actual mechanical effect of chewing or the action of saliva on the gum itself.

A thinstrip is an active pharmaceutical product coated by a lipid layer designed to dissolve in the mouth over a brief period of time. The same technology could be used to produce a medicated lollipop for transmucosal delivery.

In pharmaceutical terms, a granule is a small particle gathered into a larger, permanent aggregate in which the original particles can still be identified.

In some aspects, the disclosure relates to the production of selected coated enzyme preparations made by coating digestive enzyme particles with lipids not previously used in coated digestive enzyme preparations. The unique mixtures of emulsifiable lipids and enzymes can deliver certain components of the pancreatic/digestive enzymes to selected locations and/or at selected times during transit of the GI tract. In some aspects, the disclosure relates to methods of delivering digestive enzymes to humans based upon dissolution profiles.

The emulsifiable lipid may be any lipid, lipid mixture, or blend of lipid and emulsifiers which emulsifies when exposed to a solvent, and has a melting point which allows the lipid to be a solid at typical storage temperatures. The emulsifiable lipid can be a vegetable or animal derived-lipid. In another embodiment, the emulsifiable lipid consists essentially of, or comprises one or more monoglycerides, diglycerides or triglycerides, or other components including, for example, emulsifiers found in hydrogenated vegetable oils. In another embodiment the lipid is a non-polar lipid.

As used herein, animal and/or vegetable "derived" lipids can include fats and oils originating from plant or animal sources and/or tissues, and/or synthetically produced based on the structures of fats and oils originating from plant or animal sources. Lipid material may be refined, extracted or purified by known chemical or mechanical processes. The lipid may, in one embodiment, comprise a Type I U.S.P.-National Formulary vegetable oil.

The digestive enzyme used in the present disclosure can be any combination of digestive enzymes of a type produced by the pancreas, including, but not limited to digestive enzymes from a pancreatic source or other sources. The scope of the disclosure is not limited to pancreatic enzymes of porcine origin, but can be of other animal or plant origin as well as those that are synthetically derived. In one embodiment, the digestive enzyme is derived from mammalian sources such as porcine-derived digestive enzymes. In another embodiment, the enzyme includes one or more enzymes, and is plant derived, synthetically derived, recombinantly produced in microbial, yeast, or mammalian cells, or includes a mixture of enzymes from one or more sources. For example, digestive enzymes may include one or more enzymes from one or more sources mixed together. This includes, for example, the addition of single digestive enzymes to digestive enzymes derived from pancreatic sources in order to provide appropriate levels of specific enzymes that provide more effective treatment for a selected disease or condition. One source of digestive enzymes can be obtained, for example, from Scientific Protein Laboratories. In one embodiment, the digestive enzyme is, for example a pancreatin/pancrelipase composition. In another embodiment, the digestive enzymes comprise or consist essentially of 25 U.S.P. units protease, 2 U.S.P. units lipase, and 25 U.S.P. units amylase per milligram. The term digestive enzyme may refer to one or more enzymes of a type produced by the pancreas.

In one embodiment, the digestive enzyme used present as consisting of particles having various sizes. In another embodiment, the particles of digestive enzyme are screened to obtain particles of a suitable size for encapsulation by removing particles that are too fine or too large. For example, the particles may be sieved to obtain particles of a suitable size or more uniform size range for encapsulation.

In one embodiment, the minimum amount of pancreatic enzyme present in the core is at least about 5% active enzymes by weight of the coated enzyme preparation, but in another embodiment is at least about 30%, or at least about 50% by weight. In one embodiment, the maximum amount of pancreatic/digestive enzyme present in the composite is at most about 99% by weight, and in another embodiment is at most about 98%, 95%, 90%, 85%, 80%, 75% or 70% of the coated enzyme preparation. In another embodiment, the amount of pancreatic enzyme present in the composite is about 10%, 15%, 20%, 25%, 35%, 40%, 45%, 55%, 60%, 65%, 70%, 72.5%, 75%, 77.5%, 80%, 82.5%, 87.5%, or 92.5% by weight or anywhere in between. At least about or at most about a % of enzyme may include equal to or about that % of enzyme. The term "about" includes equal to, and a range that takes into account experimental error in a given measurement. As used in connection with particle sizes, the term "about" can refer to plus or minus 10, 9, 8, 7, 6, 5, 4, 3, 2 or 1% or anywhere in between. As used in connection with % particles that can be sieved, the term "about" can refer to plus or minus 10, 9, 8, 7, 6, 5, 4, 3, 2 or 1% or anywhere in between.

In one embodiment, the composition which contains the encapsulated digestive enzyme preparation or composite is delivered as a sprinkle, powder, capsule, tablet, pellet, caplet or other oral form. In another embodiment, packaging the encapsulated enzyme preparations in an enzyme delivery system that further comprises single dose sachet-housed sprinkle preparations allows for ease of delivery and accurate dosing of the enzyme by allowing a specific amount of enzyme to be delivered in each dosing. Allowing for specific unit dosing of an enzyme preparation which maintains the enzyme activity within specific stability parameters is an enhancement over other sprinkle formulations, which are housed in a multi-unit dosing form that allows for air, moisture and heat to deprecate and denature the enzyme preparation. In one embodiment, the powder or sachet is housed in a trilaminar pouch of which one layer is foil, or similar barrier to keep out moisture and to protect the enzyme preparation from adverse environmental factors. The disclosure further relates to an improvement in stability due to a reduction in hydrolysis due to the lipid encapsulation and composition of package.

In another embodiment, the lipid encapsulation methodology reduces the aerosolization of the enzyme preparation that may be caustic to the patient if inhaled. In another embodiment, the disclosure includes delivery of digestive enzymes with improved safety of administration, by reducing the amount of aerosolization of the enzyme. The lipid encapsulation reduces aerosolization and the potential for caustic burn, aspiration, and/or aspiration pneumonias in patients and administrators of the enzyme preparation, thereby reducing the potential for illness in already compromised children such as those with cystic fibrosis, and leading to safer administration.

As used herein, the term "non-aerosolizable" will be used to refer to a coated or encapsulated enzyme preparation where substantially all of the particles are large enough to eliminate or reduce aerosolization upon pouring of the coated enzyme preparation compared to uncoated enzyme particles.

As described and referred to herein, suitable pancreatic/digestive enzymes and suitable coatings may be used in the compositions and methods of this disclosure. The choice of suitable enzymes and of suitable lipid coatings, including choice of the type or amount of enzymes or coating, are guided by the specific enzyme needs of the individuals, and the selected diseases to be treated. The encapsulated enzyme preparations that are one aspect of this disclosure have not been previously described.

In another embodiment, the disclosure relates to a method of controlling the rate of release of the pancreatic/digestive enzyme from an encapsulated enzyme preparation upon exposure to a solvent. In one aspect, the method comprises blending an emulsifiable lipid with an amount of one or more additives to obtain a lipid blend and coating the digestive enzyme particle with the blend to form an encapsulated digestive enzyme preparation containing particles comprising a core which contains the enzyme, and a coating which contains the lipid. In one embodiment, the emulsifiable lipid is a blend where the emulsifiable lipid and additive are not the same, and where the rate of release of the enzyme from the encapsulated composite upon exposure to a solvent is decreased as the amount of additive is increased. In the alternative, the rate of release of the enzyme from the encapsulated composite upon exposure to a solvent is increased as the amount of additive is decreased.

The lipid coating surprisingly does not appear to be reduced or destroyed by hydrochloric acid (HCl) present in the stomach, thereby protecting the enzyme from degradation following administration until the enzyme preparation reaches its target region in the GI tract. Further the lipid coat reduces the exposure of the enzyme to attack by water, thereby reducing hydrolysis, and further protecting the digestive enzymes from degradation. In addition, the inventors have found that an excipient containing only lipid can be used to coat or encapsulate digestive enzyme particles containing lipase.

Enzyme preparations supplied by the API supplier may be provided as irregular shaped, and multi-sized particles, with uneven edges, and much clumping, and containing some crystalline salt particles. Uneven particle size and shape reduces flow properties, and interferes with packaging. In addition, pouring uncoated enzyme into the mouth of a subject would be difficult, and potentially may cause too much or too little of the enzyme to be delivered. In one embodiment, processing the digestive enzyme particles according to methods in accordance with one aspect of this disclosure yields a non-dusty, free-flowing particulate preparation suitable for sachet packaging and for pouring onto food or drink. In addition, as discussed throughout, the use of lipid encapsulation to prevent aerosolization and, therefore, increase safety, and to increase flow properties which enhance manufacturing of a pharmaceutical is an embodiment of the instant disclosure.

"Emulsifiable lipids" as used herein means those lipids that contain at least one hydrophilic group and at least one hydrophobic group, and have a structure capable of forming a hydrophilic and hydrophobic interface. These chemical and/or physical properties, mentioned above of an emulsifiable lipid permit emulsification. Examples of interfaces include, for example, micelles and bilayers. The hydrophilic group can be a polar group and can be charged or uncharged.

In one embodiment, the emulsifiable lipid is derived from animal or vegetable origins, such as, for example, palm kernel oil, soybean oil, cottonseed oil, canola oil, and poultry fat, including hydrogenated type I vegetable oils. In one embodiment, the lipid is hydrogenated. In another embodiment, the lipid is saturated or partially saturated. Examples of emulsifiable lipids include, but are not limited to, monoglycerides, diglycerides, fatty acids, esters of fatty acids, phospholipids, salts thereof, and combinations thereof.

The emulsifiable lipid is preferably a food grade emulsifiable lipid. Some examples of food grade emulsifiable lipids include sorbitan monostearates, sorbitan tristearates and calcium stearoyl lactylates. Examples of food grade fatty acid esters which are emulsifiable lipids include acetic acid esters of mono- and diglycerides, citric acid esters of mono- and di-glycerides, lactic acid esters of mono- and digylcerides, polyglycerol esters of fatty acids, propylene glycol esters of fatty acids, and diacetyl tartaric acid esters of mono- and diglycerides. Lipids can include, for example, hydrogenated soy oil. Any emulsifiable lipid may be used in the methods and products of this disclosure. In one embodiment, the emulsifiable lipid used will produce non-agglomerating, non-aerosolizing enzyme preparation particles.

In another embodiment, the method relates to preparation of an encapsulated, controlled release digestive enzyme preparation with enhanced flow properties useful in the treatment of individuals with Celiac Disease or a related disorder, the method comprising: a) blending an emulsifiable lipid with one or more additives to obtain a blend; and b) coating screened digestive enzyme with the blend to form an encapsulated digestive enzyme containing a core which contains the digestive enzyme and a coating which contains the blend of emulsifiable lipid.

The coating of the enzyme with the lipid allows for the enzyme to become more uniform in size and shape, but reduces the jagged edges associated with the raw enzyme, and allows for ease of administration and ease of packaging, as the flow properties associated with the covered enzyme will allow for the packaging machinery to easily fill the sachet/pouch with the enzyme and reduces overfilling or underfilling of the sachet.

In another embodiment, the disclosure relates to a method of controlling the rate of release of a digestive enzyme from the encapsulated preparation by using a lipid blend to coat the digestive enzyme. The method includes blending an emulsifiable lipid with one or more additives to obtain a blend, and coating the digestive enzyme with the blend to form an encapsulated digestive enzyme containing a core which contains the digestive enzyme and a coating which contains the blend of emulsifiable lipid. The rate of release of the enzyme from the encapsulated preparation upon exposure with a solvent is decreased as the amount of additive is increased. In the alternative, the rate of release of the enzyme from the encapsulated composite upon exposure with a solvent is increased as the amount of additive is decreased. Thus, the nature of the coating allows for controlled release of the enzyme from the encapsulate.

Different dosage forms have different benefits. Tablets and capsules are the most common dosage forms for oral administration due to ease of manufacture, packaging and administration. Different forms of tablets have been primarily devised to meet the needs of select populations while maintaining the integrity of the active pharmaceutical ingredient. Some populations, notably infants and young children, cannot swallow tablets or capsules or find it difficult to do so. In these instances, a tablet that dissolves under the tongue, in the mouth, or in a specified liquid, or one that could be harmlessly chewed would be beneficial. Capsules that could be opened and their contents sprinkled over a small amount of food or in a liquid would also be beneficial. Any improvement that eases the administration of a necessary medication or lessens the antagonism associated with said administration, without compromising the effectiveness of the active pharmaceutical ingredient, is worthwhile.

Other types of solid dosage forms such as thin strips, lollipops or gum bring a novel concept to the administration of medications to children. Aside from the obvious ease of administration from the viewpoint of the caregiver, there may be an added benefit. The administration of medication is oftentimes a private issue and the ability of a caregiver to provide a dose of medication in a seemingly matter-of-fact form may preserve that perception and instill in the user a mindset that views the administration as pleasant rather than monotonous or negative.

Liquid dosage forms also provide benefits of administration to infants and young children or anyone with compromised swallowing capability. Syrups, solutions and suspensions are easily swallowed. Unpleasant tastes can be masked by flavoring. An oral spray allows for the quick administration of a pre-measured dose of medication and supplies multiple metered doses in one handy device. With no need to aid swallowing (such as a glass of water, etc.) and the convenience of not having to rifle through a bottle of tablets, administration is simplified.

A tablet is a mixture of active substances and excipients, usually in powder form, pressed or compacted into a solid. The excipients include binders, glidants (flow aids) and lubricants to ensure efficient tableting; disintegrants to ensure that the tablet breaks up in the digestive tract; sweeteners or flavors to mask the taste of bad-tasting active ingredients; and pigments to make uncoated tablets visually attractive. A coating (sugar, enteric or film) may be applied to hide the taste of the tablet's components, to make the tablet smoother and easier to swallow, and to make it more resistant to the environment, extending its shelf life. Tablets may be buffered (by potassium metaphosphate, potassium phosphate, monobasic sodium acetate, etc.) to combat change in pH. Tablets may be delayed-release, sustained-release, extended-release, controlled-delivery, long-acting, orally-disintegrating or melts, among others, often denoting the pharmacokinetic profile of the active agent. A capsule-shaped tablet is a caplet.

Some tablets may be taken sublingually or allowed to dissolve in the mouth. The principle behind sublingual administration is simple. When a chemical comes in contact with the mucous membrane beneath the tongue, or buccal mucosa, it diffuses through it. Because the connective tissue beneath the epithelium contains a profusion of capillaries, the substance then diffuses into them and enters the venous circulation. Troches are medicated lozenges designed to dissolve in the mouth. Soluble tablets dissolve on contact with the tongue.

Slurry may be made when a dissolvable tablet containing a gelling agent is added to a liquid.

Tablets may also be micro-coated and placed in a capsule for administration.

The compositions described herein can be administered either alone or more typically in combination with one or more of a conventional pharmaceutical carrier, excipient buffer, stabilizer or the like. Such materials should be non-toxic and should not interfere with the efficacy of the active ingredient. The precise nature of the carrier or other material will depend on the route of administration. The term "excipient" is used herein to describe any ingredient other than the compound(s) (enzymes) used in the composition as described herein and known in the art.

Acceptable carriers are physiologically acceptable to the administered patient and retain the therapeutic properties of the compounds with/in which it is administered. Acceptable carriers and their formulations are and generally described in, for example, Remington' pharmaceutical Sciences (18th Edition, ed. A. Gennaro, Mack Publishing Co., Easton, Pa. 1990). Two exemplary carriers are water and physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from the administration site to a portion of the body. Each carrier is acceptable in the sense of being compatible with the other ingredients of the formulation and not injurious to a subject to whom it is administered. Nor should an acceptable carrier alter the specific activity of the subject compounds.

Acceptable carriers, excipients, or stabilizers are those that are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; and/or non-ionic surfactants such as TWEEN®, PLURONICS® or polyethylene glycol (PEG).

In one embodiment, coating of a digestive enzyme preparation is used to obtain release at selected transit times or in selected locations of the gastrointestinal tract of humans. In one aspect, this invention relates to controlled release enzyme preparations administered to a subject with Celiac Disease or related disorders. In another aspect of the present invention one or more coatings are utilized to target delivery to the small intestines.

In yet another aspect, this invention relates to an enzyme delivery system comprising a coated enzyme preparation having particles which comprise: (a) a core comprising pancreatic or digestive enzymes present in an amount from about 5% to 95% by weight of the particles; and (b) a generally uniform coating to provide for controlled release of the enzymes, said coating comprising an emulsifiable lipid. In one aspect, the coated enzyme preparation particles of the enzyme delivery system are non-aerosolizable.

The present invention also relates to methods of making the enzyme preparations by lipid coating and/or encapsulation of digestive enzymes. The methods comprise providing an emulsifiable lipid, and coating optionally screened pancreatic/digestive enzyme particles with the lipid. The digestive enzymes comprise 5 to 95% of the coated enzyme preparations by weight.

In another aspect as described herein, the inventors have discovered that the methods of this invention produce coated digestive enzyme preparations comprising digestive and/or pancreatic enzymes coated with an emulsifiable lipid alone, or with a lipid blend to achieve a controlled rate of enzyme release, with increased release of the pancreatic/digestive enzyme upon exposure of the coated preparation to a suitable solvent. The inventors have discovered that coated pancreatic/digestive enzyme preparations having a coating consisting essentially of one or more monoglycerides exhibit increased release of the pancreatic/digestive enzymes upon exposure of the coated composite to a solvent, such as water, while protecting against release in 0.1 N HCl.

The nature of the human digestive tract creates challenges for the delivery of digestive enzymes to patients susceptible to treatment with digestive enzymes. Multiple temperature and pH changes over the course of the digestive tract make specific delivery a necessity and a challenge. For instance, pH as low as 1 is encountered in the stomach, but rapidly increases to a more basic pH of 5-6 in the proximal small intestine. For example, the pH in the stomach is approximately 1.2, the pH in the duodenum is about 5.0 to 6.0; the pH in the jejunum is about 6.8, and the pH is about 7.2 in the proximal ileum and about 7.5 in the distal ileum. The low pH in the stomach which changes rapidly to a more basic pH of 5-6 in the proximal small intestine calls for a specific delivery method depending upon where the enzyme is to be delivered.

Delivery of digestive enzymes can also be challenging due to the rapid degradation and denaturing of enzymes at ambient room temperature, as well as the enhanced degradation and denaturing that can occur with high temperature, pressure, humidity and/or exposure to light. Moisture and heat together can quickly destabilize enzymes, reducing their effectiveness, and shortening shelf life, leading to inaccurate dosing. Denaturation or destabilization of the enzymes can reduce their effectiveness by reducing the dose of active enzymes to less than the amount needed for effective treatment. Alternatively, attempting to compensate for the denaturation or destabilization by increasing the dose to ensure an effective level of active enzyme could risk an overdose or overfilling of a capsule or other dosage form. To protect and stabilize the pancreatic/digestive enzyme from unfavorable conditions, such a penetration, decomposition, the pancreatic/digestive enzyme (core) may be coated or encapsulated in a continuous coating containing an emulsifiable lipid. In another aspect, this invention provides new coated enzyme preparations with improved shelf life.

Manufacturers of enzyme preparations have used enteric coatings to deliver lipases in individuals requiring administration of lipases, such as individuals with cystic fibrosis. Because the porcine enzymes are delivered in a mixture of proteases, lipases and amylases, and because these compositions for human consumption were prepared for lipase delivery, the use of these enteric coatings, which include such substances as hypromellose phthalate, dimethicone 1000, and dibutyl phthalate, preclude delivery of proteases at the proper location in the digestive tract. All other enzyme preparations presently on the market contain at least one of these enteric coating substances and/or other additives in the preparation. Some additives that enable manufacturing, such as additives to improve flow properties, may further risk patient reactivity or sensitivity to the enzyme preparation.

In one embodiment the present invention includes a coated digestive enzyme preparation and/or composite, which, in some embodiments is an encapsulated pancreatic/digestive enzyme preparation. In other aspects, the invention includes enzyme delivery systems and pharmaceutical compositions comprising coated pancreatic/digestive enzyme preparations. These coated or encapsulated enzyme preparations contain cores comprising pancreatic or digestive enzyme particles, and a coating comprising an emulsifiable lipid.

The coatings in the digestive/pancreatic enzyme preparations create a barrier to degradation and denaturation, and allow more accurate levels of active enzymes to reach the treated individuals. The lipid coating of this invention provides a significant barrier to moisture, heat, humidity and exposure to light by allowing for a physical barrier as well as one that prevents and/or reduces hydrolysis. The coated enzyme preparations undergo less hydrolysis as a result of protection from moisture in the environment by the lipid coating. As a result of the present invention, pancreatic/digestive enzymes are provided which can tolerate ranges of storage conditions (e.g., moisture, heat, oxygen, etc.) for long periods of time thus enabling extended shelf life. The coating of the encapsulated enzyme preparation protects the enzyme from the environment and provides emulsification in a solvent without detracting from the abrasion resistance of the coating. The invention thus further relates to more stable enzyme preparations.

It is another aspect of the present invention to make an enzyme preparation without the use of extenders, colorants, dyes, flow enhancers and other additives to reduce the potential for allergens and other sensitivity reactions in children and other treated individuals. It has been discovered that in some embodiments, the digestive enzymes can be encapsulated with a single lipid excipient to improve retention of enzyme activity, ease of administration, tolerability, and safety of administration, among other properties. Surprisingly, digestive enzyme particles containing lipases can be successfully encapsulated with coating consisting essentially of only hydrogenated soy oil.

In addition, porcine pancreatic/digestive enzymes possess a significant odor and taste, similar to cured/smoked pork. This taste can be strong and offensive to some individuals taking enzyme replacement, and especially to children. The addition of a lipid coating provides significant taste masking to the enzyme preparation, which allows for the tolerance of taste, as the lipid coating is odorless and tasteless. The use of this method of taste masking which does not involve the use of color, dyes, perfumes or other substances is preferable for the administration of medications, which have an unpleasant or undesirable taste and odor. In other embodiments, this invention relates to coated digestive enzyme preparations with improved taste and smell.

In addition, the encapsulation also provides controlled release of the pancreatic/digestive enzyme. The emulsification properties of the coating in a solvent allows for controlled release of the enzyme in the gastrointestinal system, preferably the region of the GI tract where the enzymes are to be utilized. The coating of the encapsulated composite protects the enzyme from the environment and provides emulsification in a solvent without detracting from the abrasion resistance of the coating. For example, for conditions requiring treatment with proteases, the release of the protease portion of the enzymes is necessary in the proximal small intestine, thereby necessitating a lipid encapsulation which has a dissolution profile between 30-90 minutes. The dissolution profile may also be about 30, 35, 40, 45, 50, 55, 60, 65, 70, 75, 80, 85 or 90 minutes. Dissolution profiles may be obtained using methods and conditions known to those of skill in the art. For example, dissolution profiles can be determined at various pHs, including pH 1, 2, 3, 4, 5, 6, 7, 8, 9, 10.

The rate of release of the bioactive substance can also be controlled by the addition of additives as described below. When the preparations are exposed to a solvent, the solvent interacts with the mollifiable lipid in the coating and results in emulsification of the coating and release of the bioactive substance.

"Encapsulate" as used herein means that the coating completely surrounds the pancreatic/digestive enzyme. In a population of encapsulated particles, encapsulated enzyme preparations may include improperly coated or small portion of particles with a substantially continuous coating as long as the release profiles of the encapsulated particles are not significantly altered. A coated or encapsulated particle may contain one or more digestive enzyme particles enveloped in one coating to form one coated or encapsulated digestive enzyme particle in the coated or encapsulated digestive enzyme preparation.

In some aspects, the invention relates to the production of selected coated enzyme preparations made by coating digestive enzyme particles with lipids not previously used in coated digestive enzyme preparations. The unique mixtures of emulsifiable lipids and enzymes can deliver certain components of the pancreatic/digestive enzymes to selected locations and/or at selected times during transit of the GI tract. In some aspects, the invention relates to methods of delivering digestive enzymes to humans based upon dissolution profiles.

The emulsifiable lipid is any lipid, lipid mixture, or blend of lipid and emulsifiers which emulsifies when exposed to a solvent, and has a melting point which allows the lipid to be a solid at typical storage temperatures. The emulsifiable lipid can be a vegetable or animal derived-lipid. In some embodiments, the emulsifiable lipid consists essentially of, or comprises one or more monoglycerides, diglycerides or triglycerides, or other components including, for example, emulsifiers found in hydrogenated vegetable oils. In another embodiment the lipid is a non-polar lipid.

As used herein, animal and/or vegetable "derived" lipids can include fats and oils originating from plant or animal sources and/or tissues, and/or synthetically produced based on the structures of fats and oils originating from plant or animal sources. Lipid material may be refined, extracted or purified by known chemical or mechanical processes. Certain fatty acids present in lipids, termed essential fatty acids, must be present in the mammalian diet. The lipid may, in some embodiments, comprise a Type I U.S.P.-National Formulary vegetable oil.

The digestive enzyme used in the present invention can be any combination of digestive enzymes of a type produced by the pancreas, including, but not limited to digestive enzymes from a pancreatic source or other sources. The scope of the invention is not limited to pancreatic enzymes of porcine origin, but can be of other animal or plant origin as well as those which are synthetically derived. The digestive enzyme may be derived from mammalian sources such as porcine-derived digestive enzymes. The enzyme may include one or more enzymes, and can also be plant derived, synthetically derived, recombinantly produced in microbial, yeast, or mammalian cells, and can include a mixture of enzymes from one or more sources. Digestive enzyme can include, for example, one or more enzymes from one or more sources mixed together. This includes, for example, the addition of single digestive enzymes to digestive enzymes derived from pancreatic sources in order to provide appropriate levels of specific enzymes that provide more effective treatment for a selected disease or condition. One source of digestive enzymes can be obtained, for example, from Scientific Protein Laboratories. The digestive enzyme may be, for example a pancreatin/pancrelipase composition. In one embodiment, the digestive enzymes will comprise or consist essentially of 25 U.S.P. units/mg protease, 2 U.S.P. units/mg lipase, and 25 U.S.P. units/mg amylase. The term digestive enzyme may refer to one or more enzymes of a type produced by the pancreas.

The digestive enzyme particles used as cores in the present invention may include digestive enzyme particles where about 90% of the particles are between about #40 and #140 USSS mesh in size, or between about 105 to 425 μm, or where at least about 75% of the particles are between about #40 and #80 mesh, or about 180 to 425 μm in size. Particles between #40 and #140 mesh in size pass through #40 mesh but do not pass through #140 mesh. The coated or encapsulated digestive enzyme particles in one embodiment of this invention may comprise less than about 35, 30, 25, 20, 15 or 10% of the particles which can be sieved through #100 mesh (150 μm). In some embodiments, the term "non-aerosolizable" refers to a coated or encapsulated enzyme preparation where less than about 20% or less than about 15% of the particles can be sieved through #100 mesh (150 μm). The encapsulated digestive enzyme preparation can be an encapsulated digestive enzyme composite where the digestive enzyme particles contain two or more enzymes.

The particles may also be screened to obtain particles of a suitable size for encapsulation by removing particles that are too fine or too large. For example, the particles may be sieved to obtain particles of a suitable size or more uniform size range for encapsulation. As a further example, the particles may be sieved through USSS #40 mesh and through USSS #140 mesh. Particles that pass through the #40 mesh but are retained by the #140 mesh are of an appropriate size range for coating or encapsulation Particles may also be screened by sieving through USSS #140, #120, #100, #80, #70, #60, #50, #45, or #40 mesh, or any combination thereof. As used in connection with % particles that can be sieved, the term "about" can refer to plus or minus 10, 9, 8, 7, 6, 5, 4, 3, 2 or 1% or anywhere in-between.

The minimum amount of pancreatic enzyme present in the core is at least about 5% active enzymes by weight of the coated enzyme preparation, but in other embodiments may be at least about 30%, or at least about 50% by weight. The maximum amount of pancreatic/digestive enzyme present in the composite is at most about 95% by weight, and in other embodiments at most about 90%, 85%, 80%, 75% or 70% of the coated enzyme preparation. In other embodiments, the amount of pancreatic enzyme present in the composite is about 10%, 15%, 20%, 25%, 35%, 40%, 45%, 55%, 60%, 65%, 70%, 72.5%, 75%, 77.5%, 80%, 82.5%, 87.5%, or 92.5% by weight or anywhere in between. At least about or at most about a % of enzyme may include equal to or about that % of enzyme.

The composition which contains the encapsulated digestive enzyme preparation or composite can be delivered as a sprinkle, powder, capsule, tablet, pellet, caplet or other form. Packaging the encapsulated enzyme preparations in an enzyme delivery system that further comprises single dose sachet-housed sprinkle preparations allows for ease of delivery and accurate dosing of the enzyme, by allowing a specific amount of enzyme to be delivered in each dosing. Allowing for specific unit dosing of an enzyme preparation which maintains the enzyme activity within specific stability parameters is an enhancement over other sprinkle formulations, which are housed in a multi-unit dosing form that allows for air, moisture and heat to depredate and denature the enzyme preparation. In a preferred embodiment the powder or sachet is housed in a trilaminar foil pouch or similar barrier to keep out moisture and to protect the enzyme preparation from adverse environmental factors. The invention further relates to an improvement in stability due to a reduction in hydrolysis due to the lipid encapsulation.

Further the lipid encapsulation methodology reduces the aerosolization of the enzyme preparation that may be caustic to a child if inhaled through the lungs or the nose. In another embodiment, the invention includes delivery of digestive enzymes with improved safety of administration, by reducing the amount of aerosolization of the enzyme. The lipid encapsulation reduces aerosolization and the potential for caustic burn, aspiration, and/or aspiration pneumonias in children and administrators of the enzyme preparation, thereby reducing the potential for illness in already compromised children such as those with cystic fibrosis, and leading to safer administration.

As used herein, the term "non-aerosolizable" will be used to refer to a coated or encapsulated enzyme preparation where substantially all of the particles are large enough to eliminate or reduce aerosolization upon pouring of the coated enzyme preparation compared to uncoated enzyme particles. For example, the term "non-aerosolizable" may refer to a coated or encapsulated enzyme preparation where at least about 90% of the particles are between about #40 and #140 mesh in size, or between about 106 to 425 µm, or where at least about 75% of the particles are between about #40 and #80 mesh, or about 180 to 425 µm. The term "non-aerosolizable" may also refer to a coated or encapsulated enzyme preparation where less than about 35, 30, 25, 20, 15 or 10% of the particles can be sieved through #100 mesh (150 µm). In some embodiments, the term "non-aerosolizable" refers to a coated or encapsulated enzyme preparation where less than about 20% or less than about 15% of the particles can be sieved through #100 mesh (150 µm).

As described and referred to herein, suitable pancreatic/digestive enzymes and suitable coatings may be used in the compositions and methods of this invention. The choice of suitable enzymes and of suitable lipid coatings, including choice of the type or amount of enzymes or coating, are guided by the specific enzyme needs of the individuals, and the selected diseases to be treated. The encapsulated enzyme preparations that are one aspect of this invention have not been previously described.

While general methods for coating certain sensitive biologic substances have been described, see, e.g., U.S. Pat. No. 6,251,478, hereby incorporated by reference, the encapsulated bioactive substance of this invention is an enzyme preparation comprising a core containing digestive enzymes comprising or consisting of multiple proteases, lipases and amylases, and a coating which comprises or consists essentially of an emulsifiable lipid.

Additives can be blended with the emulsifiable lipid. Selection of the lipid(s) and additives will control the rate of release of the bioactive substance. In the case of the digestive and or pancreatic enzymes, the lipid coat must be uniquely chosen to release the bioactive substance in the area of the digestive tract selected for release to optimize treatment.

Because in some embodiments the lipid encapsulation method does not require the enzyme preparation to be treated with solvents, extenders and excipients to facilitate flow or improve stability, one aspect of the invention includes a "clean" preparation of GRAS substances (generally regarded as safe) to be administered. The reduction in the use of solvents, extenders, excipients and other additives permitted by the methods of this invention reduces the exposure of the individuals taking the enzyme replacement to potential allergens, thereby producing a hypoallergenic enzyme preparation that further enhances its potential uses in the treatment of individuals who might otherwise develop an allergic response to treatment. Administration of the coated enzyme preparations of this invention can thus reduce exposure to potentially toxic substances and will also reduce the possibility of allergy formation. Accordingly, in some embodiments, the encapsulated digestive enzyme preparation is hypoallergenic.

In another embodiment, the invention relates to a method of controlling the rate of release of the pancreatic/digestive enzyme from an encapsulated enzyme preparation upon exposure to a solvent. In some aspects, the method comprises blending an emulsifiable lipid with an amount of one or more additives to obtain a lipid blend; and coating the digestive enzyme particle with the blend to form an encapsulated digestive enzyme preparation containing particles comprising a core which contains the enzyme, and a coating which contains the lipid. In some embodiments, the emulsifiable lipid is a blend where the emulsifiable lipid and additive are not the same, and where the rate of release of the enzyme from the encapsulated composite upon exposure to a solvent is decreased as the amount of additive is increased. In the alternative, the rate of release of the enzyme from the encapsulated composite upon exposure to a solvent is increased as the amount of additive is decreased.

The lipid coating surprisingly does not appear to be reduced or destroyed by hydrochloric acid (HCl) present in the stomach, thereby protecting the enzyme from degradation following administration until the enzyme preparation reaches its target region in the GI tract. Further the lipid coat reduces the exposure of the enzyme to attack by water, thereby reducing hydrolysis, and further protecting the digestive enzymes from degradation. In addition, the inventors have found that an excipient containing only lipid can be used to coat or encapsulate digestive enzyme particles containing lipase.

Enzyme preparations supplied by the API supplier may be provided as irregularly shaped, multi-sized particles with uneven edges, and much clumping, and containing some crystalline salt particles. Uneven particle size and shape reduces flow properties and interferes with packaging. In addition, pouring uncoated enzyme into the mouth of a subject would be difficult, and potentially may cause too much or too little of the enzyme to be delivered. Processing the digestive enzyme particles according to methods in accordance with one aspect of this invention yields a non-dusty, free-flowing particulate preparation suitable for sachet packaging and for pouring onto food or drink. In addition, as discussed throughout, the use of lipid encapsulation to prevent aerosolization, (and therefore increase safety) and to increase flow properties, which enhance manufacturing of a pharmaceutical, is an embodiment of the instant invention.

The size distribution of particles in an exemplary raw enzyme preparation is shown in the graph in FIG. 3. Large particles (>20 mesh) and very small particles (<140 mesh) are generally not suitable for proper encapsulation and can be removed by screening. In order to increase the flow properties of the encapsulated pancreatic enzyme preparation, digestive enzyme particles can be sieved to remove fines and overly large particles, for example by including only particles of sizes obtainable by using screens of USSS 20-140 mesh, or about 105 to 841 microns. In some embodiments, the coated digestive enzyme preparation containing 80% digestive enzyme by weight is made by coating sieved pancreatic enzyme particles with a hydrogenated vegetable oil using 20 lbs. of enzyme particles and 5 lbs of hydrogenated vegetable oil. In some embodiments, the temperature of the lipid or lipid blend is maintained at 110° F. before application to the digestive enzymes, which are not heated.

In some embodiments, the lipid should be present in the preparation at a minimum amount of about 5% by weight of the encapsulated composite, preferably about 30%, and more preferably about 50% by weight of the encapsulated composite. The maximum amount of pancreatic/digestive enzyme present in the encapsulated composite is about 95% by weight of the composite, preferably about 90%, and more preferably about 85% of the encapsulated composite. The emulsifiable lipid can be any lipid or lipid-derived material that emulsifies or creates an emulsion yet has a melting point which allows the emulsifiable lipid to be a solid at typical storage temperatures, for example, 23 degrees Centigrade.

"Emulsifiable lipids" as used herein means those lipids which contain at least one hydrophilic group and at least one hydrophobic group, and have a structure capable of forming a hydrophilic and hydrophobic interface. These chemical and/or physical properties, mentioned above, of an emulsifiable lipid permit emulsification. Examples of interfaces include, for example, micelles and bilayers. The hydrophilic group can be a polar group and can be charged or uncharged.

The emulsifiable lipid can be derived from animal or vegetable origins, such as, for example, palm kernel oil, soybean oil, cottonseed oil, canola oil, and poultry fat, including hydrogenated type I vegetable oils. In some embodiments, the lipid is hydrogenated. The lipid can also be saturated or partially saturated. Examples of emulsifiable lipids include, but are not limited to, monoglycerides, diglycerides, fatty acids, esters of fatty acids, phospholipids, salts thereof, and combinations thereof.

The emulsifiable lipid is preferably a food grade emulsifiable lipid. Some examples of food grade emulsifiable lipids include sorbitan monostearates, sorbitan tristearates, calcium stearoyl lactylates, and calcium stearoyl lactylates. Examples of food grade fatty acid esters which are emulsifiable lipids include acetic acid esters of mono- and diglycerides, citric acid esters of mono- and diglycerides, lactic acid esters of mono- and digylcerides, polyglycerol esters of fatty acids, propylene glycol esters of fatty acids, and diacetyl tartaric acid esters of mono- and diglycerides. Lipids can include, for example, hydrogenated soy oil. Any emulsifiable lipid may be used in the methods and products of this invention. In certain embodiments the emulsifiable lipid used will produce non-agglomerating, non-aerosolizing enzyme preparation particles.

In other embodiments, the method relates to preparation of an encapsulated, controlled release digestive enzyme preparation with enhanced flow properties useful in the treatment of individuals with Celiac Disease, the method comprising: a) blending an emulsifiable lipid with one or more additives to obtain a blend; and b) coating screened digestive enzyme with the blend to form an encapsulated digestive enzyme containing a core which contains the digestive enzyme and a coating which contains the blend of emulsifiable lipid.

The coating of the enzyme with the lipid allows for the enzyme to become more uniform in size and shape. reduces the jagged edges associated with the raw enzyme and allows for ease of administration and ease of manufacturing, as the flow properties associated with the covered enzyme will allow for the manufacturing machinery to easily fill the sachet/pouch with the enzyme and reduces overfilling or underfilling of the sachet. The unit dose packaging reduces the ability of a child to open the multidose can/box/or other container. The trilaminar foil pouch or sachet further reduces the ability of a child to open the sachet/pouch, prohibiting possible overdose.

In another embodiment, the invention relates to a method of controlling the rate of release of a digestive enzyme from the encapsulated preparation by using a lipid blend to coat the digestive enzyme. The method includes blending an emulsifiable lipid with one or more additives to obtain a blend, and coating the digestive enzyme with the blend to form an encapsulated digestive enzyme containing a core which contains the digestive enzyme and a coating which contains the blend of emulsifiable lipid. The rate of release of the enzyme from the encapsulated preparation upon exposure with a solvent is decreased as the amount of additive is increased. In the alternative, the rate of release of the enzyme from the encapsulated composite upon exposure with a solvent is increased as the amount of additive is decreased. Thus, the nature of the coating allows for controlled release of the enzyme from the encapsulate.

Non-emulsifiable lipids do not possess the chemical and/or physical properties related to emulsification as described above and include any lipid, lipid derived material, waxes, organic esters, or combinations thereof. Non-emulsifiable lipids generally do not emulsify by themselves. Non-emulsifiable lipids can be used as additives so long as the properties of the coating, and constituent lipids, permit emulsification. Non-emulsifiable lipids, such as, for example, triglycerides, can be blended with an emulsifiable lipid of the present invention. The non-emulsifiable lipid can be derived from animals, vegetables, mineral, or synthetic origins. The non-emulsifiable lipid is preferably hydrogenated, and can be saturated or partially saturated, and includes, but is not limited to triglycerides. In a preferred embodiment, the coating contains a blend of monoglycerides and triglycerides applied to a pancreatic/digestive enzyme.

The inclusion of one or more additives with an emulsifiable lipid of the present invention is used to control emulsification of the coating and release of the enzyme. For example, the additive, triglyceride, can be blended with monoglycerides (e.g., an emulsifiable lipid), to control emulsification of the coating and thus control (e.g., decrease) the rate of release of the enzyme from the composite. As a further example, one or more additives, such as a diglyceride and a triglyceride can be blended with the emulsifiable lipid to control the rate of release of the enzyme. Hydrogenated vegetable oils may contain emulsifying agents, such as soy lecithin or other components.

Properties including mechanical strength, melting point and hydrophobicity can be considered when choosing a suitable lipid coating for the digestive enzyme. Lipids having lower melting points or more polar, hydrophilic properties were generally less suitable for encapsulation because they resulted in product that would cake under accelerated storage stability conditions. Enzyme preparations made using, for example, hydrogenated soy oil, hydrogenated castor wax, and carnauba wax all demonstrated good pouring and no caking.

The wax can be paraffin wax; a petroleum wax; a mineral wax such as ozokerite, ceresin, or montan wax; a vegetable wax such as, for example, carnauba wax, bayberry wax, or flax wax; an animal wax such as, for example, spermaceti; or an insect wax such as beeswax.

Additionally, the wax material can be an ester of a fatty acid having 12 to 31 carbon atoms and a fatty alcohol having 12 to 31 carbon atoms, the ester having from a carbon atom content of from 24 to 62, or a mixture thereof. Examples include myricyl palmitate, cetyl palmitate, myricyl cerotate, cetyl myristate, ceryl palmitate, ceryl certate, myricyl melissate, stearyl palmitate, stearyl myristate, and lauryl laurate.

In a further embodiment, the invention provides a method for controlling rate of release of a pancreatic/digestive enzyme from an encapsulated composite upon exposure to a solvent. The method includes coating the enzyme with an amount of an emulsifiable lipid to form an encapsulated pancreatic enzyme substance composite, wherein the rate of release of the enzyme from the encapsulated composite is decreased as the amount of emulsifiable lipid based on total weight of the encapsulated composite is increased. In the alternative, the rate of release of the pancreatic enzyme from the encapsulated composite is increased as the amount of emulsifiable lipid based on total weight of the encapsulated composite is decreased. The emulsifiable lipid useful in this embodiment can consists essentially of one or more monoglycerides.

The solvent in which a lipid emulsifies can be an aqueous solvent. The aqueous solvent interacts with the hydrophilic groups present in the emulsifiable lipid and disrupts the continuity of the coating, resulting in an emulsion between the aqueous solvent and the lipids in the coating, thus releasing the bioactive substance from the composites.

Compositions described herein may also be formulated for administration as a suppository. For example, a gel formulated into a suppository would be one preferred product form for administration of digestive enzymes to mucosal surfaces of either the rectum or the vagina. Methods of making suppositories are known in the art and contemplated herein.

The phrase "pharmaceutically acceptable" refers to molecular entities and compositions that are physiologically tolerable and do not typically produce an allergic or similar untoward reaction, such as gastric upset, dizziness and the like, when administered to a human.

Dosages and Methods of Treatment

Methods of preparing dosage forms are known, or will be apparent, to those skilled in this art; for example, see Remington: The Science and Practice of Pharmacy, 21st Edition (Lippincott Williams & Wilkins. 2005). Appropriate dosages will depend on the patient (age, weight, overall health, etc.), the severity of the condition, the type of formulation and other factors known to those having ordinary skill in the art. It is to be noted that concentrations and dosage values can vary with the severity of the condition. It is to be further understood that for any particular patient, specific dosage regimens should be adjusted over time according to the individual need and the professional judgment of the person administering or supervising the administration of the compositions.

The invention also relates to a specific blend of enzymes, with or without coating, with or without other components as described above whereby enzyme administration occurs in individuals with Celiac Disease and related disorders, including but not limited to: Celiac Disease, celiac sprue, non-tropical sprue, gluten-sensitive enteropathy and irritable bowel syndrome.

Provided herein is a method for alleviating symptoms of Celiac Disease and related conditions including also known as sprue, non-tropical sprue, gluten intolerance or gluten-sensitive enteropathy. The method comprises the administration to a subject of a digestive enzyme either naturally or recombinantly derived, or their derivatives in an amount effective to reduce the symptoms of celiac and related conditions.

In one aspect, provided herein is a method for treating a subject exhibiting one or more symptoms of Celiac Disease and related disorders, the method comprising administering a therapeutically effective amount of digestive enzymes to the individual. In one embodiment, the disorders comprise: Celiac Disease, non-tropical sprue and celiac sprue.

In another embodiment, the symptoms of Celiac Disease and other related disorders which are potentially suited for alleviation according to the present method are selected from the group consisting of gastrointestinal symptoms and include but are not limited to: irritable bowel syndrome, protein deficiency, iron-deficiency anemia caused by menstrual blood loss or protein deficiency, inflammatory bowel disease, diverticulitis, intestinal infections, stool abnormalities, diarrhea which may be protracted or intermittent, constipation, alternating constipation with diarrhea, abdominal pain, bloating, gas or indigestion, decreased appetite (may also be increased or unchanged), lactose intolerance, nausea and vomiting, stools that float, are foul smelling, bloody, or "fatty", and unexplained weight loss.

In another embodiment, the symptoms of celiac and related disorders which are potentially suited for alleviation according to the present method are selected from those which represent neurological or neuropsychiatric symptoms and include but are not limited to: depression, anxiety, chronic headaches, migraines, fatigue, memory loss, dementia, mania, hypomania, malaise (which may be protracted) seizures, tingling or numbness especially in the extremities and the head, seizures, and irritable and fussy behavior in children.

In another embodiment, the symptoms of celiac and related disorders which are potentially suited for alleviation according to the present method are selected from those which represent metabolic, dermatological, immunological or hormonal or symptoms and include but are not limited to: bruising easily, hair loss, mouth ulcers, nosebleeds, missed menstrual periods, Vitamin B12 deficiency, vitamin deficiencies, mineral deficiencies, osteoporosis, delayed growth in children, itchy skin (dermatitis herpetiformis), muscle cramps, joint pain, short stature, poor weight gain, slowed growth, failure to thrive, low cholesterol, pancreatic cancer, lymphoma, gastric cancer, colon cancer, and intestinal cancer.

Individuals with Celiac Disease and other associated disorders generally exhibit one or more symptoms of the disease or disorder. In addition, they often exhibit symptoms of co-morbid conditions such as thyroid disease, autoimmune disorders such as Rheumatoid Arthritis, Systemic Lupus Erythematosus, and Sjogren Syndrome, as well as Addison's Disease, Down Syndrome, Turner Syndrome, lactose intolerance and Type 1 Diabetes.

Recognition and determination of a reduction in symptoms of Celiac Disease, related disorders and resultant symptomatology can be performed by those skilled in the art. The skilled artisan will recognize that those who suffer from the related disorders can potentially have Celiac Disease.

The recognition of the symptoms of celiac and related disorders present in a subject and determination that the present method may alleviate said symptoms prior to, during, or after the practice of this method is well within the purview of a subject ordinarily skilled in the art, who can perform suitable clinical, diagnostic, and/or observational or other techniques required.

Another aspect of the invention relates to the method for treating Celiac Disease and related disorders in a subject comprising administering an effective amount of a composition comprising one or more digestive enzymes to the individual. In one embodiment the symptoms of Celiac Disease and related disorders are selected from a group comprising gastrointestinal symptoms and include, but are not limited to, irritable bowel syndrome, protein deficiency, iron-deficiency anemia caused by menstrual blood loss or protein deficiency, inflammatory bowel disease, diverticulitis, intestinal infections, stool abnormalities, diarrhea which may be protracted or intermittent, constipation, alternating constipation with diarrhea, abdominal pain, bloating, gas or indigestion, decreased appetite (may also be increased or unchanged), lactose intolerance, nausea and vomiting, stools that float, are foul smelling, bloody, or "fatty", and unexplained weight loss. In yet another embodiment the symptoms comprise those which are neurological or neuropsychiatric symptoms and include but are not limited to: depression, anxiety, chronic headaches, migraines, fatigue, memory loss, dementia, mania, hypomania, malaise (which may be protracted) seizures, tingling or numbness especially in the extremities and the head, seizures and irritable and fussy behavior in children. In another embodiment, the symptoms are metabolic, dermatological, immunological or hormonal and include, but are not limited to, bruising easily, hair loss, mouth ulcers, nosebleeds, missed menstrual periods, low cholesterol, Vitamin B12 deficiency, vitamin deficiencies, mineral deficiencies, osteoporosis, delayed growth in children, itchy skin (dermatitis herpetiformis), muscle cramps, joint pain, short stature, poor weight gain, slowed growth, failure to thrive, lymphoma, gastric cancer, colon cancer, intestinal cancer, and pancreatic cancer.

The invention further relates to methods for administering the enzyme preparations. In some aspects, the methods include administering the pancreatic/digestive enzymes as coated preparations. In some aspects, the invention relates to a method of treatment comprising administering to a subject with Celiac Disease or related disorders, including but not limited to: Celiac Disease, celiac sprue, non-tropical sprue, and gluten-sensitive enteropathy, irritable bowel syndrome, and chronic fatigue, in need of treatment with digestive enzymes, at least two doses of a composition comprising a therapeutically effective amount of a coated or uncoated digestive enzyme preparation comprising a core comprising a digestive enzyme; and in the case of a coated enzyme preparation, a coating comprising an emulsifiable lipid. Determination of whether a subject is in need of treatment with an effective amount of digestive enzymes may be based on a determination that the subject has an enzyme deficiency.

In yet another aspect, the methods include administering the pancreatic/digestive enzymes as coated preparations. In some aspects, the invention relates to a method of treatment comprising administering to a subject with Celiac Disease or related disorders, including but not limited to those who exhibit gastrointestinal symptoms which include but also are not limited to: irritable bowel syndrome, protein deficiency, iron-deficiency anemia caused by menstrual blood loss or protein deficiency, inflammatory bowel disease, diverticulitis, intestinal infections, stool abnormalities, diarrhea which may be protracted or intermittent, constipation, alternating constipation with diarrhea, abdominal pain, bloating, gas or indigestion, decreased appetite (may also be increased or unchanged), lactose intolerance, nausea and vomiting, stools that float, are foul smelling, bloody, or "fatty", and unexplained weight loss; in need of treatment with digestive enzymes, at least two doses of a composition comprising a therapeutically effective amount of a coated or uncoated digestive enzyme preparation comprising a core comprising a digestive enzyme; and in the case of a coated enzyme preparation, a coating comprising an emulsifiable lipid. Determination of whether a subject is in need of treatment with an effective amount of digestive enzymes may be based on a determination that the subject has an enzyme deficiency.

In yet another aspect, the methods include administering the pancreatic/digestive enzymes as coated preparations. In some aspects, the invention relates to a method of treatment comprising administering to a subject with Celiac Disease or related disorders, including but not limited to those who exhibit neurological or neuropsychiatric symptoms and include but are not limited to: depression, anxiety, chronic headaches, migraines, fatigue, memory loss, dementia, mania, hypomania, malaise (which may be protracted) seizures, tingling or numbness especially in the extremities and the head, seizures and irritable and fussy behavior in children, in need of treatment with digestive enzymes, at least two doses of a composition comprising a therapeutically effective amount of a coated or uncoated digestive enzyme preparation comprising a core comprising a digestive enzyme; and in the case of a coated enzyme preparation, a coating comprising an emulsifiable lipid. Determination of whether a subject is in need of treatment with an effective amount of digestive enzymes may be based on a determination that the subject has an enzyme deficiency.

In yet another aspect, the methods include administering the pancreatic/digestive enzymes as coated preparations. In some aspects, the invention relates to a method of treatment comprising administering to a subject with Celiac Disease or related disorders, including but not limited to those who exhibit metabolic, dermatological, immunological or hormonal or symptoms and include but are not limited to: bruising easily, hair loss, mouth ulcers, nosebleeds, missed menstrual periods, low cholesterol, Vitamin B12 deficiency, vitamin deficiencies, mineral deficiencies, osteoporosis, delayed growth in children, itchy skin (dermatitis herpetiformis), muscle cramps, joint pain, short stature, poor weight gain, slowed growth, failure to thrive, lymphoma, gastric cancer, colon cancer, intestinal cancer and pancreatic cancer, in need of treatment with digestive enzymes, at least two doses of a composition comprising a therapeutically effective amount of a coated or uncoated digestive enzyme preparation comprising a core comprising a digestive enzyme; and in the case of a coated enzyme preparation, a coating comprising an emulsifiable lipid. Determination of whether a subject is in need of treatment with an effective amount of digestive enzymes may be based on a determination that the subject has an enzyme deficiency.

In another aspect of the invention, it is well known that determining a dosage regimen of the compound is well within the purview of those skilled in the art. By way of example, the dose levels may range from 900 milligrams to 10 grams as determined by weight. Further activity of the enzymes may range from 100 units of activity to 1,000,000 units of activity per dose for amylases, lipases and proteases.

In some embodiments, each dose contains about 100 to 1500 mg of coated or encapsulated enzyme preparation, and each dose may contain about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500 mg of coated or encapsulated enzyme preparation. "About" can include 80 to 125% of the recited preparation. Each dose may also be plus or minus 2%, 5%, or 10% of the recited weight. In one embodiment each does will have a protease activity of not less than about 156 U.S.P. units/dose ±2%, 5%, or 10%. The protease activity may also be not less than about 100, 105, 110, 115, 120, 125, 130, 135, 140, 145, 150, 155, 160, 165, 170, 175, 180, 185, 190, 195, or 200 U.S.P. units/dose.

In another embodiment, the invention relates to methods of treatment comprising administering to a subject with a neurological or neuropsychiatric condition susceptible to treatment with digestive enzymes, at least two doses of a composition comprising a therapeutically effective amount of the coated digestive enzyme preparations. In certain embodiments, about 80% of the enzyme is released by about 30 minutes in a dissolution test performed at pH 6.0. In other embodiments, about 80% of the enzyme is released by about 30 minutes after the coated digestive enzyme preparations reach the small intestine.

The invention further relates in another aspect to the delivery of digestive enzymes with improved safety of administration. The lipid coat adds weight to the enzyme preparation, which reduces the potential for aerosolization. Previous uncoated enzymes have been shown to become aerosolized, and can therefore be inhaled and contact the nasal cavity or the lungs, causing injury to the mucosa of those taking and those administering the enzyme preparation.

The invention further relates to the improvement of administering a sachet preparation for delivery to children. The invention specifically relates to the administration of a coated digestive enzyme preparation, housed in a sachet which allows for particular types of administration including but not limited to administration in food, drink, or direct administration into the oral cavity or directly into the GI system through a NG-tube, G-tube or other GI entrances. The use of a sachet delivery of enzymes has heretofore been not utilized in the enzyme preparations presently marketed. In one embodiment, the sachet represents a single unit dosage or multiple doses for a day. The sachet of a trilaminar foil allows the enzyme/lipid powder to remain stable, and allows for ease of administration.

The methods further relate to the administering of the coated and/or encapsulated enzyme preparation in a sachet or pouch preparation for ease of delivery to children and adults. In some embodiments, the invention specifically relates to the administration of a coated enzyme particle preparation, housed in a sachet or pouch. This facilitates administration, including but not limited to, administration in food or drink, direct administration into the oral cavity, or administration directly into the GI system through an NG-tube, G-tube or other GI entrances or deliveries.

Compositions comprising an effective amount of the compound may be administered via any conventional route including but not limited to oral, parenteral, intramuscular, intravenous, transmucosal, transdermal, via suppository or other method. Further the oral administration can be in the form of pellets, capsules, caplets, beadlets, sprinkles, tablets, softgels or other carrier.

The pharmaceutical formulations can also be prepared for parenteral use. Such formulations typically take the form of sterile isotonic solutions of the active ingredient according to standard pharmaceutical practice.

In one embodiment of the present invention, the increase of protein digestion of a subject suffering from Celiac Disease or other related disorders leads to the improvement of such disorders. In another embodiment, a subject suffering from or diagnosed with Celiac Disease or related disorders benefits from the administration of digestive enzymes since digestive enzymes aid in the protein digestion process. In one embodiment, the Celiac Disease or related disorder symptoms of a subject suffering from or diagnosed with celiac or related disorders is improved or alleviated from the administration of digestive enzymes.

The present invention provides a method for using digestive enzymes and their derivatives to alleviate the symptoms of celiac or related disorders. The method comprises administering to the individual a digestive enzyme either naturally or recombinantly derived, or their derivatives, in an amount effective to reduce the symptoms of Celiac Disease or related disorders.

In another embodiment of the invention the administration of digestive enzymes to those with celiac or related disorders who exhibit symptoms of said disease or disorders is utilized to examine the efficacy of the digestive enzyme preparation with respect to administration of an effective amount of the enzyme and evaluating the enzyme's effect on the reduction of symptomatology associated with Celiac Disease or related disorders.

The application of these enzymes of the high protease classification as applied to individuals with Celiac Disease or related disorders represents a novel discovery for the use of digestive enzymes.

In one embodiment a composition can be administered 1 or more times a day, such as 1, 2, 3, 4, 5, 6, 7, 8, 9, or 10 times a day with or without food. In another embodiment, a composition can be administered orally 3 times a day with or without food.

The term "unit dose" when used in reference to a therapeutic composition refers to physically discrete units suitable as unitary dosage for humans, each unit containing a predetermined quantity of active material calculated to produce the desired therapeutic effect in association with the required diluent; i.e., carrier, or vehicle.

Provided herein are methods for administering the enzyme compositions/preparations. In one aspect, the methods include administering the pancreatic/digestive enzymes as coated preparations. In another aspect, the disclosure relates to a method of treatment comprising administering to a subject with Celiac Disease or a related disorder, including but not limited to: bruising easily, hair loss, mouth ulcers, nosebleeds, missed menstrual periods, Vitamin B12 deficiency, vitamin deficiencies, mineral deficiencies, osteoporosis, delayed growth in children, itchy skin (dermatitis herpetiformis), muscle cramps, joint pain, short stature, poor weight gain, slowed growth, failure to thrive, low cholesterol, pancreatic cancer, lymphoma, gastric cancer, colon cancer, intestinal cancer, Autoimmune disorders such as rheumatoid arthritis, systemic lupus erythematosus, and Sjogren syndrome; Addison's disease; Down syndrome; Intestinal cancer; Intestinal lymphoma; Lactose intolerance; Thyroid disease; and/or Type 1 diabetes. The method comprises administering to the individual a digestive enzyme either naturally or recombinantly derived, or their derivatives, in an amount effective to reduce the symptoms of celiac and related disorders. The enzymes may be coated or uncoated.

The present invention provides a method for using digestive enzymes and their derivatives to alleviate one or more symptoms of Celiac Disease or a related disorder. Symptoms to be alleviated include, but are not limited to, gastrointestinal symptoms and include, but are not limited to, irritable bowel syndrome, protein deficiency, iron-deficiency anemia caused by menstrual blood loss or protein deficiency, inflammatory bowel disease, diverticulitis, intestinal infections, stool abnormalities, diarrhea which may be protracted or intermittent, constipation, alternating constipation with diarrhea, abdominal pain, bloating, gas or indigestion, decreased appetite (may also be increased or unchanged), lactose intolerance, nausea and vomiting, stools that float, are foul smelling, bloody, or "fatty", and unexplained weight loss.

In one aspect of the present disclosure, it is well known that determining a dosage regimen of the compound is well within the purview of those in the art. By way of example, the dose levels may range from 100 milligrams to 10 grams as determined by weight. Further activity of the enzymes may range from 100 units of activity to 1,500,000 units of activity per dose for amylases, lipases and proteases, respectively.

In another embodiment, the disclosure relates to methods of treatment comprising administering to a subject with a neurological or neuropsychiatric condition susceptible to treatment with digestive enzymes, at least two doses of a composition comprising a therapeutically effective amount of the coated digestive enzyme preparations. In certain embodiments, about 80% of the enzyme is released by about 30 minutes in a dissolution test performed at pH 6.0. In other embodiments, about 80% of the enzyme is released by about 30 minutes after the coated digestive enzyme preparations reach the small intestine.

The disclosure further relates in another aspect to the delivery of digestive enzymes with improved safety of administration. The lipid coat adds weight to the enzyme preparation, which reduces the potential for aerosolization. Previous uncoated enzymes have been shown to become aerosolized, and can therefore be inhaled and contact the nasal cavity or the lungs, causing injury to the mucosa of those taking and those administering the enzyme preparation.

The disclosure further relates to the improvement of administering a sachet preparation for delivery to children. The disclosure specifically relates to the administration of a coated or uncoated digestive enzyme preparation, housed in a sachet which allows for particular types of administration including but not limited to administration in food, drink, or direct administration into the oral cavity or directly into the GI system through a NG-tube, G-tube or other GI entrances. The use of a sachet delivery of enzymes has heretofore not been utilized in the enzyme preparations presently marketed. In one embodiment, the sachet represents a single unit dosage or multiple doses for a day. The sachet of a trilaminar pouch allows the enzyme or enzyme/lipid powder to remain stable, and allows for ease of administration.

The disclosure further relates to the administering of the coated or uncoated enzyme preparation in a sachet or pouch preparation for ease of delivery to children and adults. In some embodiments, the disclosure specifically relates to the administration of a coated or uncoated enzyme particle preparation, housed in a sachet or pouch. This facilitates administration, including but not limited to, administration in food or drink, direct administration into the oral cavity, or administration directly into the GI system through an NG-tube, G-tube or other GI entrances or deliveries.

Compositions comprising an effective amount of the compound may be administered via any conventional route including but not limited to oral, parenteral, intramuscular, intravenous, transmucosal, transdermal, suppository or other method. Further the oral administration can be in the form of pellets, capsules, caplets, beadlets, sprinkles, tablets, softgels or other carrier.

In one embodiment of the present disclosure, the increase of protein digestion of a subject suffering from Celiac Disease or a related disorder to the improvement of such disease or disorders. In another embodiment, a subject suffering from or diagnosed with Celiac Disease benefits from the administration of digestive enzymes. In one embodiment, the neuropsychiatric symptoms of a subject suffering from or diagnosed with Celiac Disease is improved or alleviated from the administration of digestive enzymes.

The present invention provides a method for using digestive enzymes and their derivatives to alleviate the symptoms of Celiac Disease. The method comprises administering to the individual a digestive enzyme either naturally or recombinantly derived, or their derivatives, in an amount effective to reduce one or more symptoms of Celiac Disease.

Provided herein are methods of preventing one or more symptoms associated with Celiac Disease by administering a composition described herein. As used herein, "prevention" refers to prophylaxis, prevention of onset of symptoms, prevention of progression of a Celiac Disease. As used herein, "inhibition", "prevention", "treatment" and "treating" refer to, for example, stasis of symptoms, as well as partial or full amelioration of one or more symptoms associated with Celiac Disease. Because Celiac Disease is hereditary, family members of a person with the disease may wish to be tested. Such patients can be monitored and be treated as needed with a composition described herein.

Compositions can be administered to a patient in an amount that is effective for producing some desired therapeutic effect by alleviating one or more symptoms associated with Celiac Disease at a reasonable benefit/risk ratio applicable to any medical treatment. A therapeutically effective amount is an amount achieves at least partially a desired therapeutic or prophylactic effect in tissue subject. The amount of digestive enzymes necessary to bring about alleviation one or more symptoms associated with Celiac Disease is not fixed per se. The amount of digestive enzymes administered may vary with the type of disorder, extensiveness of the disorder, and size of the patient suffering from the disorder. A response is achieved when the patient experiences partial or total alleviation, or reduction of one or more signs or symptoms of illness. The patient's symptoms can remain static (i.e., not get worse) or can be reduced.

A physician can readily determine and prescribe the effective amount (ED50) of the composition required. For example, the physician could start doses of the compounds employed in the composition at levels lower than that required in order to achieve the desired therapeutic effect and gradually increase the dosage until the desired effect is achieved. Alternatively, a dose can remain constant.

In such methods of treatment, one or more symptoms are ameliorated or reduced following administration of a composition provided herein. In one embodiment, one or more symptoms of such disorders are reduced in severity or duration by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100%. In another embodiment, one or more symptoms of such disorders are reduced in severity or duration by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold or more.

The diagnostic criteria described above may be used to assess whether administration of a composition described herein reduces the severity and/or duration of one or more symptoms of Celiac Disease or a related disorder.

In yet another embodiment, the duration of symptoms may be reduced in severity and/or duration following administration of a composition described herein. That is, one or more symptoms may persist for less than 6 months, 5 months, 4 months, 3 months, 2 months, 1 month, 3 weeks, 2 weeks or 1 week.

Combination Therapy

Another aspect provided herein is combination therapy of a patient with a composition described herein along with another therapeutically effective agent or rehabilitation. Such treatments include, but are not limited to, administration of monoclonal-, or polyclonal-, monomeric, dimeric, or polymeric IgA; peptide inhibitors of gliadin peptides; gluten-free diet.

Treatment may also be combined with an adherence to a lifelong gluten-free diet, thereby allowing the intestinal villi to heal. Foods, beverages, and medications that contain wheat, barley, and rye are eliminated. Wheat, rye, and barley are the grains that contain pathogenic peptides. Gastrointestinal symptoms in patients with symptomatic Celiac Disease who adhere to a gluten-free diet typically resolve within a few weeks.

A gluten-free diet means not eating foods that contain wheat, rye and barley. The foods and products made from these grains should also be avoided. In other words, a person with Celiac Disease should not eat most grain, pasta, cereal and many processed foods.

Despite these restrictions, people with Celiac Disease can eat a well-balanced diet with a variety of foods. They can use potato, rice, soy, amaranth, quinoa, buckwheat, or bean flour instead of wheat flour. They can buy gluten-free bread, pasta, and other products from stores that carry organic foods, or order products from special food companies. "Plain" meat, fish, rice, fruits, and vegetables do not contain gluten, so people with Celiac Disease can freely eat these foods. In the past, people with Celiac Disease were advised not to eat oats. New evidence suggests that most people can safely eat small amounts of oats, as long as the oats are not contaminated with wheat gluten during processing.

People with Celiac Disease should work closely with their health care team when deciding whether to include oats in their diet. The gluten-free diet requires a completely new approach to eating. Newly diagnosed people and their families may find support groups helpful as they learn to adjust to a new way of life. People with Celiac Disease must be cautious about what they buy for lunch at school or work, what they purchase at the grocery store, what they eat at restaurants or parties, and what they grab for a snack. Eating out can be a challenge. When in doubt about a menu item, a person with Celiac Disease should ask the waiter or chef about ingredients and preparation or if a gluten-free menu is available.

Gluten is also used in some medications. People with Celiac Disease should ask a pharmacist if prescribed medications contain wheat. Because gluten is sometimes used as an additive in unexpected products—such as lipstick and Play Dough—reading product labels is important. If the ingredients are not listed on the label, the manufacturer should provide a list upon request. With practice, screening for gluten becomes second nature.

In addition to meats and vegetable and gluten free dairy foods, the following are allowable foods for those with gluten sensitivity/Celiac Disease:

Acacia Gum; Acesulfame K; Acesulfame Potassium; Acetanisole; Acetophenone; Acorn Quercus; Adipic Acid; Adzuki Bean; Acacia Gum; Agar; Agave; Albumen; Alcohol (Spirits—Specific Types); Alfalfa; Algae; Algin; Alginic Acid; Alginate; Alkalized Cocoa; Allicin; Almond Nut; Alpha-amylase; Alpha-lactalbumin; Aluminum; Amaranth; Ambergris; Ammonium Hydroxide; Ammonium Phosphate; Ammonium Sulphate; Amylose; Amylopectin; Annatto; Annatto Color; Apple Cider Vinegar; Arabic Gum; Arrowroot; Artichokes; Artificial Butter Flavor; Artificial Flavoring; Ascorbic Acid; Aspartame (can cause IBS symptoms); Aspartic Acid; Aspic; Astragalus Gummifer; Autolyzed Yeast Extract; Avena Sativia; Avena Sativia Extract; Avidin; Azodicarbonamide; baking soda; Balsamic Vinegar; Beeswax; Beans; Bean, Adzuki; Bean, Hyacinth; Bean, Lentil; Bean, Mung; Bean Romano (Chickpea); Bean Tepary; Benzoic acid; Besan (Chickpea); Beta Glucan; Betaine; Beta Carotene; BHA; BHT; Bicarbonate of Soda; Biotin; Blue Cheese; Brown Sugar; Buckwheat; Butter (check additives); Butylated Hydroxyanisole; Butyl Compounds; Calcium Acetate; Calcium Carbonate; Calcium Caseinate; Calcium Chloride; Calcium Disodium; Calcium Hydroxide; Calcium Lactate; Calcium Pantothenate; Calcium Phosphate; Calcium Propionate; Calcium Silicate; Calcium Sorbate; Calcium Stearoyl Lactylate; Calcium Stearate; Calcium Sulfate; Calrose; Camphor; Cane Sugar; Cane Vinegar; Canola (Rapeseed); Canola Oil (Rapeseed Oil); Caprylic Acid; Carageenan Chondrus Crispus; Carbonated Water; Carboxymethyl; Cellulose; Carmine; Carnauba Wax; Carob Bean; Carob Bean Gum; Carob Flour; Carrageenan; Casein; Cassava Manihot Esculenta; Castor Oil; Catalase; Cellulose; Cellulose Ether; Cellulose Gum; Cetyl Alcohol; Cetyl Stearyl Alcohol; Champagne Vinegar; Channa (Chickpea); Chana Flour (chickpea flour); Cheeses; Chestnuts; Chickpea; Chlorella; Chocolate Liquor; Choline; Chloride; Chromium; Citrate; Chymosin; Citric Acid; Citrus Red No. 2; Cochineal; Cocoa; Cocoa Butter; Coconut; Coconut Vinegar; Collagen; Colloidal Silicon Dioxide; Confectioner's Glaze; Copernicia Cerifera; Copper Sulphate; Corn; Corn Gluten; Corn Masa Flour; corn meal; Corn Flour; corn starch; Corn Sugar; Corn Sugar Vinegar; Corn Syrup; Corn Syrup Solids; Corn Sweetener; Corn Vinegar; Corn Zein; Cortisone; Cotton Seed; Cotton Seed Oil; Cowitch; Cowpea; Cream of Tartar; Crospovidone; Curds; Cyanocobalamin; Cysteine, L; Dal (Lentils); D-Alpha-tocopherol; Dasheen Flour (Taro); Dates; D-Calcium Pantothenate; Delactosed Whey; Demineralized Whey; Desamidocollagen; Dextran; Dextrose; Diglycerides; Dioctyl Sodium; Dioctyl Sodium Solfosuccinate; Dipotassium Phosphate; Disodium Guanylate; Disodium Inosinate; Disodium Phosphate; Distilled Alcohols; Distilled Vinegar; Distilled White Vinegar; Dutch Processed Cocoa; EDTA (Ethylenediaminetetraacetic Acid); Eggs; Egg Yolk; Elastin; Ester Gum; Ethyl Alcohol; Ethylenediaminetetraacetic Acid; Ethyl Maltol; Ethyl Vanillin; Expeller Pressed Canola Oil; FD&C Blue No. 1 Dye; FD&C Blue No. 1 Lake; FD&C Blue No. 2 Dye; FD&C Blue No. 2 Lake; FD&C Green No. 3 Dye; FD&C Green No. 3 Lake; FD&C Red No. 3 Dye; FD&C Red No. 40 Dye; FD&C Red No. 40 Lake; FD&C Yellow No. 5 Dye; FD&C Yellow No.

6 Dye; FD&C Yellow No. 6 Lake; Ferric Orthophosphate; Ferrous Gluconate; Ferrous Fumerate; Ferrous Lactate; Ferrous Sulfate; Fish (fresh); Flaked Rice; Flax; Folacin; Folate; Folic Acid-Folacin; Formaldehyde; Fructose; Fruit (including dried); Fruit Vinegar; Fumaric Acid; Galactose; Garbanzo Beans; Gelatin; Glucoamylase; Gluconolactone; Glucose; Glucose Syrup; Glutamate (free); Glutamic Acid; Glutamine (amino acid); Glutinous Rice; Glutinous rice flour; Glycerides; Glycerin; Glycerol Monooleate; Glycol Monosterate; Glycol; Glycolic acid; Gram flour (chick peas); Grape Skin Extract; Grits, Corn; Guar Gum; Gum Acacia; Gum Arabic; Gum Base; Gum Tragacanth; Hemp; Hemp Seeds; Herbs; Herb Vinegar; Hexanedioic Acid; High Fructose Corn Syrup; Hominy; Honey; Hops; Horseradish (Pure); Hyacinth Bean; Hydrogen Peroxide; Hydrolyzed Caseinate; Hydrolyzed Meat Protein; Hydrolyzed Soy Protein; Hydroxypropyl Cellulose; Hydroxypropyl Methylcellulose; Hypromellose; Illepe; Iodine; Inulin; Invert Sugar; Iron Ammonium Citrate; Isinglass; Isolated Soy Protein; Isomalt; Jowar (Sorghum); Karaya Gum; Kasha (roasted buckwheat); Keratin; K-Carmine Color; K-Gelatin; Koshihikari (rice); Kudzu; Kudzu Root Starch; Lactalbumin Phosphate; Lactase; Lactic Acid; Lactitol; Lactose; Lactulose; Lanolin; Lard; L-cysteine; Lecithin; Lemon Grass; Lentils; Licorice; Licorice Extract; Lipase; L-leucine; L-lysine; L-methionine; Locust Bean Gum; L-tryptophan; Magnesium Carbonate; Magnesium Hydroxide; Magnesium Oxide; Maize; Maize Waxy; Malic Acid; Maltitol; Maltodextrin; Maltol; Manganese Sulfate; Manioc; Masa; Masa Flour; Masa Harina; Meat (fresh); Medium Chain Triglycerides; Menhaden Oil; Methyl Cellulose; Microcrystalline Cellulose; Micro-particulated Egg White Protein; Milk; Milk Protein Isolate; Millet; Milo (Sorghum); Mineral Oil; Mineral Salts; Molybdenum Amino Acid Chelate; Monocalcium Phosphate; Monoglycerides; Mono and Diglycerides; Monopotassium Phosphate; Monosaccharides; Monosodium Glutamate (MSG); Monostearates; Mung Bean; Musk; Mustard Flour; Myristic Acid; Natural Smoke Flavor; Niacin-Niacinamide; Neotame; Niacin; Niacinamide; Nitrates; Nitrous Oxide; Non-fat Milk; Nuts (except wheat, rye & barley); Nut, Acron; Nut, Almond; Oils and Fats; Oleic Acid; Oleoresin; Olestra; Oleyl Alcohol/Oil; Orange B; Oryzanol; Palmitic Acid; Pantothenic Acid; Papain; Paprika; Paraffin; Patially Hydrogenated Cottonseed Oil; Patially Hydrogenated Soybean Oil; Peas; Pea—Chick; Pea—Cow; Pea Flour; Pea Starch; Peanuts; Peanut Flour; Pectin; Pectinase; Peppermint Oil; Peppers; Pepsin; Peru Balsam; Petrolatum; PGPR (Polyglycerol Polyricinoleate); Phenylalanine; Phosphoric Acid; Phosphoric Glycol; Pigeon; Peas; Polenta; Polydextrose; Polyethylene Glycol; Polyglycerol; Polyglycerol; Polyricinoleate (PGPR); Polysorbates; Polysorbate 60; Polysorbate 80; Potassium Benzoate; Potassium Caseinate; Potassium Citrate; Potassium Iodide; Potassium Lactate; Potassium Matabisulphite; Potassium Sorbate; Potatoes; Potato Flour; potato starch; Povidone; Prinus; Pristane; Propolis; Propylene Glycol; Monosterate; Propyl Gallate; Protease; Psyllium; Pyridoxine Hydrochloride; Quinoa; Ragi; Raisin Vinegar; Rape; Recaldent; Reduced Iron; Rennet; Rennet Casein; Resinous Glaze; Reticulin; Riboflavin; Rice; Rice (Enriched); Rice Flour; Rice Starch; Rice Syrup; Rice Vinegar; Ricinoleic Acid; Romano Bean (chickpea); Rosematta; Rosin; Royal Jelly; Saccharin; Saffron; Sago; Sago Palm; Sago Flour; Sago Starch; Saifun (bean threads); Salt; Seaweed; Seeds (except wheat, rye & barley); Seed—Sesame; Seed—Sunflower; Shea; Sherry Vinegar; Silicon Dioxide; Soba (be sure its 100% buckwheat); Sodium Acid Pyrophosphate; Sodium Acetate; Sodium Alginate; Sodium Ascorbate; Sodium Benzoate; Sodium Caseinate; Sodium Citrate; Sodium Erythrobate; Sodium Hexametaphosphate; Sodium Lactate; Sodium Lauryl Sulfate; Sodium Metabisulphite; Sodium Nitrate; Sodium Phosphate; Sodium Polyphosphate; Sodium; Silaco Aluminate; Sodium; Stearoyl Lactylate; Sodium Sulphite; Sodium Stannate; Sodium Tripolyphosphate; Sorbic Acid; Sorbitan Monostearate; Sorbitol-Mannitol (can cause IBS symptoms); Sorghum; Sorghum Flour; Soy; Soybean; Soy Lecithin; Soy Protein; Soy Protein Isolate; Spices (pure); Spirits (Specific Types); Spirit Vinegar; Stearates; Stearamide; Stearamine; Stearic Acid; Stearyl Lactate; Stevia; Sunflower Seed; Succotash (corn and beans); Sucralose; Sucrose; Sulfosuccinate; Sulfites; Sulfur Dioxide; Sweet Chestnut Flour; Tagatose; Tallow; Tapioca; tapioca flour; Tapioca Starch; Tara Gum; Taro; Tarro; Tarrow Root; Tartaric Acid; Tartrazine; TBHQ is Tetra or Tributylhydroquinone; Tea; Tea-Tree Oil; Teff; Teff Flour; Tepary Bean; Textured Vegetable Protein; Thiamin Hydrochloride; Thiamine Mononitrate; Thiamine Hydrochloride; Titanium Dioxide; Tofu (Soy Curd); Tolu Balsam; Torula Yeast; Tragacanth; Tragacanth Gum; Triacetin; Tricalcium Phosphate; Tri-Calcium Phosphate; Trypsin; Turmeric (Kurkuma); TVP; Tyrosine; Urad/Urid Beans; Urad/Urid Dal (peas) Vegetables; Urad/Urid flour; Urd; Vinegar (All except Malt); Vanilla Extract; Vanilla Flavoring; Vanillin; Vinegars (Specific Types); Vitamin A (retinol); Vitamin A Palmitate; Vitamin B1; Vitamin B-12; Vitamin B2; Vitamin B6; Vitamin D; Vitamin E Acetate; Waxy Maize; Whey; Whey Protein Concentrate; Whey Protein Isolate; White Vinegar; Wines; Wine Vinegars (& Balsamic); Wild Rice; xanthan Gum; Xylitol; Yam Flour; Yeast; Yogurt (plain, unflavored); Zinc Oxide; and Zinc Sulfate.

The following are the foods which are generally "forbidden" from the gluten free diet: Abyssinian Hard (Wheat *Triticum durum*); Alcohol (Spirits—Specific Types; Amp-Isostearoyl Hydrolyzed Wheat Protein; Atta Flour; Barley Grass (can contain seeds); Barley Hordeum vulgar; Barley Malt; Beer (most contain barley or wheat); Bleached Flour; Bran; bread Flour; Brewer's Yeast; Brown Flour; Bulgur (Bulgar Wheat/Nuts); Bulgur Wheat; Cereal; Binding; Chilton; Club Wheat (*Triticum aestivum* subspecies *compactum*) Common Wheat (*Triticum aestivum*); cookie Crumbs; Cookie Dough; Cookie Dough Pieces; Couscous; Criped Rice; Dinkle (Spelt); Disodium Wheatgermamido Peg-2 Sulfosuccinate; *durum* wheat (*Triticum durum*); Edible Coatings; Edible Films; Edible Starch; Einkorn (*Triticum monococcum*); Emmer (*Triticum dicoccon*); Enriched Bleached Flour; Enriched Bleached Wheat Flour; Enriched Flour; Farina; Farina Graham; Farro; Filler; Flour; Fu (dried wheat gluten); Germ; Graham Flour; Granary Flour; Groats (barley, wheat); Hard Wheat; Heeng; Hing; Hordeum Vulgare; Extract; Hydrolyzed Wheat Gluten; Hydrolyzed Wheat Protein; Hydrolyzed Wheat Protein Pg-Propyl Silanetriol; Hydrolyzed Wheat Starch; Hydroxypropyltrimonium; Hydrolyzed Wheat Protein; Kamut (pasta wheat); Kecap Manis (Soy Sauce); Ketjap Manis (Soy Sauce); Kluski Pasta; Maida (Indian wheat flour); Malt; Malted Barley Flour; Malted Milk; Malt Extract; Malt Syrup; Malt Flavoring; Malt Vinegar; Macha Wheat (*Triticum aestivum*); Matza; Matzah; Matzo; Matzo Semolina; Meringue; Meripro 711; Mir; Nishasta; Oriental Wheat (*Triticum turanicum*); Orzo Pasta; Pasta; Pearl Barley; Persian Wheat (*Triticum carthlicum*); Perungayam; Poulard Wheat (*Triticum turgidum*); Polish Wheat (*Triticum polonicum*); Rice Malt (if barley or Koji are used); Roux; Rusk; Rye; Seitan; Semolina; Semolina *Triticum*; Shot Wheat (*Triticum aestivum*);

Small Spelt; Spirits (Specific Types); Spelt (*Triticum spelta*); Sprouted Wheat or Barley; Stearyldimoniumhydroxypropyl Hydrolyzed Wheat Protein; Strong Flour; Suet in Packets; Tabbouleh Tabouli; Teriyaki Sauce; Timopheevi Wheat (*Triticum timopheevii*); Triticale X triticosecale; *Triticum vulgare* (Wheat); Flour Lipids; *Triticum vulgare* (Wheat); Germ Extract; *Triticum vulgare* (Wheat); Germ Oil; Udon (wheat noodles); Unbleached Flour; Vavilovi Wheat (*Triticum aestivum*); Vital Wheat Gluten; wheat; Abyssinian Hard *Triticum durum*; Wheat amino acids; Wheat Bran Extract; Wheat, Bulgur; wheat *Durum triticum*; wheat Germ Extract; Wheat Germ Glycerides; Wheat Germ Oil; Wheat Germamidopropyldimonium Hydroxypropyl; Hydrolyzed Wheat Protein; Wheat Grass (can contain seeds); Wheat Nuts; Wheat Protein; Wheat *Triticum aestivum*; Wheat *Triticum monococcum*; Wheat (*Triticum vulgare*) Bran Extract; Whole-meal Flour; Wild Einkorn (*Triticum boeotictim*); and Wild Emmer (*Triticum dicoccoides*).

People with Celiac Disease are more likely to have Autoimmune disorders such as rheumatoid arthritis, systemic lupus erythematosus, and Sjogren syndrome; Addison's disease; Down syndrome; Intestinal cancer; Intestinal lymphoma; Lactose intolerance; Thyroid disease; and/or Type 1 diabetes.

Treatment of a patient described herein who exhibits one or more symptoms of Celiac Disease as well as one or more symptoms of the diseases or disorders described may be administered conventional therapy of such one or more symptoms of the diseases or disorders.

Patients typically experience the resolution of the findings of malnutrition, improved growth with resultant normal stature, and normalization of blood and biochemical laboratory studies. Such treatments may be combined with those of the compositions and treatments described herein to facilitate and/or advance resolution of one or more symptoms. Normal results from a follow-up endoscopy with biopsy several months after the diagnosis and treatment confirm the disease.

EXAMPLES

Example 1: Pancreatin

Pancreatin is a substance containing enzymes, principally amylase, lipase, and protease, obtained from the pancreas of the hog *Sus scrofa* Linne var. *domesticus* Gray (Fam. Suidae) or of the ox *Bos taurus* Linne (Fam. Bocidae). Pancreatin contains, in each mg, not less than 25 U.S.P. units of amylase activity, not less than 2 U.S.P. units of lipase activity, and not less than 25 U.S.P. of protease activity. Pancreatin of a higher digestive power may be labeled as a whole-number multiple of the three minimum activities or may be diluted by admixture with lactose, or with sucrose containing not more than 3.25 percent of starch, or with pancreatin of a lower digestive power.

Example 2: Reduction of Gastrointestinal Symptoms

A reduction in gastrointestinal symptoms associated with untreated or partially treated Celiac Disease can be seen when the individuals are administered a digestive enzyme preparation high in proteases including chymotrypsin, trypsin, and other proteases. Said results are obtained within 3-10 days of administration. The methodology as described may be altered accordingly by one skilled in the art of administration of enzymes. One ordinarily skilled in the art would be able to administer the enzyme.

Example 3

One example of an enzyme preparation comprised of amylases, proteases and lipases contains protease in an amount ranging between 155,000 and 310,000 U.S.P. units of protease activity, the main component of the enzyme preparation. The methodology as described may be altered accordingly as one skilled in the art of administration of enzymes or administration. One ordinarily skilled in the art would be able to administer the enzyme.

Example 4

This example describes a method of treating Celiac Disease which includes administering an enzyme preparation comprised of amylases, proteases and lipases. The protease strength range of between 155,000 and 310,000 units of protease activity is the main component of the enzyme preparation. The enzyme preparation administration given to those with Celiac Disease resulted in an increase in weight gain (See Table 2 and FIG. 1).

TABLE 2

| Subject | Sex | AGE | Celiac diagnosis Confirmed | weight pre DE 16 weeks (lbs) | weight post DE 16 weeks (lbs) |
|---|---|---|---|---|---|
| 1 | M | 37 | Yes | 125 | 136 |
| 2 | F | 42 | Yes | 113 | 119 |
| 3 | F | 32 | Yes | 155 | 161 |
| 4 | F | 24 | Yes | 128 | 131 |
| 5 | M | 36 | Yes | 149 | 159 |
| 6 | F | 22 | Yes | 127 | 136 |
| 7 | M | 52 | Yes | 148 | 154 |
| 8 | F | 45 | Yes | 121 | 126 |

Example 5

This example describes a method of treating Celiac Disease which includes administering an enzyme preparation comprised of amylases, proteases and lipases. The protease strength of between 155,000 and 310,000 units of protease activity is the main component of the enzyme preparation. The enzyme administration given to those with Celiac Disease resulted in a decrease in gastrointestinal pain, bloating, loose stools, constipation, diarrhea, flatulence and fatty "floating" stools.

A 34 year old male presented with a history of chronic diarrhea, floating and "fatty" type stools, who has difficulty maintaining weight due to Celiac Disease. The patient was given enzyme therapy with high protease enzymes of at least 350,000 U.S.P. U/dose of protease three times daily with food. A continual gluten-free diet was maintained throughout the 120 days of treatment. There was no co-morbidity or other medication given. The individual suffered from diarrhea, with loose and frequent bowel movements every day regardless of the gluten-free diet. Post enzyme therapy, the individual demonstrated fewer bowel movements per day. On average there were 6-8 bowel movements per day which reduced to 2-3, and the stool was formed instead of soft and mushy. There was no odor associated with the bowel movements after 10 days of taking the enzyme preparation. On day 90 a stool test was performed whereby fecal fat content went from a +3 on day 1 to 0 on day 90. Further, the stool sunk to the bottom of the bowl whereas the stool previously floated, regardless of formation.

A 29 year old female presented with chronic constipation, flatulence and bloating. Causes other than Celiac Disease were ruled out. She presented with continual difficulty after eating, and had been diagnosed with Celiac Disease at age 15. She was administered 300,000 units of protease coupled with amylase and lipase three times daily with food. On day 12 her constipation reduced, and by day 30 she was able to stop her stool softener. On day 30, her bloating reduced with a disappearance of the flatulence. The individual continued to take her enzyme preparation with food. If the individual missed 3 consecutive doses while eating, the flatulence and bloating returned.

Example 6

This example describes a method of treating Celiac Disease which includes administering an enzyme preparation comprised of amylases, proteases and lipases. The protease strength of between 155,000 and 310,000 units of protease activity is the main component of the enzyme preparation. The enzyme administration given to those with Celiac Disease resulted in a decrease in associated neurological symptoms including tingling, numbness, memory loss, tremor, irritability and seizure activity associated with celiac and related disorders according to the Tremor Scale described below.

TABLE 3

Tremor Scale (symptomatic complaint of tremor in any part of the body)

| | |
|---|---|
| 0 = | Absent (no tremor or writing impairment) |
| 1 = | Slight and infrequently present (mild tremor, writing, and drawing of spiral minimally impaired) |
| 2 = | Moderate; bothersome to most patients (writing and drawing of spiral moderately impaired) |
| 3 = | Severe tremor (writing and drawing severely impaired; interferes with many activities such as drinking liquids) |
| 4 = | Marked tremor (interferes with most activities) |

Example 7

This example describes a method of treating Celiac Disease which includes administering an enzyme preparation comprised of amylases, proteases and lipases. The protease strength of between 155,000 and 310,000 units of protease activity is the main component of the enzyme preparation. The enzyme administration given to those with Celiac Disease resulted in a reduction in symptoms which are non GI or neurological: nose bleeds, osteoporosis and muscle cramps associated with celiac and related disorders.

While preferred embodiments have been shown and described herein, it will be obvious to those skilled in the art that such embodiments are provided by way of example only. Numerous variations, changes, and substitutions will now occur to those skilled in the art without departing from the embodiments. It should be understood that various alternatives to the embodiments described herein may be employed in practicing the described compositions and methods. It is intended that the following claims define the scope of the embodiments and that methods and structures within the scope of these claims and their equivalents be covered thereby.

What is claimed is:

1. A method for treating Celiac disease in subject in need thereof who is not on a gluten-free diet, comprising administering to the subject a therapeutically effective amount of a composition that comprises digestive enzymes, wherein the digestive enzymes comprise a protease, an amylase, and a lipase, and wherein the Celiac disease is treated.

2. The method of claim 1, wherein the composition is administered until one or more symptoms of Celiac disease are partially or completely resolved.

3. The method of claim 2, wherein the one or more symptoms are selected from the group consisting of abdominal pain, bloating, gas, indigestion, constipation, decreased appetite, diarrhea, lactose intolerance, nausea, vomiting, unexplained weight loss, bruising easily, depression, anxiety, chronic headaches, migraines, fatigue, growth delay in children, hair loss, itchy skin, missed menstrual periods, mouth ulcers, muscle cramps, joint pain, nosebleeds, seizures, tingling in the hands, tingling in the feet, numbness in the hands, numbness in the feet, unexplained short height, defects in the tooth enamel, changes in tooth color, delayed puberty, irritable behavior, fussy behavior, poor weight gain, slowed growth, shorter than normal height, an abnormal stool, osteoporosis, a vitamin deficiency, a mineral deficiency, malaise, an iron deficiency anemia, pancreatic cancer, lymphoma, gastric cancer, colon cancer, intestinal cancer, dementia, and a combination thereof.

4. The method of claim 1, wherein the composition comprises the protease, and the protease comprises chymotrypsin, trypsin, papain, or a combination thereof.

5. The method of claim 1, wherein the digestive enzymes are animal enzymes, plant enzymes, synthetic enzymes, or a combination thereof.

6. The method of claim 1, wherein the composition is administered to the subject orally.

7. The method of claim 1, wherein a total amount of the protease in the composition is from about 10,000 to about 1,500,000; from about 25,000 to about 1,000,000; from about 50,000 to about 750,000; from about 75,000 to about 500,000; from about 85,000 to about 250,000; from about 95,000 to about 200,000; or from about 110,000 to about 150,000 U.S.P. units/dose.

8. The method of claim 1, wherein a total amount of the amylase in the composition is from about 1,000 to about 15,000,000; from about 5,000 to about 1,000,000; from about 15,000 to about 750,000; from about 50,000 to about 500,000; from about 75,000 to about 250,000; from about 95,000 to about 200,000; or from about 100,000 to about 150,000 U.S.P. units/dose.

9. The method of claim 1, wherein a total amount of the lipase in the composition is from about 1,500 to about 282,000; from about 5,000 to about 200,000; from about 5,000 to about 150,000; from about 75,000 to about 100,000; from about 10,000 to about 75,000; from about 15,000 to about 50,000; or from about 20,000 to about 40,000 U.S.P. units/dose.

10. The method of claim 1, wherein the treatment increases weight gain of the subject.

11. The method of claim 1, wherein the digestive enzymes are provided as pancreatin.

* * * * *